United States Patent
Beilman et al.

(10) Patent No.: US 10,307,398 B2
(45) Date of Patent: Jun. 4, 2019

(54) RESUSCITATION COMPOSITION AND METHODS OF MAKING AND USING

(71) Applicant: Regents of the University of Minnesota, Minneapolis, MN (US)

(72) Inventors: Gregory Beilman, Richfield, MN (US); Andrea Wolf, Minneapolis, MN (US); Raj Suryanarayanan, Roseville, MN (US); Seema Thakral, Fridley, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/710,389

(22) Filed: Sep. 20, 2017

(65) Prior Publication Data

US 2018/0104218 A1    Apr. 19, 2018

Related U.S. Application Data

(60) Provisional application No. 62/397,211, filed on Sep. 20, 2016.

(51) Int. Cl.
| | |
|---|---|
| *A61K 31/4045* | (2006.01) |
| *A61P 7/00* | (2006.01) |
| *A61K 9/19* | (2006.01) |
| *A61K 9/00* | (2006.01) |
| *A61K 9/08* | (2006.01) |
| *A61K 31/19* | (2006.01) |
| *A61K 47/10* | (2017.01) |
| *A61K 47/32* | (2006.01) |
| *A61K 47/40* | (2006.01) |
| *A61K 47/34* | (2017.01) |

(52) U.S. Cl.
CPC ........ *A61K 31/4045* (2013.01); *A61K 9/0019* (2013.01); *A61K 9/08* (2013.01); *A61K 9/19* (2013.01); *A61K 31/19* (2013.01); *A61K 47/10* (2013.01); *A61K 47/32* (2013.01); *A61K 47/34* (2013.01); *A61K 47/40* (2013.01); *A61P 7/00* (2018.01)

(58) Field of Classification Search
None
See application file for complete search history.

(56) References Cited

U.S. PATENT DOCUMENTS

| | | |
|---|---|---|
| 4,298,601 A | 11/1981 | Howard |
| 4,407,821 A | 10/1983 | Mendy |
| 4,663,166 A | 5/1987 | Veech |
| 4,970,143 A | 11/1990 | Gidoux et al. |
| 5,049,388 A | 9/1991 | Knight et al. |
| 5,098,409 A | 3/1992 | Stock |
| 5,100,677 A | 3/1992 | Veech |
| 5,120,763 A | 6/1992 | Yehuda |
| 5,141,674 A | 8/1992 | Leigh |
| 5,176,634 A | 1/1993 | Smith |
| 5,257,985 A | 11/1993 | Puhl |
| 5,405,333 A | 4/1995 | Richmond |
| 5,654,266 A | 8/1997 | Chen |
| 5,700,828 A | 12/1997 | Federowicz et al. |
| 5,719,119 A | 2/1998 | Veech |
| 5,814,663 A | 9/1998 | Cook et al. |
| 5,853,388 A | 12/1998 | Semel |
| 6,107,349 A | 8/2000 | Mantynen |
| 6,232,345 B1 | 5/2001 | Hiraide et al. |
| 6,262,111 B1 | 7/2001 | Agus et al. |
| 6,316,038 B1 | 11/2001 | Veech |
| 6,323,237 B1 | 11/2001 | Veech |
| 6,329,343 B1 | 12/2001 | Leung et al. |
| 6,353,015 B1 | 3/2002 | Oxenkrug et al. |
| 6,890,896 B1 | 5/2005 | Shashoua |
| 7,083,572 B2 | 8/2006 | Unger et al. |
| 7,097,827 B2 | 8/2006 | Platz et al. |
| 8,728,532 B2 | 5/2014 | Andrews et al. |
| 9,149,450 B2 | 10/2015 | Andrews et al. |
| 9,186,340 B2 | 11/2015 | Andrews et al. |
| 2001/0014696 A1 | 8/2001 | Veech |
| 2001/0041736 A1 | 11/2001 | Veech |
| 2001/0051652 A1 | 12/2001 | Nishino et al. |
| 2002/0077317 A1 | 6/2002 | Das |
| 2002/0091080 A1 | 7/2002 | Fruebis et al. |
| 2002/0168430 A1 | 11/2002 | Heeg et al. |
| 2003/0143530 A1 | 7/2003 | Klepp et al. |
| 2003/0219430 A1 | 11/2003 | Faerman |
| 2004/0171671 A1 | 9/2004 | Veech |
| 2004/0223963 A1 | 11/2004 | Cheung et al. |
| 2004/0235960 A1 | 11/2004 | Burns et al. |
| 2005/0129783 A1 | 6/2005 | McCleary et al. |
| 2006/0280721 A1 | 12/2006 | Veech et al. |
| 2007/0299135 A1 | 12/2007 | Martin et al. |
| 2010/0197758 A1 | 8/2010 | Andrews et al. |
| 2011/0111049 A1 | 5/2011 | Andrews et al. |
| 2014/0235690 A1 | 8/2014 | Andrews et al. |
| 2016/0008325 A1 | 1/2016 | Andrews |
| 2018/0104218 A1 | 4/2018 | Beilman et al. |

FOREIGN PATENT DOCUMENTS

| | | |
|---|---|---|
| WO | WO 1991/002535 | 3/1991 |
| WO | WO 1998/041201 | 9/1998 |

(Continued)

OTHER PUBLICATIONS

Wolf et al., "Evaluation of novel formulations of D-β-hydroxybutyrate and melatonin in a rat model of hemorrhagic shock," International Journal of Pharmaceutics, (2018) 548: 104-12. (Year: 2018).*
"Cool Hibernators Scientist Becomes Surgeon to Probe Squirrel for Medical Solutions" [online]. ABCNEWS.com, [retrieved on Oct. 14, 2003]. Retrieved from the Internet: <URL: http://abcnews.go.com/sections/scitech/US/squirrelsurgery031013.html>, 3 pages.
"Novel Approaches to Treatment of Shock," Fluid Resuscitation: State of the Science for Treating Combat Casualties and Civilian Injuries, 1999, Committee on Fluid Resuscitation for Combat Casualties, Institute of Medicine, pp. 79-94.

(Continued)

*Primary Examiner* — Sreenivasan Padmanabhan
*Assistant Examiner* — Jody L Karol
(74) *Attorney, Agent, or Firm* — Fish & Richardson P.C.

(57) ABSTRACT

A resuscitation composition is described herein, as are methods of making and using such a composition.

17 Claims, 28 Drawing Sheets

(56) References Cited

FOREIGN PATENT DOCUMENTS

| WO | WO 2004/047871 | 6/2004 |
|---|---|---|
| WO | WO 2004/096118 | 11/2004 |
| WO | WO 2004/108740 | 12/2004 |
| WO | WO 2005/107724 | 11/2005 |
| WO | WO 2005/107875 | 11/2005 |
| WO | WO 2006/012490 | 2/2006 |
| WO | WO 2006/020137 | 2/2006 |
| WO | WO 2006/020179 | 2/2006 |
| WO | WO 2006/034361 | 3/2006 |
| WO | WO 2006/098767 | 9/2006 |

OTHER PUBLICATIONS

Andrews et al., "Adaptive mechanisms regulate preferred utilization of ketones in the heart and brain of a hibernating mammal during arousal from torpor," Am J Physiol Regul Integr Comp Physiol., 2009, 296: R383-R393, First published Dec. 3, 2008.

Andrews et al., "Low-temperature carbon utilization is regulated by novel gene activity in the heart of a hibernating mammal," Proc. Natl. Acad. Sci. USA, 1998, 95(14):8392-8397.

Andrews, "Advances in molecular biology of hibernation in mammals," BioEssays, 2007, 29:431-440.

Angele et al., "Bench-to-bedside review: latest results in hemorrhagic shock," Crit. Care, 12(4):218, Jul. 2008.

Bauer et al., "Expression of a chimeric retroviral-lipase mRNA confers enhanced lipolysis in a hibernating mammal," Am. J. Physiol. Regul. Integr. Comp. Physiol., 2001, 281(4):R1186-R1192.

Beilman et al., "Near-infrared spectroscopy measurement of regional tissue oxyhemoglobin saturation during hemorrhagic shock," Shock, 1999, 12(3):196-200.

Broer et al., "Characterization of the monocarboxylate transporter 1 expressed in Xenopus laevis oocytes by changes in cytosolic pH," Biochem. J., 1998, 333(Pt 1):167-174.

Buck et al., "Coordinate expression of the PDK4 gene: a means of regulating fuel selection in a hibernating mammal," Physiol. Genomics, 2002, 8(1):5-13.

Carey et al., "Mammalian hibernation: cellular and molecular responses to depressed metabolism and low temperature," Physiol. Rev., 2003, 83(4):1153-1181.

Carpenter and Halestrap, "The kinetics, substrate and inhibitor specificity of the lactate transporter of Ehrlich-Lettre tumour cells studied with the intracellular pH indicator BCECF," Biochem. J., 1994, 304(Pt 3):751-760.

Chen et al., "Melatonin attenuates the postischemic increase in blood-brain barrier permeability and decreases hemorrhagic transformation of tissue-plasminogen activator therapy following ischemic stroke in mice," J. Pineal Res., 2006, 40:242-250.

Chen et al., "Melatonin decreases neurovascular oxidative/nitrosative damage and protects against early increases in the blood-brain barrier permeability after transient focal cerebral ischemia in mice," J. Pineal Res., 2006, 41:175-182.

Clinkenbeard et al., "Molecular and catalytic properties of cytosolic acetoacetyl coenzyme A thiolase from avian liver," J. Biol. Chem., 1973, 248(7):2275-2284.

Cohn et al., "Tissue oxygen saturation predicts the development of organ dysfunction during traumatic shock resuscitation," J. Trauma, 2007, 62(1):44-54.

D'Alecy et al., "β-hydroxybutyrate and response to hypoxia in the ground squirrel, Spermophilus tridecimlineatus," Comp. Biochem. Physiol. B, 1990, 96(1):189-193.

Daya et al., "The effect of variations in pH and temperature on stability of melatonin in aqueous solution," J. Pineal Res., 31(2):155-58, Sep. 2001.

De Lara Rodriguez et al., "Hibernation-based blood loss therapy increases survivability of lethal hemorrhagic shock in rats," J. Comp. Physiol. B., 187(5-6):769-78, Jul. 2017.

Dirnagl et al., "Pathobiology of ischaemic stroke: an integrated view," Trends Neurosci., 1999, 22(9):391-397.

Eastridge et al., "Hypotension begins at 110 mm Hg: redefining "hypotension" with data," J. Trauma, 2007, 63:291-299.

Editorial Note, "Melatonin as an antioxidant: physiology versus pharmacology," J. Pineal Res., 2005, 39:215-216.

Eiger et al., "Hypoxic tolerance enhanced by β-hydroxybutyrate-glucagon in the mouse," Stroke, 1980, 11(5):513-517.

Englehart and Schreiber, "Measurement of acid-base resuscitation endpoints: lactate, base deficit, bicarbonate or what," Curr. Opin. Crit. Care, 2006, 12:569-574.

Flamm et al., "Free Radicals in cerebral ischemia," Stroke, 1978, 9:455-447.

Forder et al., "Dissociation of mitochondrial and contractile function after global hypothermic ischemia: effects of β-hydroxybutyrate," Circulation, 1990, 82(4):Abstract 3006.

Fort et al., "Hemolysis study of aqueous polyethylene glycol 400, propylene glycol and ethanol combinations in vivo and in vitro," J. Parenter. Sci. Technol., Mar. 1984, 38(2):82-7.

Gerhart et al., "Expression of monocarboxylate transporter MCT1 by brain endothelium and glia in adult and suckling rats," Am. J. Physiol., 1997, 273(1 Pt 1):E207-E213.

Gerhart et al., "Expression of the monocarboxylate transporter MCT2 by rat brain glia," Glia, 1998, 22(3):272-281.

Green et al., "Wild type and mutant human heart (R)-3-hydroxybutyrate dehydrogenase expressed in insect cells," Biochemistry, 1996, 35(25):8158-8165.

Hall et al., "Ketone body kinetics in humans: the effects of insulin-dependent diabetes, obesity, and starvation," J. Lipid Res., 1984, 25(11):1184-1194.

Henry et al., "Brain energy metabolism and neurotransmission at near-freezing temperatures: An in vivo 1H MRS study of a hibernating mammal," J. Neurochem., 2007, 101(6):1505-1515.

Heyliger et al. (The Analgesic Effects of Tryptophan and Its Metabolites in the Rat. Pharmacological Research, vol. 38, No. 4, 1998, 243-250.

Holcomb et al., "Damage Control Resuscitation: Directly Addressing the Early Coagulopathy of Trauma," J. Trauma Inj. Infect. Crit. Care., 62(2):307-310, Feb. 2007.

Honda et al., "Down-regulation of cholesterol biosynthesis in sitosterolemia: diminished activities of acetoacetyl-CoA thiolase, 3-hydroxy-3-methylglutaryl-CoA synthase, reductase, squalene synthase, and 7-dehydrocholesterol delta7-reductase in liver and mononuclear leukocytes," J. Lipid Res., 1998, 39(1):44-50.

Iso et al., "Linoleic acid, other fatty acids, and the risk of stroke," Stroke, 2002, 23:2086-2093.

Jackson and Halestrap, "The kinetics, substrate, and inhibitor specificity of the monocarboxylate (lactate) transporter of rat liver cells determined using the fluorescent intracellular pH indicator, 2',7'-bis(carboxyethyl)-5(6)-carboxyfluorescein," J. Biol. Chem., 1996, 271(2):861-868.

Kabine et al., "Hibernation impact on the catalytic activities of the mitochondrial D-3-hydroxybutyrate dehydrogenase in liver and brain tissues of jerboa (Jaculus orientalis)," BMC Biochem., 2003, 4(1):11, 8 pages.

Kauvar et al., "Impact of hemorrhage on trauma outcome: an overview of epidemiology, clinical presentations, and therapeutic considerations," J. Trauma., 60(6 Suppl):S3-11, Jun. 2006.

King et al., "Free fatty acids, but not ketone bodies, protect diabetic rat hearts during low-flow ischemia," Am. J. Physiol. Heart Circ. Physiol., 2001, 280:H1173-H1181.

Kirsch and D'Alecy, "Effect of altered availability of energy-yielding substrates upon survival from hypoxia in mice," Stroke, 1979, 10(3):288-291.

Kirsch and D'Alecy, "Hypoxia induced preferential ketone utilization by rat brain slices," Stroke, 1984, 15(2):319-323.

Klein et al., Small-volume d-β-hydroxybutyrate solution infusion increases survivability of lethal hemorrhagic shock in rats, Shock, 2010, 34(6):565-572.

Klein, "Hibernation strategies to improve recovery from hemorrhagic shock," Jul. 2007, thesis submitted to the faculty of the graduate school of the University of Minnesota, 77 pages.

Koehler-Stec et al., "Monocarboxylate transporter expression in mouse brain," Am. J. Physiol., 1998, 275(3 Pt 1):E516-E524.

(56) References Cited

OTHER PUBLICATIONS

Kraut et al. (Serum Anion Gap: Its Uses and Limitations in Clinical Medicine. Clin J Am Soc Nephrol. Jan. 2007;2(1):162-74. Epub 2006.

Krilowicz, "Ketone body metabolism in a ground squirrel during hibernation and fasting," Am. J. Physiol., 1985, 249(4 Pt 2):R462-R470.

Lavau et al., "Ketone metabolism in brain slices from rats with diet induced hyperketonemia," J. Nutr., 1978, 108(4):621-629.

Leino et al., "Diet-induced ketosis increases monocarboxylate transporter (MCT1) levels in rat brain," Neurochem. Int., 2001, 38(6):519-527.

Leino et al., "Monocarboxylate transporter (MCT1) abundance in brains of suckling and adult rats: a quantitative electron microscopic immunogold study," Brain Res. Dev. Brain Res., 1999, 113(1-2):47-54.

Lipski et al., "Neuroprotective potential of ceftriaxone in in vitro models of stroke," Neuroscience, 2007, 146(2):617-629.

Maldonado et al., "The potential of melatonin in reducing morbidity-mortality after craniocerebral trauma," J. Pineal Res., 2007, 42:1-11.

Masuda et al., "D-β-Hydroxybutyrate is Neuroprotective Against Hypoxia in Serum-free Hippocampal Primary Cultures," J. Neurosci. Res., 2005, 80:501-509.

Mathes et al., "Melatonin pretreatment improves liver function and hepatic perfusion after hemorrhagic shock," Shock, 2008, 29(1):112-118.

Matson and Drewes, "Immunoblot detection of brain vascular proteins," Methods Mol Med. 89:479-487, 2003.

Maus et al., "Pyruvate and lactate protect striatal neurons against N-methyl-D-aspartate-induced neurotoxicity," Eur. J. Neurosci., 1999, 11(9):3215-3224.

Middleton, "The oxoacyl-coenzyme A thiolases of animal tissues," Biochem. J., 1973, 132(4):717-730.

Mulier et al., "Treatment with beta-hydroxybutyrate and melatonin is associated with improved survival in a porcine model of hemorrhagic shock," Resuscitation, Feb. 2012, 83(2):253-8.

Mulier et al., "Hibernation-based therapy in a porcine model of hemorrhagic shock results in improved survival," Presented at 2010 Society of Critical Care Medicine's 39th Critical Care Congress, Miami Beach FL, Jan. 2010, 1 page.

Mulier et al., "Ringer's ethyl pyruvate in hemorrhagic shock and resuscitation does not improve early hemodynamics or tissue energetics," Shock, 2005, 23(3):248-252.

Myers et al., "Noninvasive method for measuring local hemoglobin oxygen saturation in tissue using wide gap second derivative near-infrared spectroscopy," J. Biomed. Opt., 2005, 10(3):1-18.

Nehlig and Pereira de Vasconcelos, "Glucose and ketone body utilization by the brain of neonatal rats," Progress Neurobiol., 1993, 40(2):163-221.

Oliver et al., "Linoleic acid, antioxidants and coronary heart disease," Cardiovascular Dysfunction, 1990, 18:1049-1051.

Page et al., "Activities of enzymes of ketone-body utilization in brain and other tissues of suckling rats," Biochem. J., 1971, 121(1):49-53.

Paller et al., "Free radical scavengers in mercuric chloride-induced acute renal failure in the rat," J. Lab. Clin. Med., 1985, 105(4):459-463.

Pierre et al., "MCT2 is a major neuronal monocarboxylate transporter in the adult mouse brain," J. Cereb. Blood Flow Metab., 2002, 22(5):586-595.

Pope et al., "Fluid Resuscitation: State of the Science for Treating Combat Casualties and Civilian Injuries," Natl. Acad. Press., 54-55, 1999.

PubChem "3-hyroxybutyric acid", pp. 1-33, 2005.

Pull and McIlwain, "3-Hydroxybutyrate dehydrogenase of rat brain on dietary change and during maturation," J. Neurochem., 1971, 18(6):1163-1165.

Puyana and Pinsky, "Searching for non-invasive markers of tissue hypoxia," Crit. Care, 2007, 11:116-117.

Reiter and Tan, "Melatonin: a novel protective agent against oxidative injury of the ischemic/reperfused heart," Cardiovascular Res., 2003, 58:10-19.

Reiter et al., "Free radical-mediated molecular damage; mechanisms for the protective actions of melatonin in the central nervous system," Neuroprotective Agents, 5th Int'l Conf., Annals NY Acad. Sci., 2001, 939:200-215.

Reiter, "Melatonin and its metabolites: new findings regarding their production and their radical scavenging actions," Acta. Biochim. Pol., 54(1):1-9, Mar. 2007.

Rising and D'Alecy, "Hypoxia-induced increases in hypoxic tolerance augmented by β-hydroxybutyrate in mice," Stroke, 1989, 20(9):1219-1225.

Robinson et al., "Physiological roles of ketone bodies as substrates and signals in mammalian tissues," Physiol. Rev. 60(1):143-187, Jan. 1980.

Rothstein et al., "β-lactam antibiotics offer neuroprotection by increasing glutamate transporter expression," Nature, 2005, 433(7021):73-77.

Russeth et al., "Identification of proteins from non-model organisms using mass spectometry: Application to a hibernating mammal," J. Proteome Res., 2006, 5(4):829-839.

Schmelzer et al., "A comparison of central venous and arterial base deficit as a predictor of survival in acute trauma," Am. J. Emerg. Med., 2008, 26:119-123.

Schmickle, "Feeling like you want to hibernate? Scientists say its in your genes," Star Tribune, 2003, [retrieved on Oct. 14, 2003]. Retrieved from the Internet: <URL: http://www.startribune.com/stories/462/4150245.html>, 4 pages.

Seifman et al., "Endogenous melatonin increases in cerebrospinal fluid of patients after severe traumatic brain injury and correlates with oxidative stress and metabolic disarray," Journal of Cerebral Blood Flow & Metabolism, 2008, 28:684-696.

Sigma Aldrich (Melatonin. Sigma Prod. No. M5250, 1 page, 1997.

Sinha et al., "Effect of melatonin on ischemia reperfusion injury induced by middle cerebral artery occlusion in rats," Eur. J. Pharmacol., 2001, 428:185-192.

Skarda et al., "Comparison of prolonged hypotensive and normotensive resuscitation strategies in a porcine model of hemorrhagic shock," J. Am. Coll. Surg., 2006, 203(3S):S32-S33.

Skarda et al., "Increased poly(ADP-ribose) polymerase activity during porcine hemorrhagic shock is transient and predictive of mortality," Resuscitation, 2007, 75(1):135-144.

Smith et al., "KTX 0101: a powerful metabolic approach to cytoprotection in major surgery and neurological disorders," CNS Drug Rev., 2005, 11(2):113-140.

Squire et al., "Pancreatic triacylglycerol lipase in a hibernating mammal. II. Cold-adapted function and differential expression," Physiol. Genomics, 2003, 16(1):131-140.

Srere et al., "Central role for differential gene expression in mammalian hibernation," Proc. Natl. Acad. Sci. USA, 1992, 89(15):7119-7123.

Suzuki et al., "Effect of β-hydroxybutyrate, a cerebral function improving agent, on cerebral hypoxia, anoxia and ischemia in mice and rats," Jpn. J. Pharmacol., 2001, 87(2):143-150.

Suzuki et al., "β-hydroxybutyrate, a cerebral function improving agent, protects rat brain against ischemic damage caused by permanent and transient focal cerebral ischemia," Jpn. J. Pharmacol., 2002, 89(1):36-43.

Tan et al., "Physiological ischemia/reperfusion phenomena and their relation to endogenous melatonin production," Endocrine, 2005, 27:149-157.

Taylor et al., "Phosphomonoesters predict early mortality in porcine hemorrhagic shock," J. Trauma, 2004, 56(2):251-258.

Taylor et al., "Tissue Energetics as Measured by Nuclear Magnetic Resonance Spectroscopy During Hemorrhagic Shock," Shock, 2004, 21(1):58-64.

Taylor et al., "Use of near-infrared spectroscopy in early determination of irreversible hemorrhagic shock," J. Trauma, 2005, 58(6):1119-1125.

Tildon et al., "Coenzyme A transferase activity in rat brain," Biochem. Biophys. Res. Commun., 1971, 43(1):225-231.

(56) References Cited

OTHER PUBLICATIONS

Tisherman, "Suspended animation for resuscitation from exsanguinating hemorrhage," Crit Care Med., 2004, 32(2) (Suppl.):S46-S50.
Van der Auwera et al., "A ketogenic diet reduces amyloid β 40 and 42 in a mouse model of Alzheimer's disease," Nutrition and Metabolism, 2005, 2:28-35.
Vanitallie and Nufert, "Ketones: metabolism's ugly duckling," Nutr. Rev., 2003, 61(10):327-341.
Veech et al., "Ketone bodies, potential therapeutic uses," IUBMB Life, 2001, 51(4):241-247.
Wichmann et al., "Melatonin administration attenuates depressed immune functions after trauma-hemorrhage," J. Surgical Res., 1996, 63:256-262.
Williamson et al., "Activities of enzymes involved in acetoacetate utilization in adult mammalian tissues," Biochem J., 1971, 121(1):41-47.
Wolf et al., "D-β-Hydroxybutyrate and melatonin for treatment of porcine hemorrhagic shock and injury: a melatonin dose-ranging study," BMC Res. Notes, 10(1):649, Nov. 2017.
Wolf et al., "Safety of D-β-Hydroxybutyrate and Melatonin for the Treatment of Hemorrhagic Shock With Polytrauma," Shock., Aug. 2015, 44 Suppl. 1:79-89.
Zenker et al., "Thresholded area over the curve of spectrometric tissue oxygen saturation as an indicator of volume resuscitability in porcine hemorrhagic shock," J. Trauma, 2007, 63:573-580.
Zhang et al., "Developmental regulation of D-beta-hydroxybutyrate dehydrogenase in rat liver and brain," FEBS Lett., 1989, 256(1-2):71-74.

\* cited by examiner

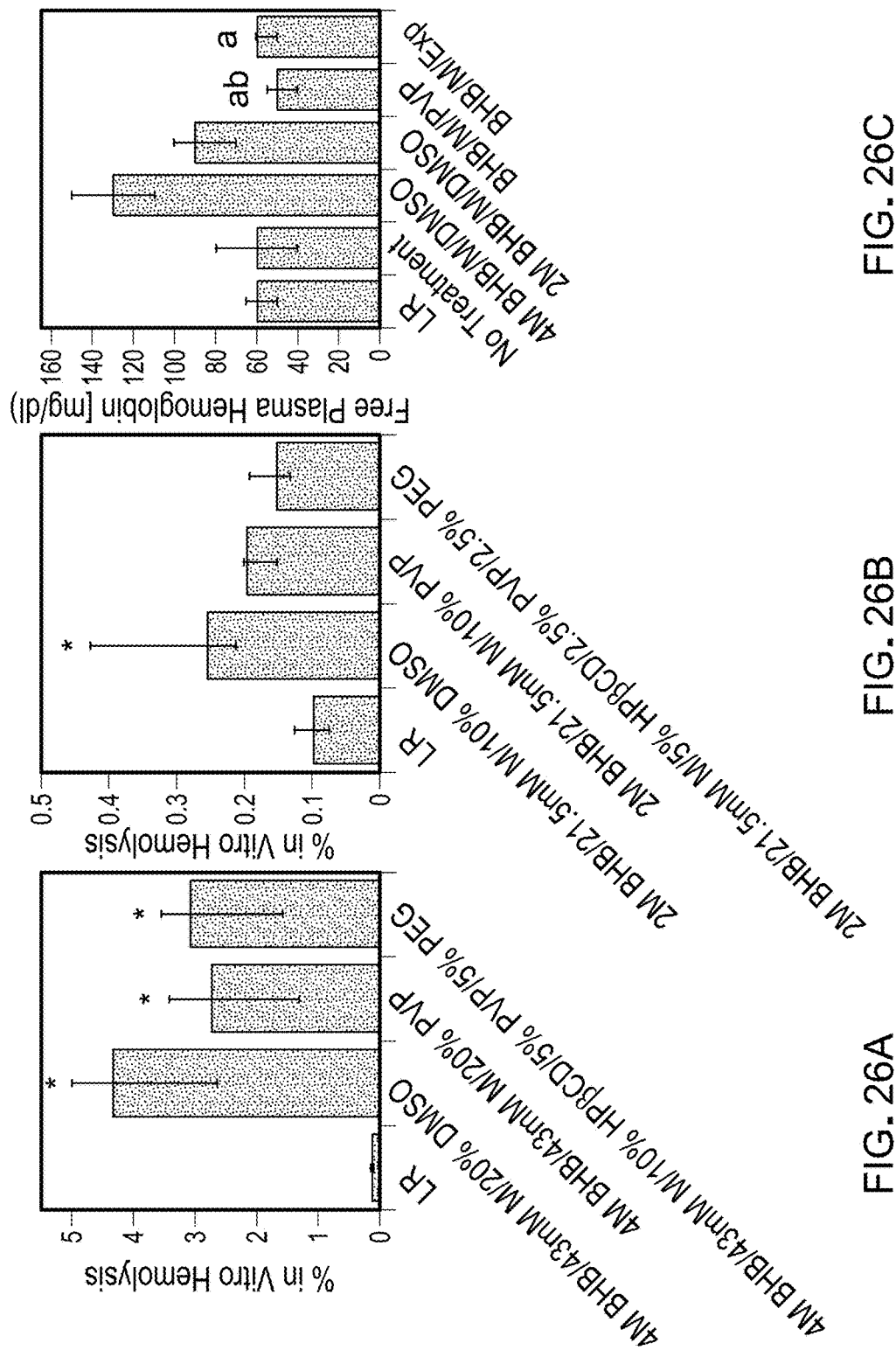

RESUSCITATION COMPOSITION AND METHODS OF MAKING AND USING

CROSS REFERENCE TO RELATED APPLICATIONS

This application claims the benefit of priority under 35 U.S.C. § 119(e) to U.S. Application No. 62/397,211 filed Sep. 20, 2016.

FEDERALLY SPONSORED RESEARCH OR DEVELOPMENT

This invention was made with government support under 8UL1TR000114-02 awarded by the National Institutes of Health. The government has certain rights in the invention.

TECHNICAL FIELD

This disclosure generally relates to compositions and methods for treating blood loss due to a major hemorrhagic event.

BACKGROUND

Every three minutes, a person in the United States dies from trauma. Traumatic injuries are the leading cause of death in Americans between the ages of 1 and 44 and the leading cause of life years lost overall. Worldwide, more than 5 million people die from injuries every year.

Hemorrhage is the second leading cause of death after trauma. The main goals for treating severe blood loss are bleeding control and the restoration of lost blood volume. Blood loss often only can be interrupted via surgical repair. However, most deaths from hemorrhage occur within the first hours after injury, often before patients are able to reach a hospital. Consequently, experts regard hemorrhagic shock, the state induced by severe blood loss, as the leading cause of death that is preventable.

Thus, the development of a low-volume resuscitation composition that increases survival during the critical first hours of hemorrhagic shock would be highly desirable.

SUMMARY

There is a critical need for treatments that improve survival during the early phase of hemorrhagic shock. Such a treatment would allow more patients to reach the hospital and receive life-saving treatment. This disclosure provides a resuscitation composition and describes methods of making and using such a composition.

In one aspect, a resuscitation composition is provided. Such a resuscitation composition typically includes about 40 mM to 45 mM melatonin, about 3.8 M to about 4.2 M beta-hydroxybutyrate (BHB) or a pharmaceutically acceptable salt thereof in a solution of about 8% to about 12% hydroxypropyl-beta-cyclodextrin (HPbCD), about 4% to about 6% polyvinylpyrrolidone (PVP) and about 4% to about 6% polyethylene glycol (PEG).

In some embodiments, such a resuscitation composition includes about 43 mM melatonin. In some embodiments, such a resuscitation composition includes about 4.0 M BHB. In some embodiments, such a resuscitation composition includes about 10% HPbCD, 5% PVP, and 5% PEG.

A representative pharmaceutically acceptable salt of BHB is Na-BHB. In some embodiments, the composition is lyophilized. In some embodiments, the composition further includes a stabilizer.

In still another aspect, an article of manufacture comprising the resuscitation composition described herein.

In another aspect, a method for treating an individual who is experiencing or has experienced a major hemorrhagic event is provided. Such a method typically includes administering the resuscitation composition described herein to the individual.

In some embodiments, the resuscitation composition is administered to the individual before the individual has lost about 10% blood volume (e.g., about 20% blood volume, about 30% blood volume).

In some embodiments, the blood loss in the individual results in a systolic blood pressure of about 70 mm Hg or less. In some embodiments, the resuscitation composition is administered at a volume of about 0.1 to about 5 milliliters (mls) per kilogram (kg) of weight of the individual. In some embodiments, the resuscitation composition is administered at a volume of about 0.1 to about 5 mLs per kg of weight of the individual per hour. In some embodiments, the composition is administered intravenously or intraosseously. In some embodiments, such a method further includes transfusing the individual with blood or plasma.

In another aspect, a method of making a resuscitation composition is provided. Such a method typically includes solubilizing melatonin or a metabolite, precursor or analog thereof in a solvent comprising HPbCD, PEG, and PVP; lyophilizing the solubilized melatonin; and adding BHB to the lyophilized, solubilized melatonin. In some embodiments, such a method can further include adjusting the pH to between about 6 and about 8. In some embodiments, such a method can further include resuspending the BHB or the lyophilized, solubilized melatonin and BHB in an aqueous solvent.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part I—Evaluation of Melatonin

$$CE = S_0 k_{1:1} = \frac{\text{Slope}}{(1 - \text{Slope})}$$

where So is the intrinsic substrate solubility and $k_{1:1}$ stability constant of the complex. Since the slope of the phase solubility diagram (plot of molar concentration of MLT vs PVP (in terms of monomer)) was 0.030, the CE was calculated to be 0.031. The MLT:PVP molar ratio was calculated to be 1:33 using the following equation:

$$\text{Molar ratio} = 1 : \frac{(CE + 1)}{CE}$$

Figure 16:
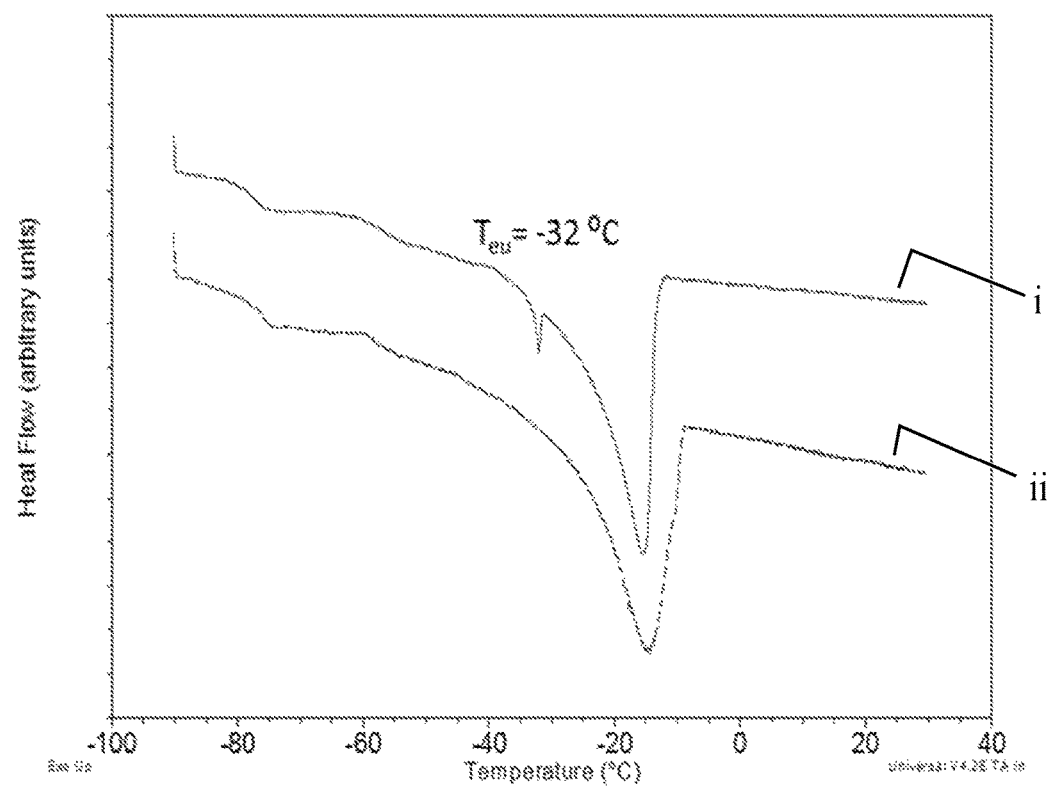

FIG. 16 is a graph showing the DSC heating curves of frozen pre-lyophilization solution containing BHB (line i) and BHB-MLT-PVP (line ii). The solutions were cooled from RT to −90° C. at 1° C./min, held for 30 min and heated to 25° C. at 0.1° C./min. Only the heating curves are shown. Solute crystallization in frozen BHB solution is evident from the endotherm at −32° C.

Figure 17:
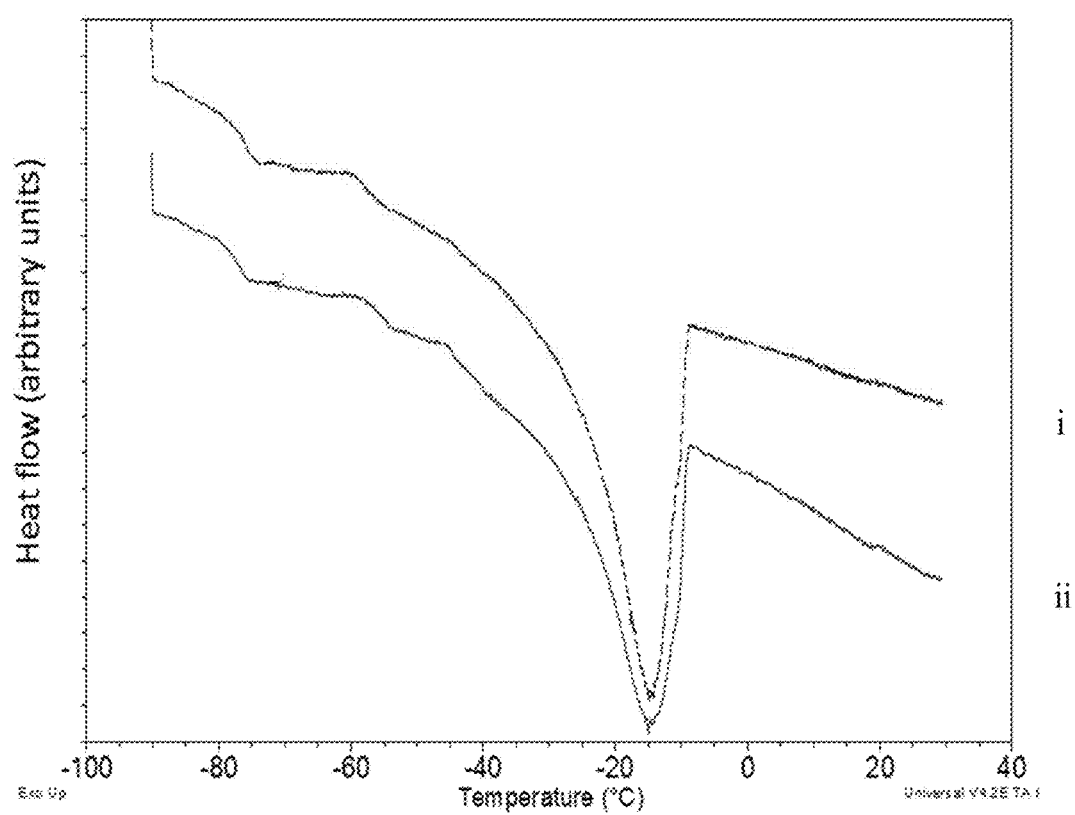

FIG. 17 is a graph showing the DSC heating curve of frozen pre-lyo solutions of BHB-MLT-PVP. Each solution was cooled from RT to −90° C. at 1° C./min, held for 30 min and heated to 25° C. at 1° C./min. Only heating curves are shown. For line ii, the frozen solution was heated to the annealing temperature (−35° C.; 1° C./min), annealed for 12 h, cooled back to −90° C. at 1° C./min and heated to RT at 1° C./min. Only final heating curve is shown.

Figure 18:
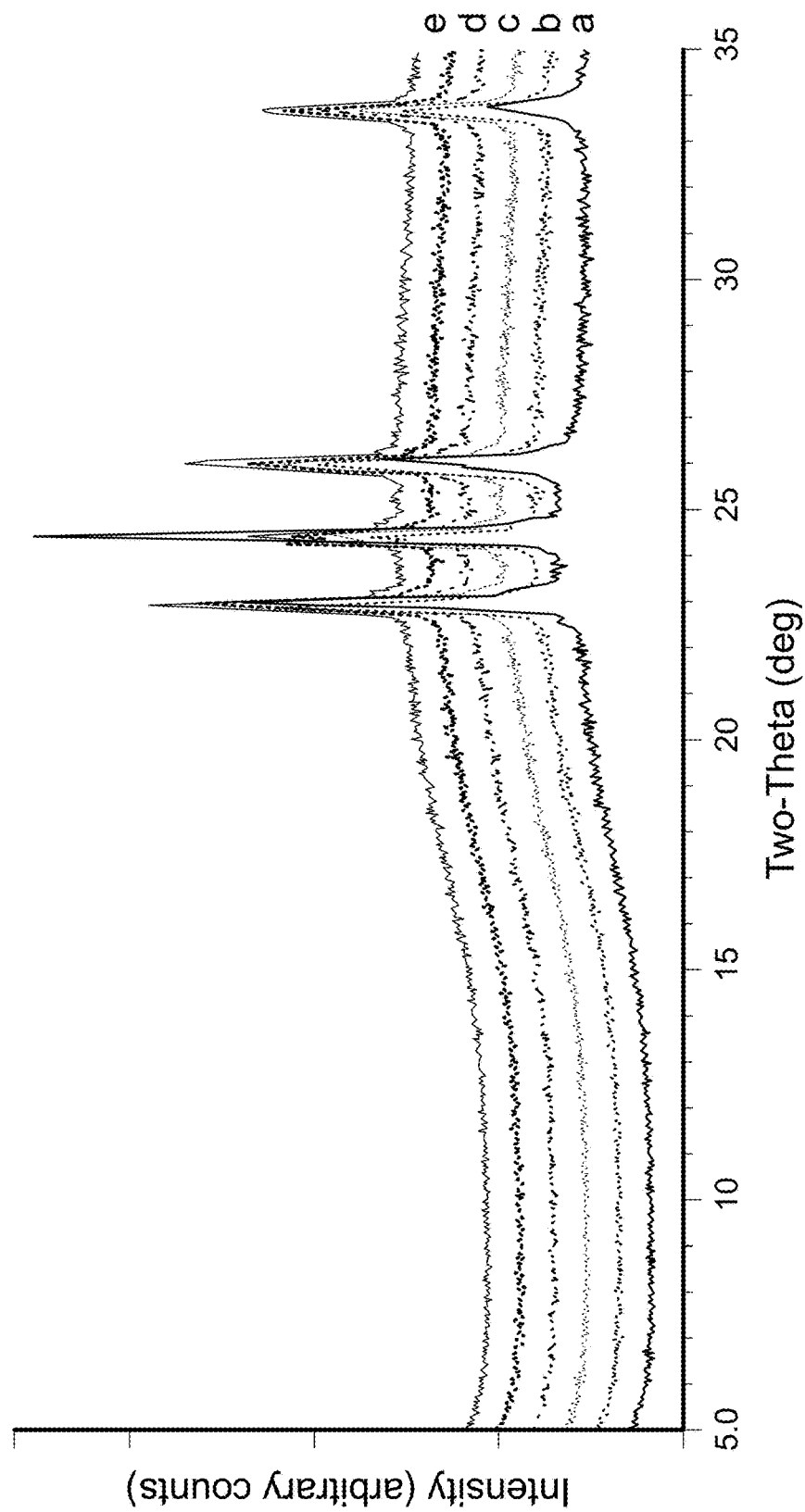

FIG. 18 shows the overlaid XRD patterns of frozen BHB MLT PVP solution. The solution was cooled to −60° C. at 1° C./min, held for 1 hour, heated to −35° C. at 1° C./min and held for 5 hours. (a) XRD pattern at −60° C. after 1 hour; (b) to (e) XRD patterns at −35° C. every hour up to 5 hours. All the peaks in the patterns can be attributed to ice.

Part II—Resuscitation Composition

Figure 19A:
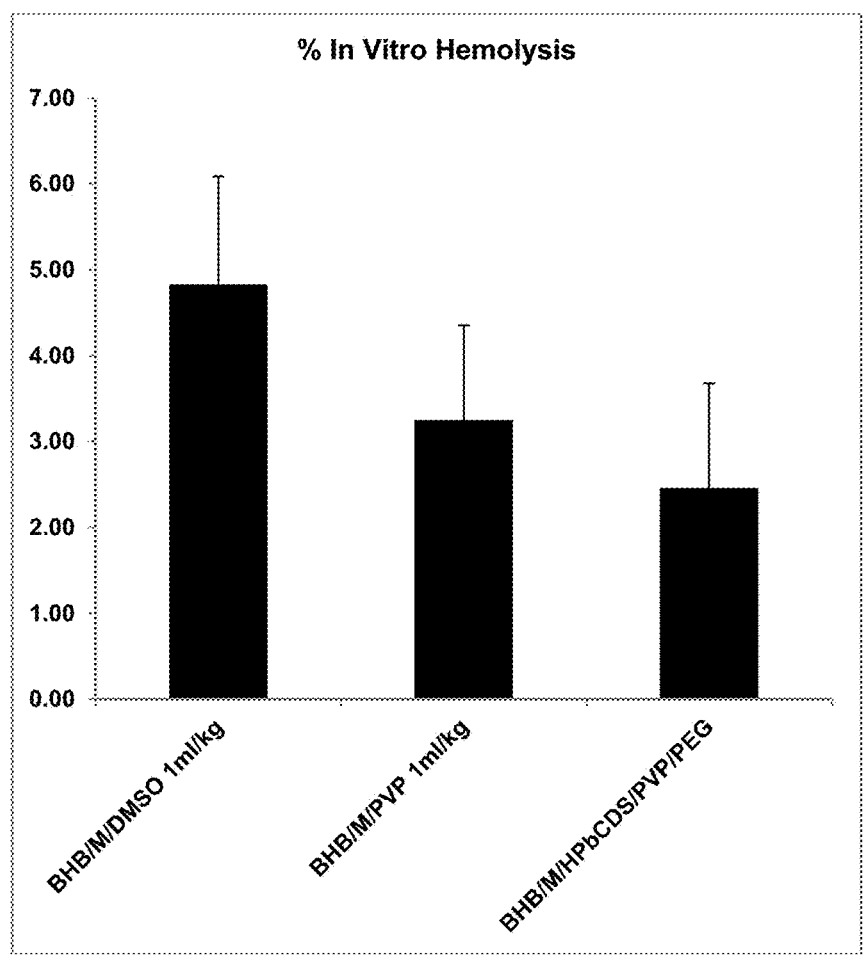

FIG. 19A is a graph showing the percent in vitro hemolysis of BMB/M compositions in DMSO (left), PVP (middle) or HPbCD/PVP/PEG (right) at 1 ml/kg.

Figure 19B:
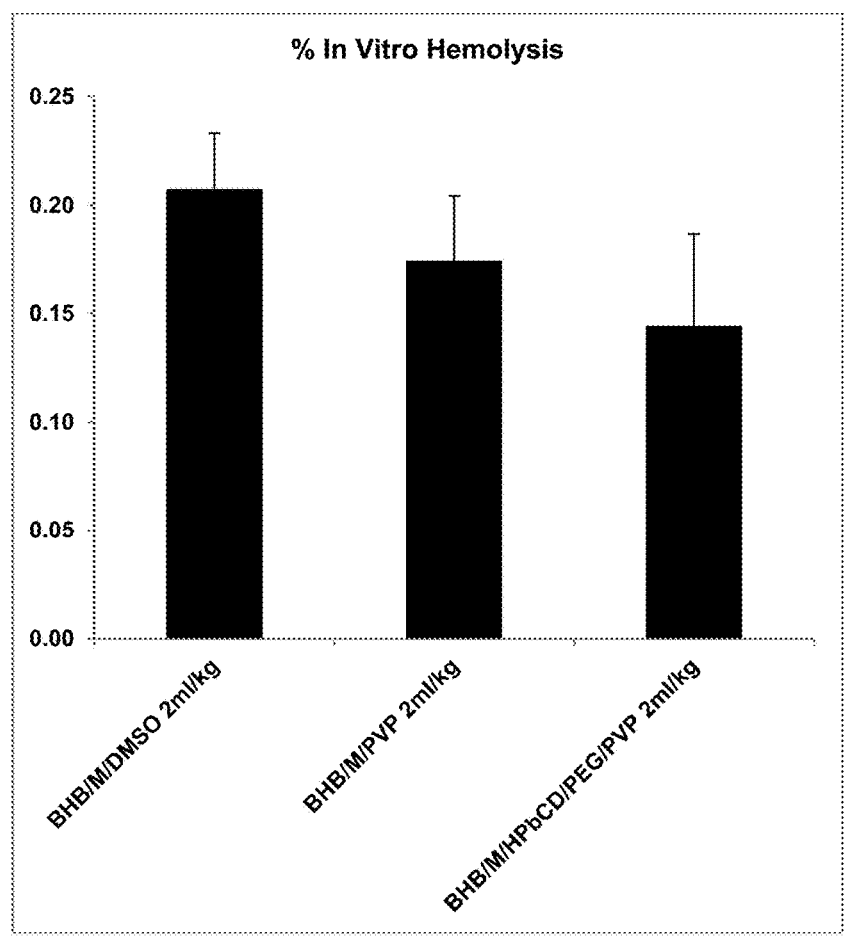

FIG. 19B is a graph showing the percent in vitro hemolysis of BMB/M compositions in DMSO (left), PVP (middle) or HPbCD/PVP/PEG (right) at 2 ml/kg.

Figure 20:
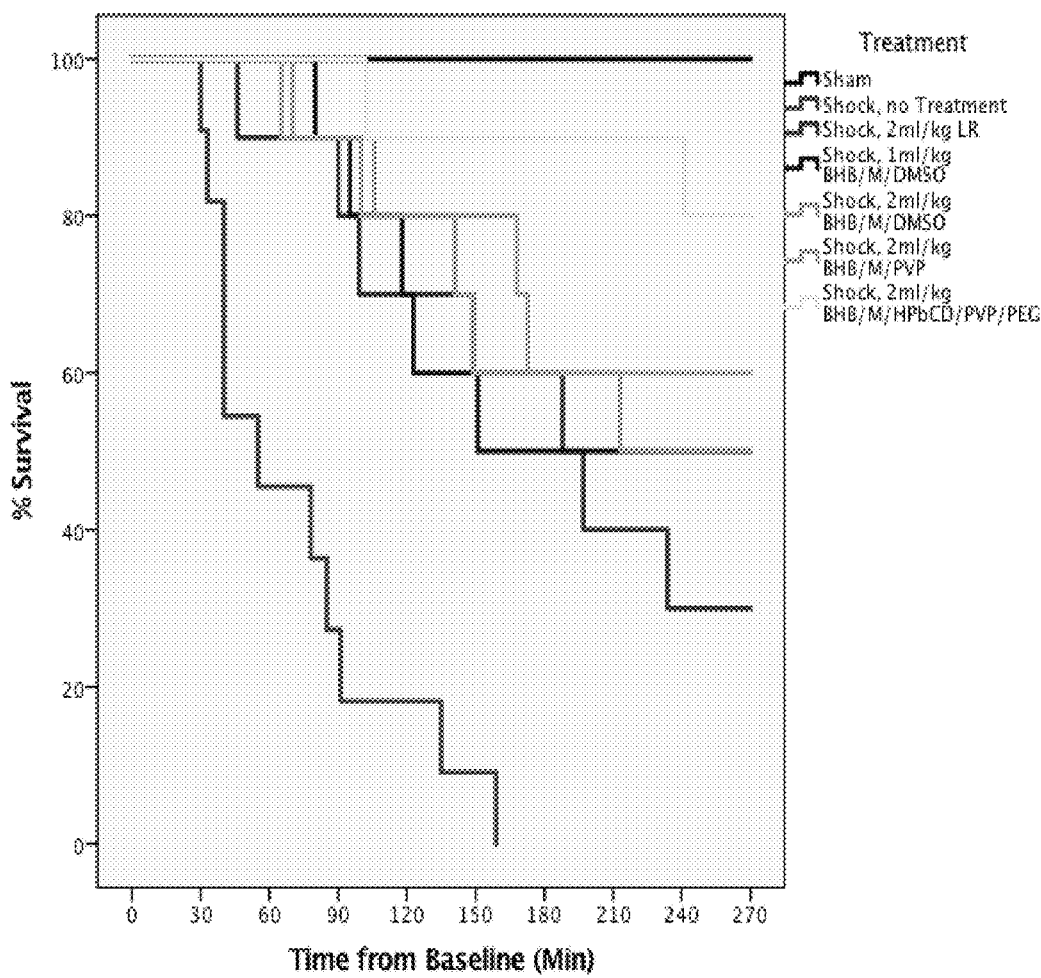

FIG. 20 is a graph showing the efficacy of the prototype solutions tested in a rat model of acute blood loss.

Figure 21:
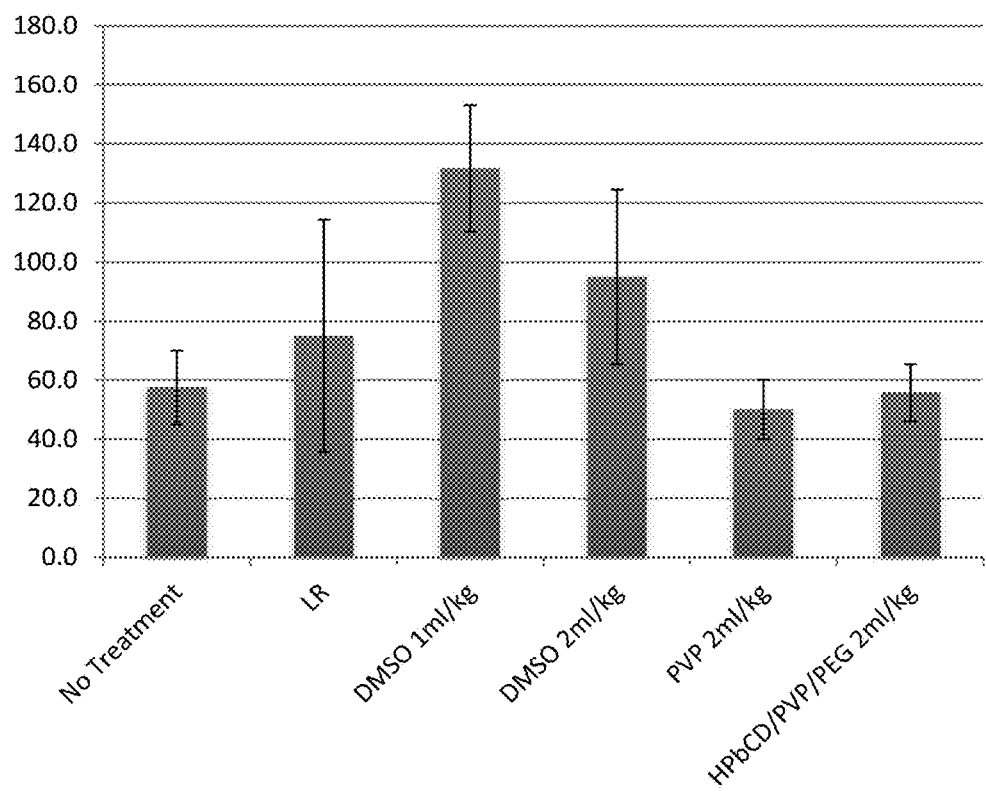

FIG. 21 is a graph showing the amount of in vivo hemolysis using free plasma hemoglobin.

Figure 22:
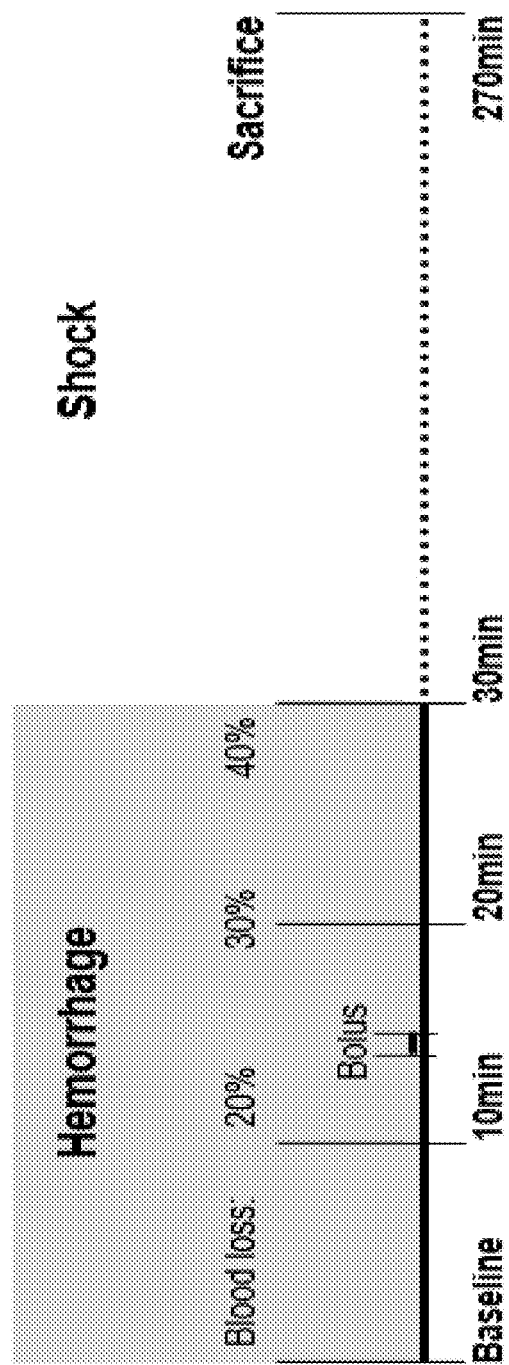

FIG. 22 shows the hemorrhagic shock and infusion protocol. Treatment solutions were administered as a 1 ml/kg or 2 ml/kg bolus over 1 min.

Figures 23A, 23B:
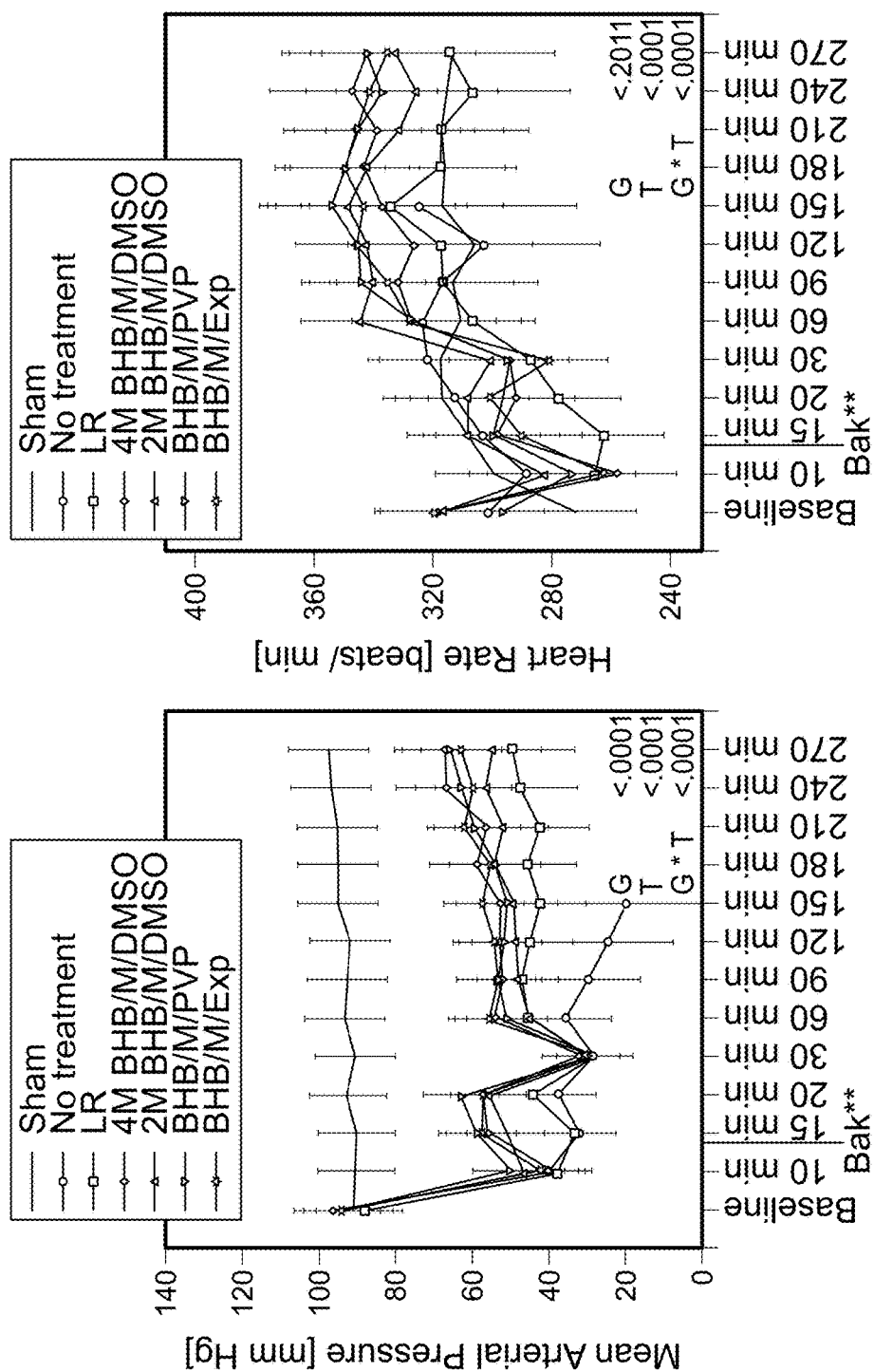

FIG. 23A is a graph showing Mean arterial pressure in rats exposed to 40% blood loss and treated with LR or different formulations of BHB/M. Data are presented as means with 95% confidence intervals. BHB D-β-hydroxybutyrate, DMSO dimethyl sulfoxide, G group effect, G*T group*time interaction effect, LR lactated Ringer's solution, M melatonin, PVP polyvinylpyrrolidone K12, T time effect, BHB/M/Exp refers to the BHB/M/HpbCD/PVP/PEG formulation.

FIG. 23B is a graph showing heart rate in rats exposed to 40% blood loss and treated with LR or different formulations of BHB/M. Data are presented as means with 95% confidence intervals. BHB D-β-hydroxybutyrate, DMSO dimethyl sulfoxide, G group effect, G*T group*time interaction effect, LR lactated Ringer's solution, M melatonin, PVP polyvinylpyrrolidone K12, T time effect, BHB/M/Exp refers to the BHB/M/HpbCD/PVP/PEG formulation.

Figure 24:
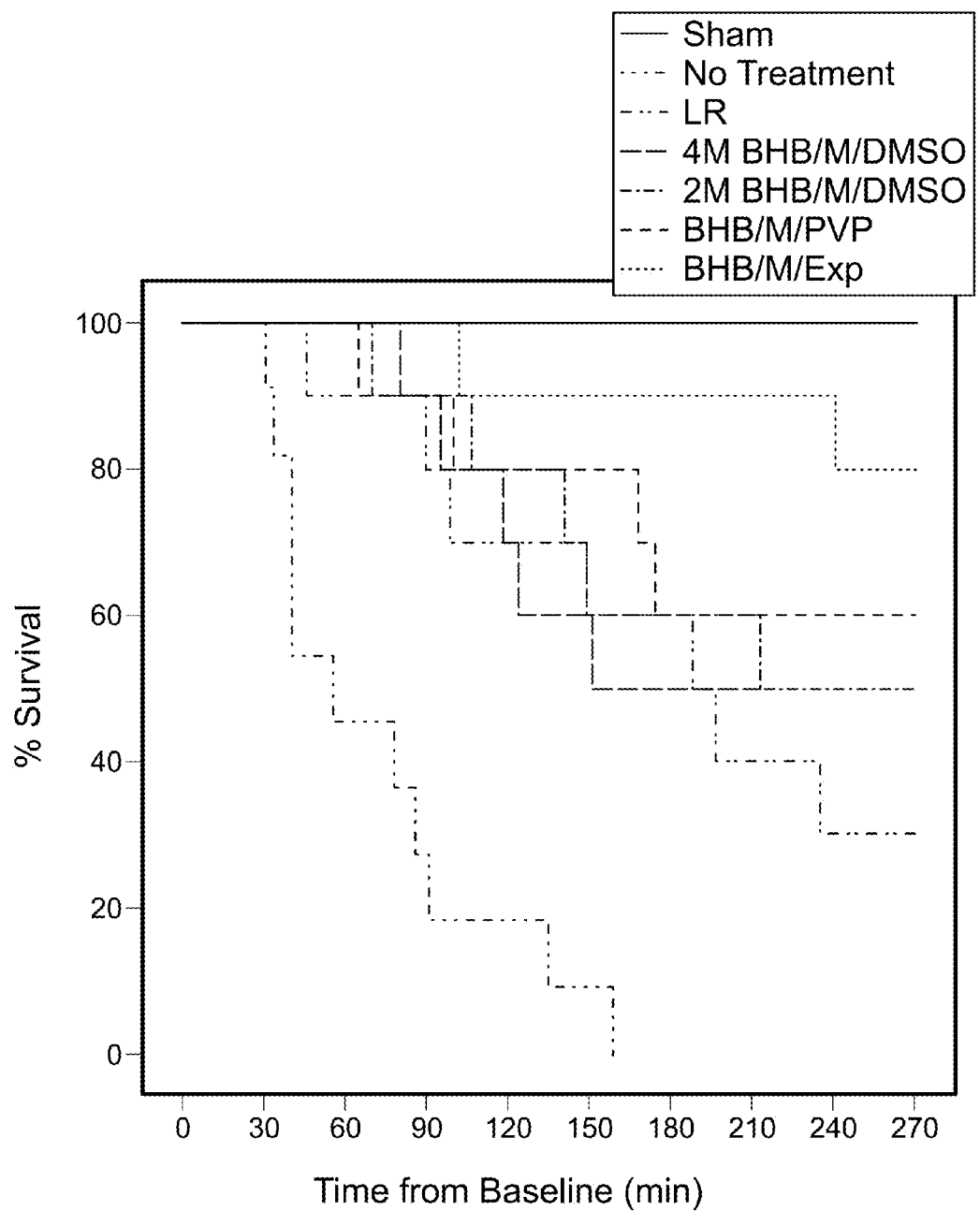

FIG. 24 is a Kaplan-Meier survival curve of rats exposed to 40% blood loss and treated with LR or different formulations of BHB/M. BHB D-β-hydroxybutyrate, DMSO dimethyl sulfoxide, LR lactated Ringer's solution, M melatonin, PVP polyvinylpyrrolidone K12.

Figure 25A:
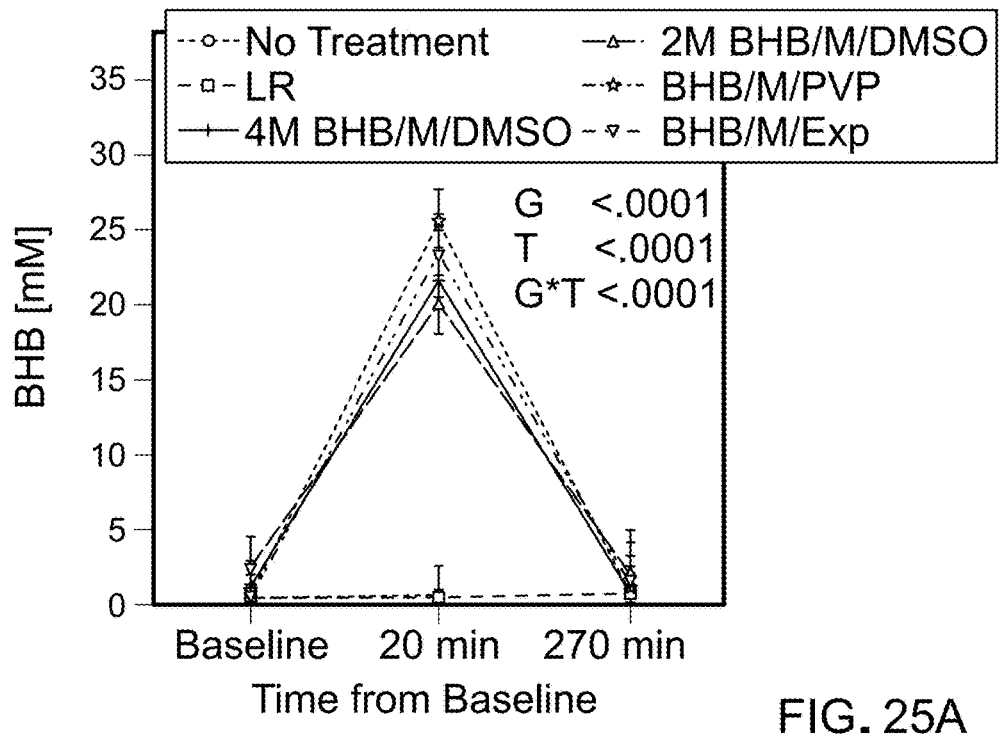

FIG. 25A is a graph showing serum concentrations of BHB in rats exposed to 40% blood loss and treated with LR or different formulations of BHB/M. Data are presented as means with 95% confidence intervals. BHB D-β-hydroxybutyrate, DMSO dimethyl sulfoxide, G group effect, G*T group*time interaction effect, LR lactated Ringer's solution, M melatonin, PVP polyvinylpyrrolidone K12, T time effect.

Figure 25B:
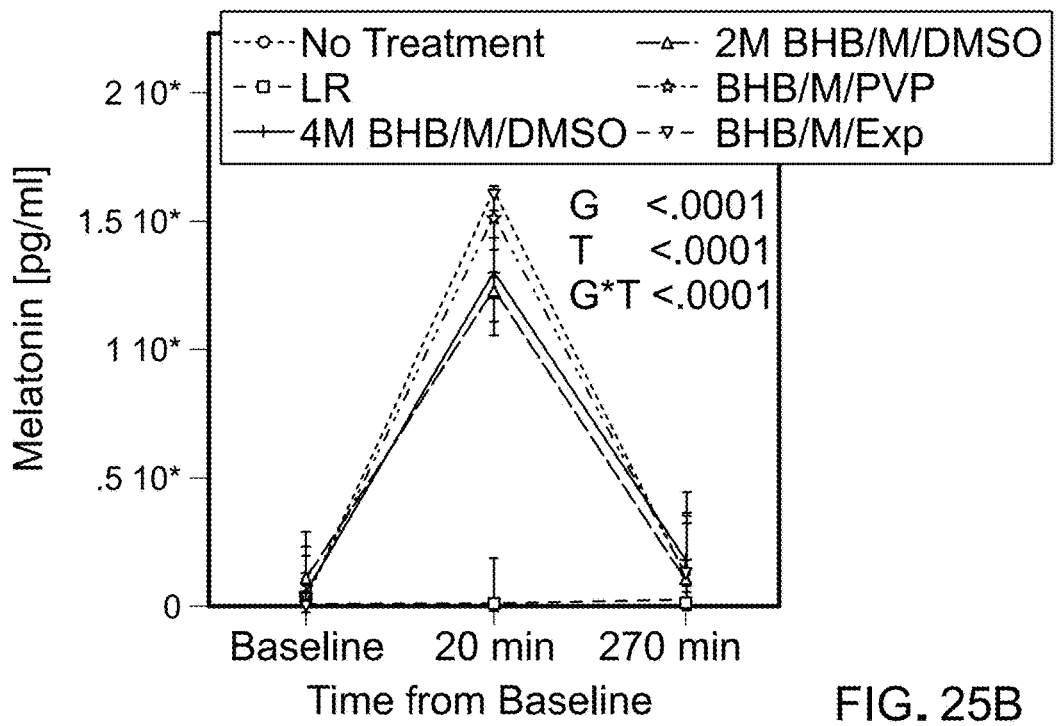

FIG. 25B is a graph showing serum concentrations of melatonin in rats exposed to 40% blood loss and treated with LR or different formulations of BHB/M. Data are presented as means with 95% confidence intervals. BHB D-β-hydroxybutyrate, DMSO dimethyl sulfoxide, G group effect, G*T group*time interaction effect, LR lactated Ringer's solution, M melatonin, PVP polyvinylpyrrolidone K12, T time effect.

FIG. 26A is a graph showing in vitro hemolysis-induction by LR and different formulations of BHB/M. In vitro hemolysis was calculated as described herein. Data are presented as medians with interquartile range. *p<0.05 vs LR. BHB D-β-hydroxybutyrate, DMSO dimethyl sulfoxide, HPβCD hydroxypropyl-β-cyclodextrin, LR lactated Ringer's solution, M melatonin, PEG polyethylene glycol 400, PVP polyvinylpyrrolidone K12.

FIG. 26B is a graph showing in vitro hemolysis-induction by LR and different formulations of BHB/M. In vitro hemolysis was calculated as described herein. Data are presented as medians with interquartile range. *p<0.05 vs LR. BHB D-β-hydroxybutyrate, DMSO dimethyl sulfoxide, HPfβCD hydroxypropyl-β-cyclodextrin, LR lactated Ringer's solution, M melatonin, PEG polyethylene glycol 400, PVP polyvinylpyrrolidone K12.

FIG. 26C is a graph showing in vivo hemolysis-induction by LR and different formulations of BHB/M. Free plasma hemoglobin was analyzed as a marker of in vivo hemolysis. Data are presented as medians with interquartile range. a p<0.0.5 vs 4M BHB/43 mM M/20% DMSO, b p<0.05 vs 2M BHB/21.5mM M/10% DMSO. BHB D-β-hydroxybutyrate, DMSO dimethyl sulfoxide, HPfβCD hydroxypropyl-β-cyclodextrin, LR lactated Ringer's solution, M melatonin, PEG polyethylene glycol 400, PVP polyvinylpyrrolidone K12.

Figure 27:
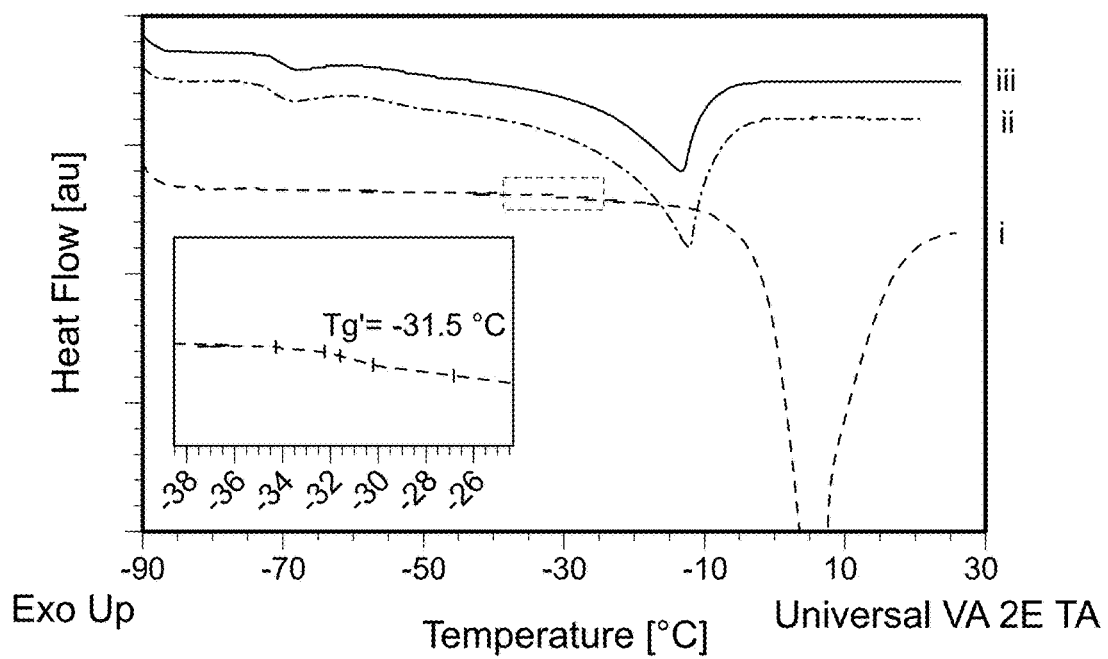

FIG. 27 are graphs showing DSC heating curves of frozen aqueous solutions of: M/Exp (line i), BHB/M/Exp (line ii) and 2M BHB (line iii) solution. A select region has been expanded to enable visualization of glass transition of MLT-Exp freeze-concentrate (Tg'). The midpoint of Tg' is reported. BHB D-β-hydroxybutyrate, M melatonin, Tg' glass transition temperature.

Figure 28:
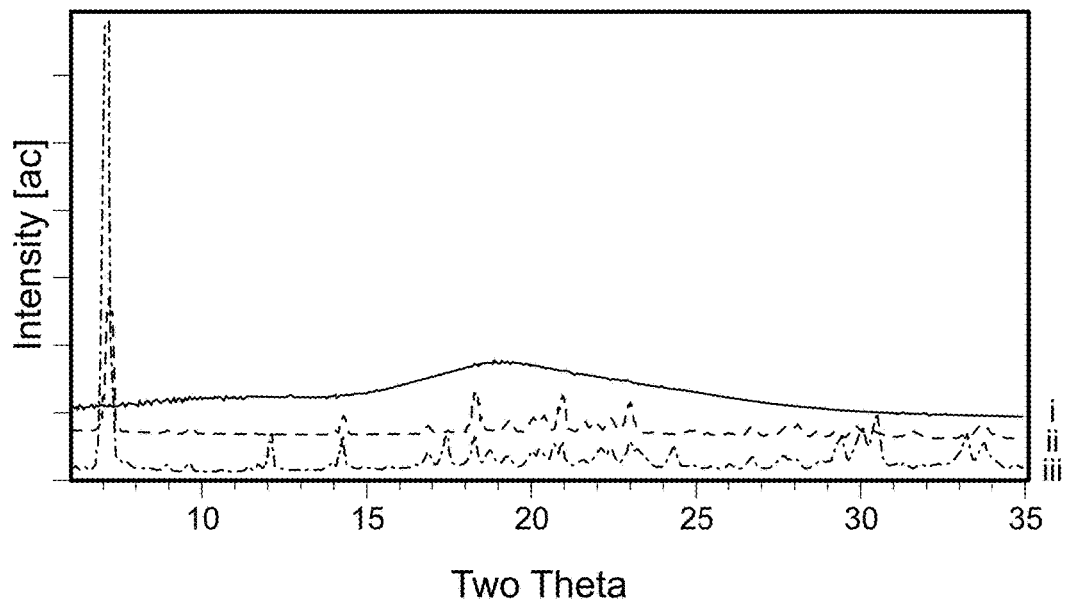

FIG. 28 are graphs showing XRD patterns of M/Exp lyophile (line i) BHB/M/Exp lyophile (line ii) and BHB 'as is' (line iii). BHB D-β-hydroxybutyrate, M melatonin.

Figure 29:
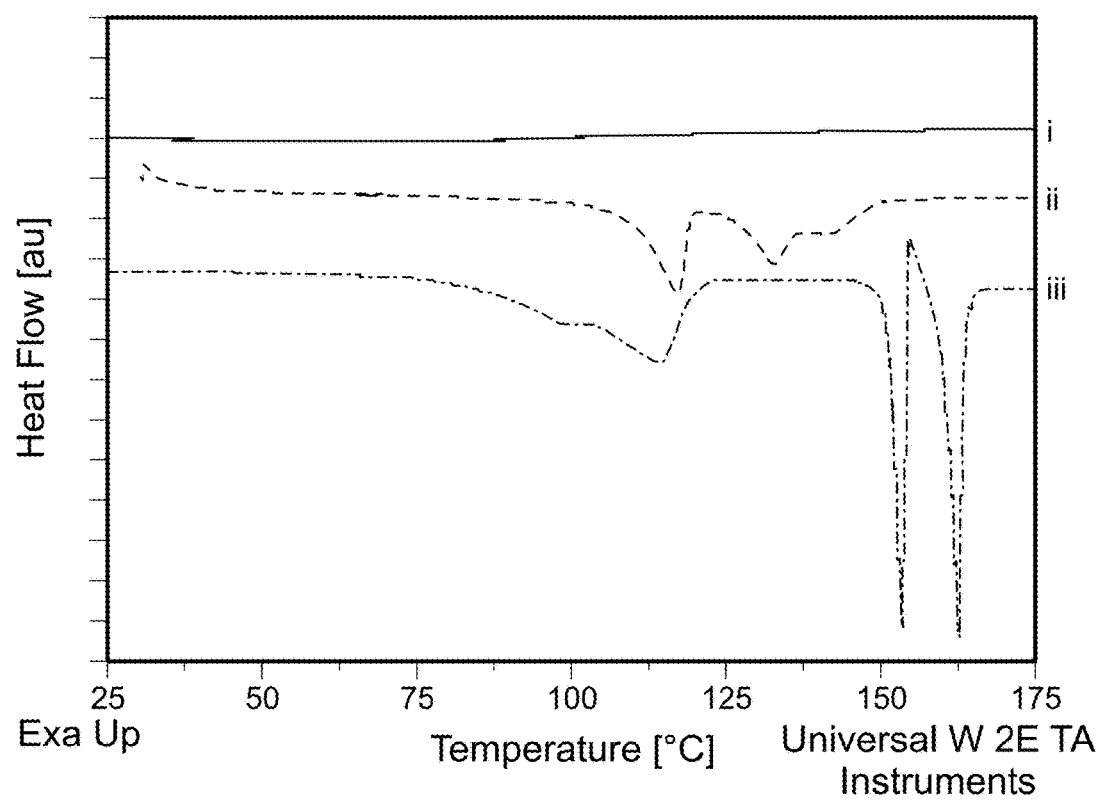

FIG. 29 are graphs showing DSC heating curves of M/Exp lyophile (line i) BHB/M/Exp lyophile (line ii) and BHB 'as is' (line iii). BHB D-β-hydroxybutyrate, M melatonin.

DETAILED DESCRIPTION

There is significant need for treatments that prevent mortality after trauma and blood loss. A composition that includes melatonin (M) and D-beta-hydroxybutyrate (BHB) has been shown to increase survival in preclinical models of hemorrhagic shock and trauma. See, for example, U.S. Pat. Nos. 8,728,532 and 9,149,450; Klein et al. (2010, Shock, 34:565-72) and Mulier et al. (2012, Resuscitation, 83:253-8). Infusion with BHB/M did not cause adverse effects or signs of organ damage in this preclinical model of hemorrhagic shock (see, for example, Wolf et al., 2015, Shock, 44 Supplem 1:79-89). The formulation used in those preclinical models, however, included dimethylsulfoxide (DMSO) to solubilize the melatonin. In the preclinical models, the DMSO was used at a level that is acceptable for use in animals, but DMSO has an unknown safety profile in humans due, at least, to the possibility of hemolysis. Therefore, it was desirable to develop a formulation that is able to increase survival but contains only components that have established clinical safety profiles.

In addition, the formulation used in the preclinical models required a three-step reconstitution process, which would make it difficult to use in certain environments. Therefore, it was also desirable to generate solid dosage forms that were more easily reconstituted than the formulation used in the preclinical models.

The resulting compositions are referred to herein as "resuscitation compositions" or "low-volume resuscitation compositions" due to the ability of these compositions to resuscitate animals who are experiencing or have experienced a significant loss of blood. This disclosure describes such resuscitation compositions, and demonstrates the safety and efficacy of such resuscitation compositions in an animal model of hemorrhagic shock.

Melatonin, Metabolites, Immediate Precursors, or Analogs Thereof

Melatonin (5-methoxy-N-acetyltryptamine) is a hormone that is naturally synthesized from the amino acid tryptophan via synthesis from serotonin, and is well known for its involvement in the circadian rhythm (sleep-wake patterns). Melatonin acts as a broad-spectrum antioxidant and exhibits receptor-independent free radical scavenging activity. The free radical scavenging capacity of melatonin extends to its secondary, tertiary and quaternary metabolites, such that the interaction of melatonin with reactive oxygen and nitrogen species is a prolonged and cascade-type process that involves many of its metabolites. Therefore, metabolites, immediate precursors, or analogs of melatonin (or combinations thereof) also can be used in a resuscitation composition as described herein.

Representative metabolites of melatonin include, without limitation, 6-hydroxy-melatonin (6-HMEL), 6-sulphatoxy-melatonin (aMT6s), $N^1$-acetyl-$N^2$-formyl-5-methoxy kynuramine (AFMK), $N^1$-acetyl-5-methoxy kynuramine (AMK), and 3-hydroxymelatonin (3-HMEL) Representative immediate precursors of melatonin include, without limitation, e.g., N-acetyl serotonin, 5-hydroxytryptamine, 5-hydroxytryptophan, or L-tryptophan. Representative analogs of melatonin include, without limitation, 2-chloromelatonin, 6-fluoromelatonin, 6-chloromelatonin, 6-hydroxymelatonin, N-isobutanoyl 5-methoxytryptamine, N-valeroyl 5-methoxytryptamine, 6-methoxymelatonin, 5-methyl N-acetyltryptamine, 5-benzoyl N-acetyltryptamine, O-acetyl 5-methoxytryptamine, N-acetyltryptamine, N-acetyl 5-hydroxytryptamine, and 5-methoxytryptamine. As indicated herein, reference to melatonin or melatonin metabolites, precursors or analogs should be understood to encompass salt forms, unless stated otherwise.

Melatonin or metabolites, immediate precursors, or analogs thereof can be obtained commercially from a number of companies such as, for example, Sigma Chemical Co. (St. Louis, Mo.).

Beta-Hydroxybutyrate or a Pharmaceutically Acceptable Salt Thereof

Beta-hydroxybutyrate is formed by the reversible reduction of acetoacetate, which is formed from acetyl CoA. Physiologically, the ratio of hydroxybutyrate to acetoacetate depends upon the NADH/NAD+ ratio inside the cell. As used herein, beta-hydroxybutyric acid includes a pharmaceutically acceptable salt thereof. The term "pharmaceutically acceptable salt" refers to salts that possess toxicity profiles within a range that affords utility in pharmaceutical applications. Unless clearly indicated otherwise, reference in the specification to beta-hydroxybutyrate should be understood as encompassing salt forms of the compound, whether or not this is explicitly stated.

Suitable pharmaceutically acceptable acid-addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4 hydroxybenzoic, phenylacetic, mandelic, embonic (pamoic), methanesulfonic, ethanesulfonic, benzenesulfonic, pantothenic, trifluoromethanesulfonic, 2 hydroxyethanesulfonic, p toluenesulfonic, sulfanilic, cyclohexylaminosulfonic, stearic, alginic, β hydroxybutyric, salicylic, galactaric and galacturonic acid.

Suitable pharmaceutically acceptable base-addition salts include, for example, metallic salts including alkali metal, alkaline earth metal and transition metal salts such as, for example, calcium, magnesium, potassium, sodium and zinc salts. Pharmaceutically acceptable base-addition salts also include organic salts made from basic amines such as, for example, N,N' dibenzylethylenediamine, chloroprocaine, choline, diethanolamine, ethylenediamine, meglumine (N methylglucamine) and procaine.

Any of these salts may be prepared by conventional means from beta-hydroxybutyrate by reacting, for example, the appropriate acid or base with beta-hydroxybutyrate. In some embodiments, the salts are in crystalline form, and can be prepared by crystallization of the salt from a suitable solvent. A person skilled in the art will know how to prepare and select suitable salt forms. See, for example, *Handbook of Pharmaceutical Salts: Properties, Selection, and Use* By P. H. Stahl and C. G. Wermuth (Wiley-VCH 2002).

The salt of beta-hydroxybutyric acid may be preferred in a resuscitation composition, as a composition that includes the salt will be closer to a physiologically acceptable pH than when the acid is used. A suitable salt of beta-hydroxybutyric acid for use in an ischemia/reperfusion protection composition is the sodium salt of beta-hydroxybutyrate (i.e., Na-beta hydroxybutyrate), but other salts of beta-hydroxybutyrate can be used, alone or in combination with Na-beta hydroxybutyrate, to decrease or otherwise control the salt load. Beta-hydroxybutyric acid (or pharmaceutically acceptable salts thereof) can be obtained commercially from a number of companies such as, for example, Sigma Chemical Co. (St. Louis, Mo.). It is noted that the 'D' stereoisomer of beta-hydroxybutyrate, sometimes referred to as the 'R' stereoisomer, may be preferred in a resuscitation composition described herein as opposed to the 'L' stereoisomer, since the 'D' stereoisomer is the isomer that is synthesized in humans.

Optimized Solvent for Resuscitation Composition

Cyclodextrin molecules are relatively large, with a molecular weight ranging from almost 1000 to greater than 2000 Da. Cyclodextrin molecules possess a large number of hydrogen donors and acceptors, which result in poor absorption through biological membranes. Cyclodextrins are non-reducing cyclic glucose oligosaccharides resulting from the cyclomaltodextrin glucanotransferase (EC 2.4.1.19; CGTase)-catalyzed degradation of starch. The most common cyclodextrins have six, seven or eight D-glucopyranonsyl residues (alpha-, beta-, and gamma-cyclodextrin, respectively) linked by an alpha-1,4 glycosidic bonds. Hydroxypropyl-beta-cyclodextrin (HPbCD) (CAS# 94035-02-6) is a partially substituted poly(hydroxpropyl) ether of beta cyclodextrin (bCD) having a formula of $(C_3H_7O)n$. HPbCD contains not less than 10.0 percent and not more than 45.0 percent hydroxypropoxy groups. The solubility of HPbCD exceeds 600 mg/ml, and viscosity is not an issue in concentrations below 55%.

Polyethylene glycol (PEG) (CAS# 24322-68-3) refers to an oligomer or polymer of ethylene oxide, typically having a molecular mass below 20,000 g/mol. Generally, PEGs are polydisperse molecules having a distribution of molecular weights. For a resuscitation composition as described herein, PEG200 up to PEG6000 (e.g., PEG200, PEG300, PEG400, PEG4000, PEG6000) can be used. It would be appreciated that the number indicates the average molecular weight of the PEG molecules (e.g., PEG having an average molecular weight of approximately 400 Daltons would be labeled PEG400). PEGs having different average molecular weights exhibit different physical properties (e.g. viscosity) due to chain length effects and, therefore, find use in different applications. The size distribution can be characterized statistically by its weight average molecular weight (Mw) and its number average molecular weight (Mn), the ratio of which is called the polydispersity index (Mw/Mn); Mw and Mn can be measured by mass spectrometry.

Polyvinylpyrrolidone (PVP) (CAS# 9003-39-8) is made from the monomer, N-vinylpyrrolidone, and is soluble in water and other polar solvents. PVP binds to polar molecules exceptionally well, owing to its polarity. PVP is approved by the FDA for many uses and is generally considered safe. For example and without limitation, PVP K12 or PVP K17 can be used in a resuscitation composition. It would be appreciated that forms of PVP that are typically used parenterally generally are preferred, but other forms of PVP (e.g., those that can be used orally; e.g., PVP K12-K90) also can be used in a resuscitation composition.

Methods of Making a Resuscitation Composition

A resuscitation composition as described herein can be formulated, for example, as a liquid resuscitation composition that is ready for use or as a dry powder (e.g., a lyophilized resuscitation composition) that requires dissolution or resuspension before use.

Whether formulated as a liquid or as a dry powder, it is desired that the final composition contain:

about 3.8 M to about 4.2 M BHB or pharmaceutically acceptable salt thereof (e.g., about 3.8 M to about 4.1 M, about 3.8 M to about 4.0 M, about 3.9 M to about 4.2 M, about 3.9 M to about 4.1 M, about 3.8 M, about 3.9 M, about 4.0 M, about 4.1 M, or about 4.2 M BHB);

about 40 mM to about 45 mM melatonin or metabolite, precursor or analog thereof (e.g., about 40 mM to about 44 mM, 40 mM to about 43 mM, 41 mM to about 44 mM, 41 mM to 43 mM, 42 mM to 44 mM, 42 mM to 43 mM, 40 mM, 42 mM, 43 mM, 44 mM, or 45 mM melatonin or metabolite, precursor or analog thereof);

about 8% to about 12% HPbCD (e.g., about 8% to about 11%, about 8% to about 10%, about 8% to about 9%, about 9% to about 12%, about 10% to about 12%, about 11% to about 12%, about 9% to about 11%, about 8%, about 9%, about 10%, about 11%, or about 12% HPbCD);

about 4% to about 6% PEG (e.g., about 4% to about 5%, about 5% to about 6%, about 4%, about 5%, or about 6% PEG); and about 4% to about 6% PVP (e.g., about 4% to about 5%, about 5% to about 6%, about 4%, about 5%, or about 6% PVP).

This composition is sometimes referred to herein as a "1×" resuscitation composition. It would be appreciated that a resuscitation composition can be formulated as a fraction thereof (e.g., as a 0.1×, 0.2×, 0.3×, 0.4×, 0.5×, 0.6×, 0.7×, 0.8×, or 0.9× resuscitation composition) or as a multiple thereof (e.g., a 1.1×, 1.2×, 1.3×, 1.4×, 1.5× or 2.0× resuscitation composition) by appropriately modifying the amount of both the BHB and the melatonin.

As demonstrated herein, a resuscitation composition as described herein can be made by solubilizing the melatonin or metabolite, precursor or analog thereof in a solution of HPbCD/PEG/PVP followed by lyophilization. In some instances, the pH of the solubilized melatonin can be adjusted to a pH of between 6 and 8 (e.g., to a physiological pH of 7.4) prior to lyophilization. Dried BHB then can be added to the lyophilized melatonin or metabolite, precursor or analog thereof, and the composition can be re-suspended in an aqueous solution (e.g., water, or water/HCl) to the desired final concentration. It also would be appreciated that the BHB can be dissolved in an aqueous solution (e.g., water) before being added to the lyophilized melatonin or metabolite, precursor or analog thereof. Alternatively, it would be appreciated that the BHB can be added to the melatonin/HPbCD/PEG/PVP solution and all of the components can be lyophilized together, or, after the BHB is added to the lyophilized melatonin or metabolite, precursor or analog thereof, the final composition can be re-lyophilized. In some instances, the pH of the final composition (e.g., prior to lyophilization) can be adjusted to a pH of between 6 and 8 (e.g., to a physiological pH of 7.4).

Importantly, the components of the resuscitation compositions described herein (e.g., the lyophilized M/HPbCD/PVP/PEG, with or without BHB or the lyophilized M/PVP with or without BHB) can be quickly combined and reconstituted (e.g., less than, for example, 3 minutes, 2 minutes, 1 minute), if necessary, in a one-step process, making them extremely useful in the field.

Methods of Using a Resuscitation Composition

A resuscitation composition as described herein can be used to treat an individual (e.g., their tissues and organs) that is experiencing a major hemorrhagic event, is at risk of experiencing a major hemorrhagic event, or has experienced a major hemorrhagic event. Major hemorrhagic events refer to a sudden or rapid loss of a significant amount of blood and can result in hemorrhagic shock. Major hemorrhagic events can be caused by, for example, loss of a limb, long bone fractures, laceration of an artery, or a gunshot or artillery wound. Major hemorrhagic events also include blunt trauma events that may, for example, result in internal bleeding. Motor vehicle accidents and gunshot wounds are leading causes of major hemorrhagic events. Additional causes of major hemorrhagic events include, without limitation, gastrointestinal, obstetric and gynecological bleeding.

One of the advantages of the resuscitation compositions described herein is the low volumes that can be used to effectively resuscitate an individual who is experiencing or has experienced a major hemorrhagic event. As described herein, it is desired that about 4 M BHB and about 43 mM melatonin (referred to herein as "1×") be delivered to an individual who is experiencing or has experienced a major hemorrhagic event and was formulated in this amount so that the composition could be delivered in an amount (e.g., a bolus) of about 1 ml per kg of body weight of the individual. It would be appreciated, however, that the volume of resuscitation composition administered to an individual can be more or less than 1 ml per kg of body weight and would depend on the final concentration of BHB and melatonin in the resuscitation composition. For example, a bolus of about 2 ml per kg of body weight of a 0.5× resuscitation composition would be the equivalent of a bolus of about 1 ml per kg of body weight of a 1× resuscitation composition.

Appropriate volumes of various concentrations of resuscitation compositions could be determined by a skilled artisan. In some instances, it is desirable that the resuscitation composition described herein be administered to an individual in as small a volume as possible. This small volume is significantly beneficial for emergency medical care in the field or under other circumstances in which supplies or space may be limited. For example, a volume of about 0.1 to about 2 milliliters (mls; e.g., about 0.1 to 0.4 mls, 0.2 to 0.7 mls, 0.5 to 1.5 mls, 0.5 to 1.0 mls, 0.6 to 0.7 mls, 0.75 to 2 mls, 1.0 to 2.0 mls, 1.5 to 2.0 mls, or about 0.5, 0.1 or 1.5 mls) per kilogram (kg) of weight of an individual is effective in protecting individuals from ischemia and reperfusion injury due, for example, to severe blood loss. Under other circumstances such as in a hospital or trauma center, however, a larger volume of a resuscitation composition (e.g., 100 ml or more per kg of weight of an individual) can be administered to an individual or a resuscitation composition can be continuously infused into an individual (e.g., following administration of a bolus of resuscitation composition). Although continuous infusion can utilize a number of different volumes and rates, an exemplary continuous infusion condition is 0.66 ml per kg of body weight per hour.

Similarly, a resuscitation composition as described herein can be used to treat an individual (e.g., their tissues and organs) that is experiencing, is at risk of experiencing or has experienced blood loss (e.g., significant blood loss). A resuscitation composition as described herein can be administered in instances in which an individual has lost a blood volume of at least about 10% (e.g., at least about 20%, at least about 30%, at least about 40%, at least about 50%, at least about 60% or more). It is noted that the volume of blood in an adult is considered to be approximately 7%-9% of their total body weight.

Blood loss, particularly when significant, often results in ischemia and then, subsequently, reperfusion injury. Ischemia typically occurs when tissues and organs are not sufficiently oxygenated, and reperfusion injury typically occurs when the tissues and organs are reoxygenated (e.g., because blood flow resumes or the individual is transfused with blood). Ischemia and reperfusion injury can result from a number of different traumas such as, without limitation, blood loss due to a major hemorrhagic event, stroke (e.g., occlusion stroke), cardiac arrest, myocardial infarction, heart attack, decreased arterial blood flow, or renal failure. Ischemia and reperfusion injury also can result from surgery in which the blood flow and/or oxygen flow is or may be disrupted. Certain surgical procedures such as neurosurgery or cardiac surgery have a higher risk for ischemic damage/reperfusion injury, and even using mechanical means (e.g., a heart-lung machine) during surgery may not entirely prevent ischemia and reperfusion injury. The resuscitation compositions described herein can be administered to individuals to significantly reduce or prevent ischemia reperfusion injury that tissues and organs might experience during or following such medical emergencies (e.g., severe hypothermia or hypoxia) or procedures (e.g., surgeries).

There are a number of physiological signs of a major hemorrhagic event. For example, a systolic blood pressure of about 90 mm Hg or less (e.g., about 85 mm Hg or less, about 80 mm Hg or less, about 75 mm Hg or less, about 70 mm Hg or less, 65 mm Hg or less, about 60 mm Hg or less, about 55 mm Hg or less, or about 50 mm Hg or less) in humans is indicative of significant blood loss. Similarly, tissue hemoglobin oxygen saturation ($StO_2$) levels below 75% (e.g., below 70%, below 65%, below 60%, below 55%, or below 50%) and/or base deficit levels of greater than 6 mEq/L (e.g., greater than 6.5 mEq/L or greater than 7 mEq/L) in humans also is indicative of significant blood loss.

During blood loss, an individual's heart rate can increase, blood pressure can decrease, urine output can decrease, lactate levels can increase, $StO_2$ levels can decrease, cardiac output can decrease, tissue pH can decrease, and mitochondrial function can decrease (e.g., as measured by NADH levels). Individual's recovering from such blood loss generally will exhibit a reversal of such symptoms; the heart rate can decrease, blood pressure can increase, urine output can increase, lactate levels can decrease, $StO_2$ levels can increase, cardiac output can increase, tissue pH can increase, and mitochondrial function can increase.

Simply by way of example, a generally healthy individual (i.e., one who is not suffering from hemorrhagic shock) typically will have a heart rate of less than 100 beats/minute, blood pressure of greater than 100 mm Hg systolic, urine output of greater than 30 cc/hour (or 1 cc/kg/hour for children), lactate levels of less than 2.1 mg/deciliter (dl), $StO_2$ levels of greater than 75%, cardiac index of 2.5-4.5 liters/min/m$^2$ (body surface area), blood pH of 7.35-7.45. On the other hand, an individual suffering from hemorrhagic shock (e.g., 10% blood loss or more) may have, simply by way of example, a heart rate of greater than 100 beats/minute, blood pressure of less than 100 mm Hg systolic, urine output of less than 300 cc/hour, lactate levels of greater than 2.1 mg/dl, $StO_2$ levels of less than 75%, cardiac index of less than 2.5 liters/min/m$^2$, and blood pH of less than 7.35. Often, the severity of the change in the biophysical parameter is directly related to the amount of blood lost and, therefore, such biophysical parameters can be monitored in individuals who are experiencing blood loss or who are recovering from such blood loss. Administering the resuscitation composition described herein can significantly temper an individuals' response to the blood loss (as gauged by one or more of the biophysical parameters described herein compared to an individual who undergoes a similar amount of blood loss but is not administered the composition) and/or increase the rate at which one or more biophysical parameters returns to "normal" (i.e., levels observed in generally healthy individuals).

A resuscitation composition as described herein can be administered intravenously to introduce the components directly into the bloodstream. Other routes of administration, however, also are suitable and include, for example, intraosseous administration. The particular formulation of a resuscitation composition is appropriate for the intended route of administration, and formulations for administration are well known in the art. See, for example, *Remington: The Science and Practice of Pharmacy*, 2005, 21$^{st}$ Ed., Lippincott Williams & Wilkins.

A resuscitation composition can be administered as a bolus, for example, by a first-responder (e.g., an armed services medic, an Emergency Medical Technician (EMT) or any other trained medical personnel) to an individual experiencing a major hemorrhagic event or a stroke or cardiopulmonary arrest. Alternately, or in addition to a bolus administration, a resuscitation composition can be administered as a slow-drip or infusion over a period of time. For example, a slow-drip or infusion can be administered at the scene of trauma, during transport to a medical facility, and/or once the individual reaches a medical facility.

Physiologically, the period immediately after injury or trauma is critical and is sometimes referred to as the "golden hour," but administration of a resuscitation composition to an individual can be continued for up to 72 hours or longer (e.g., up to 1 hour, 2 hours, 4 hours, 6 hours, 8 hours, 12 hours, 18 hours, 24 hours, 36 hours, 48 hours, 60 hours, 90 hours, or more). As an alternative to a slow-drip or infusion, a bolus of a resuscitation composition can be administered multiple times over, for example, a 24, 48 or 72 hour period of time.

Generally, an individual who has experienced a major hemorrhagic event will receive a blood transfusion upon reaching a medical facility, which, depending upon the circumstances, may take only a few minutes following the injury or may take up to several hours or more. In some instances, a resuscitation composition can be administered to an individual as soon as a potential ischemia or reperfusion injury is recognized, which may be after a blood transfusion has already begun. Those of skill would appreciate that a resuscitation composition as described herein could be administered coincidentally with a blood transfusion or plasma replacement or Lactated Ringers and, in some instances, a resuscitation composition can be combined directly with the blood or plasma or Lactated Ringers and administered to an individual.

Ischemia and reperfusion injury also can occur in transplanted organs. Therefore, a resuscitation composition as described herein can be administered to an organ donor prior to organ harvest. The organ donor can be in a persistent vegetative state, or can be alive and healthy and an appropriate match for the recipient. For example, an organ donor can be administered the resuscitation composition intravenously prior to the organ(s) being harvested so as to thoroughly perfuse the organ(s), thereby preventing or reducing ischemia of those tissues or organs during harvest and subsequent transport and preventing or reducing reperfusion injury following transplant into a recipient. In addition or alternatively to administering the resuscitation composition to an individual, one or more harvested organs can be, for example, perfused with or soaked in (e.g., during transport) the resuscitation composition.

Articles of Manufacture

A resuscitation composition described herein or the components therein can be included in an article of manufacture. Articles of manufacture that include a resuscitation composition can take any number of configurations, only a few of which are discussed herein. The following representative examples of articles of manufacture are not meant to be limiting.

In some instances, an article of manufacture can include one or more vessels (e.g., a first vessel, a second vessel, a third vessel, a fourth vessel, etc.). For example, in some instances, each of the individual components of a resuscitation composition (e.g., melatonin, solvent, BHB) can be contained within separate vessels; in some instances, the final resuscitation composition (i.e., melatonin, BHB and HPbCD/PVP/PEG) can be provided in a single vessel (e.g., in liquid form or powder form (e.g., lyophilized)); in some instances, melatonin solubilized in HPbCD/PVP/PEG and, optionally, lyophilized, can be contained within a vessel and the BHB re-suspended in an aqueous solvent (e.g., water)

and, optionally, lyophilized, can be contained within a second vessel; in some instances, a solid dispersion of melatonin in HPbCD/PVP/PEG (e.g., lyophilized) can be contained in a first vessel, BHB powder can be contained in a second vessel, and an aqueous solvent (e.g., water) can be contained in a third vessel.

In addition, an article of manufacture can include one or more dual chamber syringes (e.g., Vetter Lyo-Ject® dual-chamber syringe; Vetter V-LK® dual-chamber cartridge) that can be used to contain and deliver a resuscitation composition as described herein. In some instances, the final resuscitation composition (i.e., melatonin, BHB and HPbCD/PVP/PEG) in dried form can be contained within one of the dual chambers and an aqueous solvent (e.g., water) contained within the other chamber; in some instances, the melatonin solubilized in HPbCD/PVP/PEG and, optionally, lyophilized, can be contained within one of the dual chambers and the BHB re-suspended in an aqueous solvent (e.g., water) contained within the other chamber.

In some instances, a resuscitation composition can be provided in an IV bag. IV bags are well known in the art (see, for example, U.S. Pat. Nos. 5,098,409; 5,257,985; and 5,853,388). A resuscitation composition provided in an IV bag can be sterile and ready for use, with an appropriate expiration date indicated on the bag. Alternatively, a resuscitation composition provided in an IV bag can be in a dry form (e.g., lyophilized) ready for dissolution or resuspension in an appropriate solvent.

In some instances, a resuscitation composition can be provided in a syringe barrel or cartridge structure. A resuscitation composition contained within a syringe barrel or cartridge structure can be provided already re-suspended, provided in a dry powder form for resuspension prior to use, or provided in dry powder form with the syringe barrel or cartridge structure also containing the solvent or solvents for re-suspending the dry powder or its components.

In certain instances, a solution containing the BHB or pharmaceutical salt thereof and a solution containing the melatonin or metabolites, precursors or analogs thereof can be mixed prior to administration, such that an individual receives both components in a single composition. In other instances, the BHB or pharmaceutical salt thereof can be administered to an individual followed by or preceded by (separate) administration of melatonin or metabolites, precursors or analogs thereof. Given that BHB and melatonin may have different half-lives, the two components can be initially administered together in a single composition followed by administration of one component (e.g., melatonin or metabolites, precursors or analogs thereof) more frequently than administration of the other component (e.g., BHB or pharmaceutical salt thereof).

In addition to the components of the resuscitation composition, an article of manufacture generally includes packaging material. The packaging material can include a label or package insert that has instructions for treating an individual who is experiencing or has experienced blood loss, an individual who had a stroke or a cardiopulmonary arrest or is at risk of having a stroke or cardiopulmonary arrest, an individual who is about to undergo or is undergoing surgery, or an individual who is about to donate an organ or tissue.

It is advantageous to formulate a resuscitation composition in dosage unit form for ease of administration and uniformity of dosage. Dosage unit form as used herein refers to physically discrete units suited as unitary dosages to be administered to an individual, with each unit containing a predetermined quantity of resuscitation composition to produce the desired therapeutic effect. A dosage unit form of a resuscitation composition generally is dependent, for example, upon the desired concentration of BHB and melatonin in the blood of an individual and the weight of an individual.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part I—Evaluation of Melatonin

Part A—Preliminary Results

Example 1—Reducing the Concentration of Melatonin and the Corresponding DMSO Solvent The BHB/M solutions described herein contain melatonin at a concentration exceeding its solubility in water, necessitating the use of a solubilizer. As indicated herein, the preclinical formulation (see, for example, U.S. Pat. Nos. 8,728,532 and 9,149,450) contained dimethyl sulfoxide (DMSO) at a level that is acceptable for use in animals but has an unknown safety profile in humans. A potential adverse effect of DMSO is the induction of hemolysis (rupture of red blood cells), which can result in anemia and other adverse effects.

Figure 1:
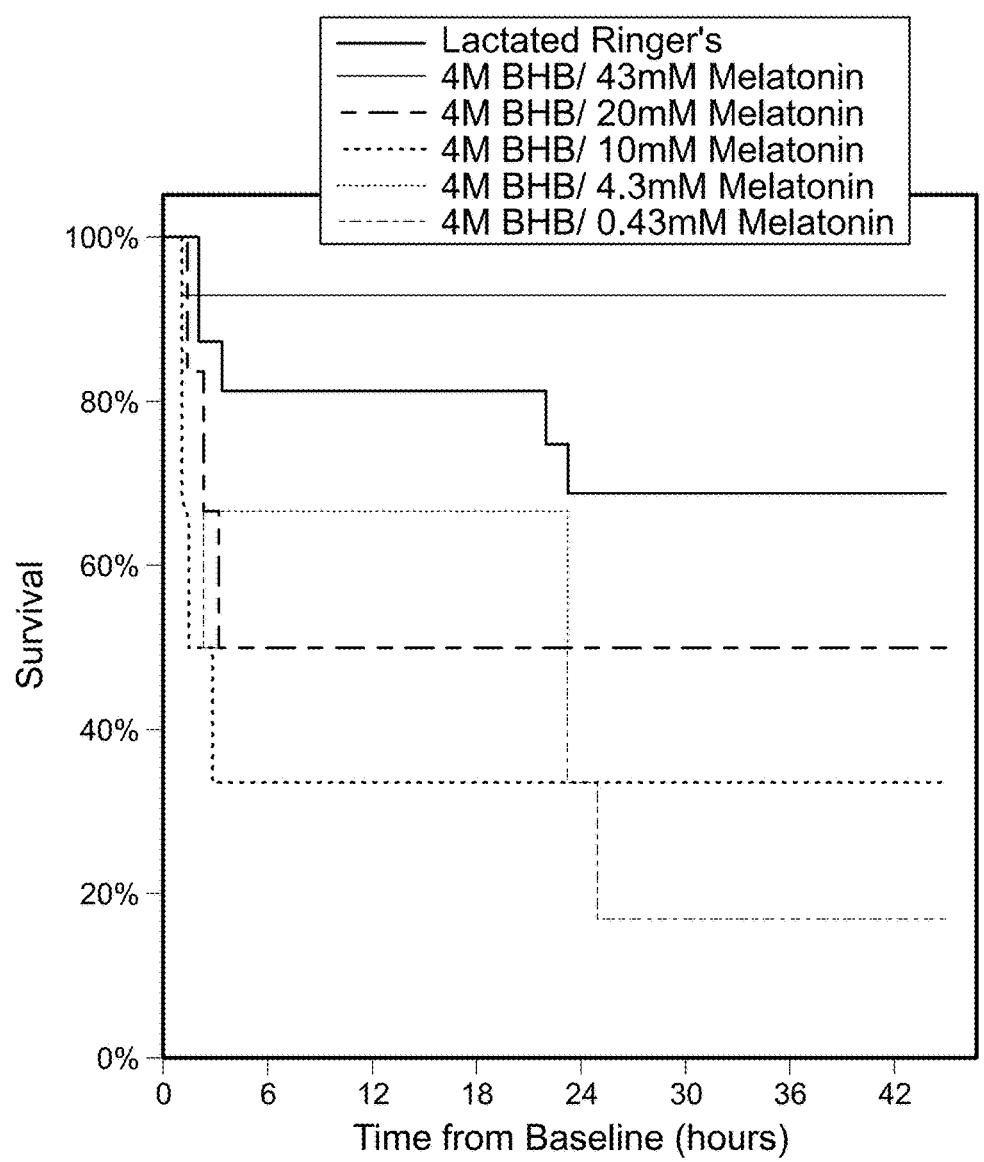
FIG. 1 is a graph showing that a lower amount of melatonin resulted in decreased survival in a pig hemorrhagic shock and trauma model.

Therefore, it was tested whether the amount of melatonin, and therefore DMSO, in the formulation can be decreased without losing any significant efficacy. Unfortunately, the survival benefit observed after treatment with a reduced amount of melatonin and, hence, the solubilizer, was not observed in pigs exposed to injury and hemorrhagic shock. FIG. 1.

Briefly, overall survival was significantly different 48 hours after baseline ($p=0.011$), with the lowest mortality observed in pigs treated with 4 M BHB/43 mM melatonin (1/14), followed by pigs treated with Lactated Ringers (5/16) and those receiving lower doses of melatonin. The animals that received less melatonin experienced more severe injury, as demonstrated by increased lactate levels, increased organ injury markers (e.g., serum creatine kinase, serum AST, serum urea nitrogen), and a higher rate of acute lung injury (P:F ratio <300). BHB/M-treated pigs experienced melatonin dose-independent increases in blood Na+, base excess and pH and decreases in K+.

The results shown in FIG. 1 clearly demonstrate that treatment of pigs experiencing hemorrhagic shock and trauma with 4 M BHB and lower amounts of melatonin lacks the survival benefit observed from treatment with 4 M BHB/43 mM melatonin.

Example 2—Solubility of Melatonin

Figure 2:
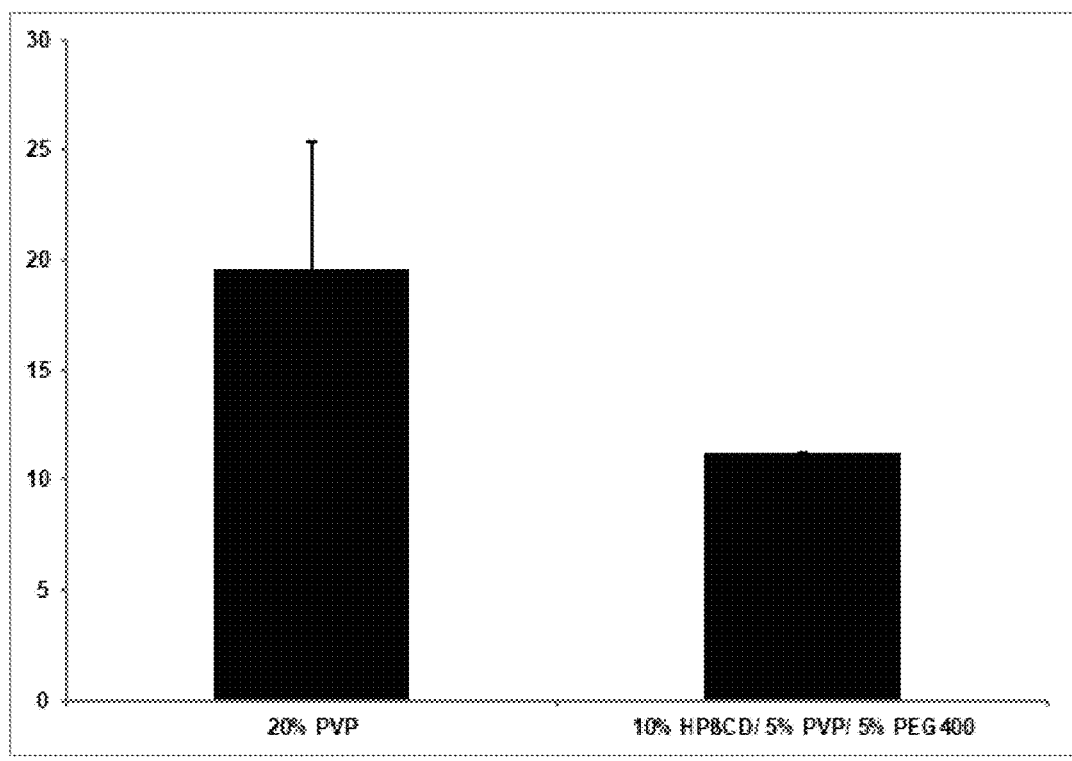
FIG. 2 is a graph showing the solubility of melatonin (target concentration 10 mg/ml) in 20% PVP (left) and 10% HPbCD/5% PVP/5% PEG400 (right).

A saturated melatonin solution was prepared containing the indicated excipient concentrations and incubated end over end at room temperature for 72 hours. After 72 hours, solutions were filtered through a 45 μm filter and diluted 1:10. Absorption was measured spectrophotometrically at 287 nm (excipient solutions alone were used as blanks). FIG. 2 shows adequate melatonin solubility (>43 mM/10 mg/ml) in 20% PVP and in 10% HPbCD/5% PEG400/5 % PVP K12.

Example 3—X-Ray Diffraction of Lyophilized Melatonin

Figure 3:
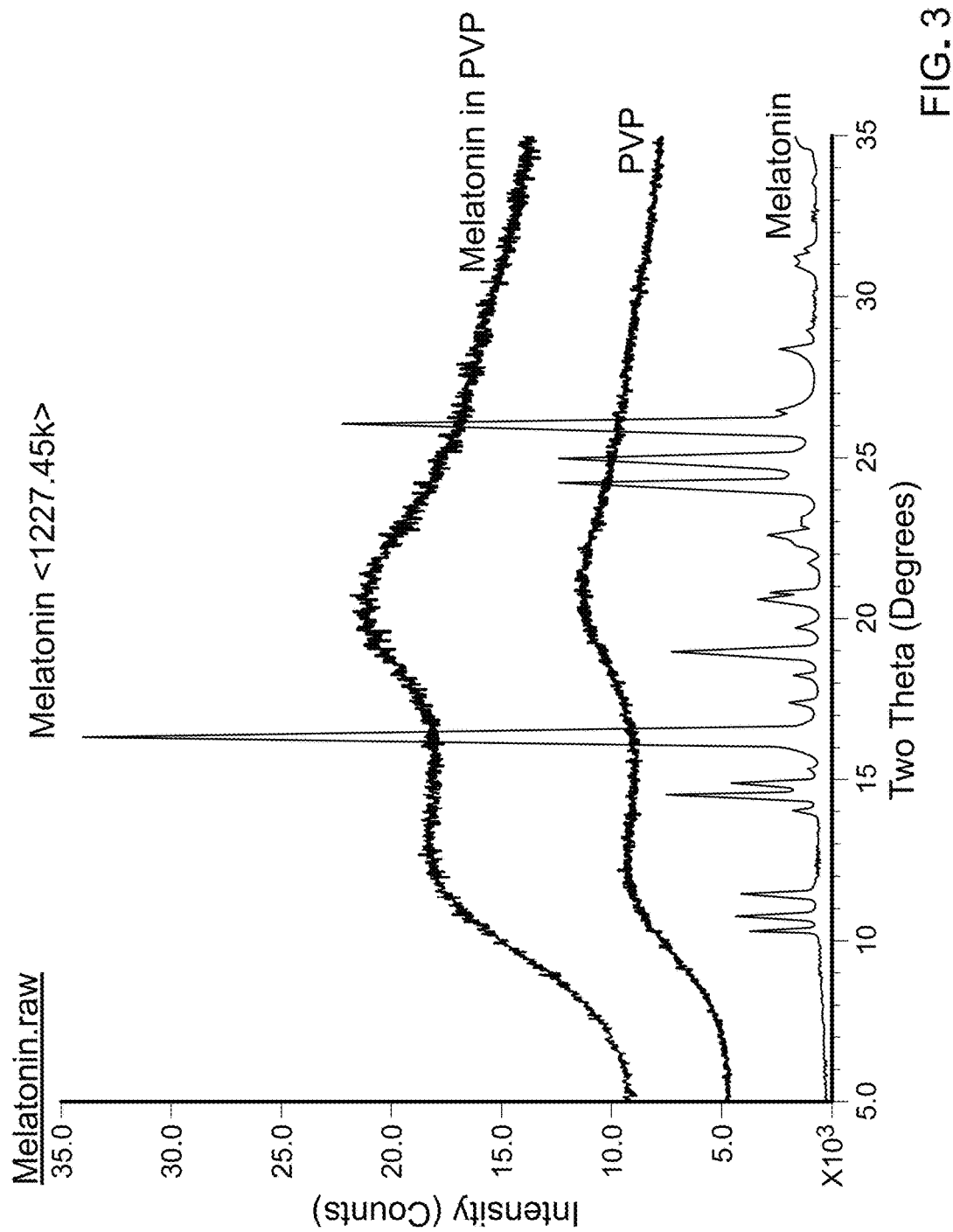
FIG. 3 shows the x-ray diffraction spectrum of crystalline melatonin and lyophilized melatonin in PVP.

Solid formulations of 43 mM melatonin in 20% PVP were generated via lyophilization and analyzed using x-ray diffraction spectrum. See FIG. 3. These experiments demonstrated that melatonin is amorphous after lyophilization.

Part B—Development and In Vivo Evaluation of a Novel Lyophilized Formulation for the Treatment of Hemorrhagic Shock

Example 4—Materials

BHB (Lonza, Basel, Switzerland and Sigma Aldrich, St. Louis, Mo.), melatonin (Flamma S.p.A., Chignolo, Italy), polyvinylpyrrolidone (PVP) (K-12, Acros Organics, Geel, Belgium) and lactated Ringer's solution (Baxter, Deerfield, Ill.) were used as received.

Example 5—Methods

Solubility Studies. Preliminary screening experiments revealed that the solubility of MLT could be enhanced with polyvinylpyrrolidone (PVP), a polymer with a history of use in parenteral products. An excess amount of MLT was added either to water or PVP solution (concentration ranging from 0.1 to 20% w/v) in polypropylene tubes (protected from light) and incubated with end-over-end rotation at 25° C. until equilibrium was achieved (72 hours). An aliquot was filtered (0.45 μm membrane) and the absorption measured at 270 nm (Epoch microplate spectrophotometer, BioTek, Winooski, Vt.).

A 21.5 mM MLT solution was prepared in 10% w/v PVP, the contents were protected from light and rotated end-over-end for 12 h. The solution was lyophilized (details in the next section) to obtain an MLT-PVP dispersion.

Lyophilization. Equal volumes of BHB (4 M; pH adjusted to 7.4 by addition of 0.6 M HCl) and MLT (43 mM in 20% w/v PVP) solutions were mixed. Assuming a weight average molecular weight of 2500, the PVP concentration is 40 mM. The solution was filled into 10 mL glass vials (2 mL fill volume), covered with rubber stopper (20 mm, 2 Leg Lyo, Gry Butyl Sil, Wheaton) and loaded into the lyophilizer. Lyophilization was carried out in a bench top freeze-dryer (VirTis AdVantage, Gardiner, N.Y.). The shelf was cooled to −60° C. at 0.25° C./min and held for 4 h. Primary drying was sequentially conducted at −40° C. (12 h), −30° C. (24 h), and −20° C. (12 h) at 100±25 mTorr. During secondary drying, the shelf was progressively heated to −10° C., 0° C., +10° C., +25° C. and +40° C. and held at each temperature for 6.6 h. At the end of the cycle, the vials were stoppered and stored in a desiccator containing anhydrous calcium sulfate at −20° C.

Differential Scanning calorimetry. A differential scanning calorimeter (Q2000, TA Instruments, New Castle, Del.) equipped with a refrigerated cooling accessory was used. Dry nitrogen gas was purged at 50 mL/min. For thermal analysis of prelyo solution, ~20 μL of solution was weighed in an aluminum pan, sealed hermetically, cooled from RT to −90° C. at 1° C./min, held for 30 min and heated to RT at 10° C./min. Selected systems were annealed wherein the solutions were cooled from RT to −90° C. at 1° C./min, held for 30 min, heated to the annealing temperature (−35° C.; 1° C./min), annealed for 12 h, cooled back to −90° C. at 1° C./min and heated to RT at 10° C./min. In case of lyophiles, the powder was filled into the aluminum pan at RT (in a glove box under nitrogen purge; RH≤5%), sealed non-hermetically, and heated from RT to 180° C., at 10° C./min. The more specific experimental details are provided in the appropriate figure legends.

Thermogravimetric Analysis. In a thermogravimetric analyzer (Model Q500, TA instruments), ~5 mg of sample was heated in an open pan from RT to the desired temperature, at 10° C./min, under dry nitrogen purge.

IR Spectroscopy. Spectra (Vertex 70, Bruker, Ettlingen, Germany; equipped with a Globar mid-IR source) were obtained using an attenuated total reflectance (ATR) accessory (single reflection germanium crystal) and a DLaTGS detector. The resolution was 4 $cm^{-1}$, and 32 scans were acquired in the range of 4000-400 $cm^1$. The peak positions were determined using OPUS software peak picking function.

X-Ray Diffractometry. A powder X-ray diffractometer (D8 ADVANCE; Bruker AXS, Madison, Wis.) equipped with a Si strip one-dimensional detector (LynxEye) was used. Samples were exposed to Cu Kα radiation (40 kV×40 mA) over an angular range of 5-35° 2θ with a step size of 0.02° and a dwell time of 0.5 s.

For the variable temperature experiments, about 50 mg of powder was packed (top filling) into a copper holder and the stage was heated, under nitrogen purge, from RT to the desired temperature at 10° C./min. During the XRD scan, the sample at the selected temperature was maintained under isothermal conditions.

Water vapor sorption. About 5 mg of sample was placed in the quartz sample pan of an automated vapor sorption balance (DVS-1000, Surface Measurement Systems, London, UK), maintained at 25° C. It was dried under dry nitrogen purge (flow rate 200 mL/min) to constant weight. Equilibrium was assumed to have been achieved if the mass change was <0.001% over 30 min. The relative humidity (RH) was progressively increased to 55%, at increments of 5%. Equilibrium was assumed to have been achieved if the mass change was <0.005% over 30 min. The microbalance was calibrated periodically using a 100 mg standard weight.

Example 6—Hemorrhagic Shock Model

Figure 4:
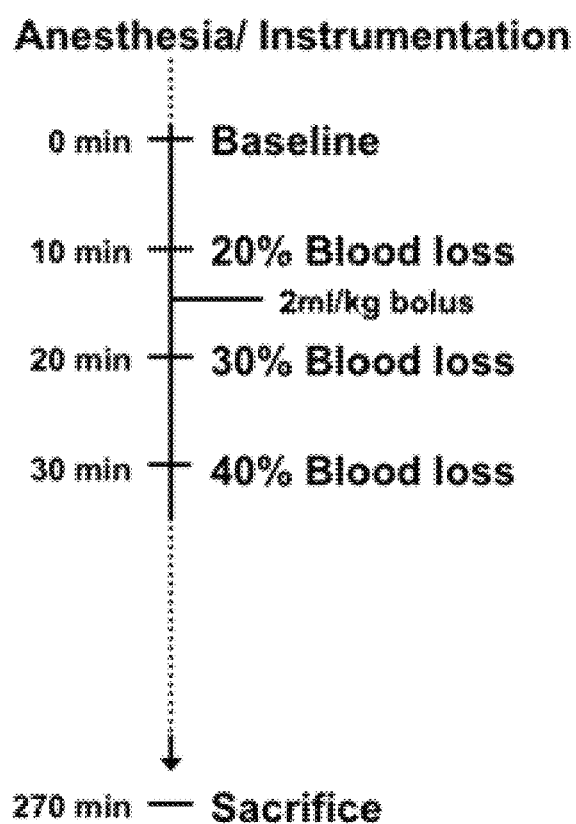
FIG. 4 is a flow chart showing the rat model of hemorrhagic shock.

Anesthesia and cannulation. The experiment was conducted as described in FIG. 4. All animal experiments were approved by the Institutional Animal Care and Use Committee of the University of Minnesota and carried out in accordance with AAALAC regulations. Forty-one male Sprague-Dawley rats (350-375 g, Envigo) were allowed to adapt for at least seven days before the experiment. Animals were kept on a 12-hour light dark cycle with water and food ad libitum. On the day of the experiment, rats were anesthetized in an induction chamber with isoflurane (5% in 1 L/min oxygen), treated with meloxicam for analgesia (0.5 mg, s.c.), and placed on a heating pad. Anesthesia was maintained with isoflurane via nose cone (1-2% in 1 L/min oxygen, Surgivet Isotec 4, Smiths Medical PM, Inc, Norwell, Mass.). The right external jugular vein was aseptically exposed and cannulated with sterile PE 160 tubing for blood drawing and treatment administration. The left femoral artery was aseptically exposed and cannulated with a 24G catheter for heart rate and blood pressure measurements.

Hemorrhagic shock and infusion protocol. After cannulation, rats were allowed to stabilize for ten minutes, and baseline measurements were taken. Immediately after baseline sampling, blood was gradually withdrawn in three steps to achieve a total loss of 40% of the total blood volume over 30 minutes. Total blood volume was calculated as 7% of body weight. Fourteen minutes after baseline measurements, half-way through blood withdrawal, an intravenous treatment bolus was administered (2 ml/kg over 1 min). Lines were flushed with lactated Ringer's solution (LR) after blood draws and solution administration. Animals were maintained anesthetized until they expired or were euthanized via exsanguination four hours after the end of blood withdrawal. Sham rats were only cannulated, no bolus was administered and no blood was withdrawn other than for sample analysis at the end of the experiment.

Kaplan-Meier estimator with generalized Wilcoxon test was used to analyze survival differences between the groups. Longitudinal parameters were analyzed using the Proc Mixed procedure in SAS Version 9.4 software (SAS Institute, Inc., Cary, N.C.). Group, Timepoint and Group*Timepoint Interaction were modeled as fixed effects. The models used autoregressive (AR(1)) covariance structure and the between-within method for degrees of freedom. For parameters with significant interaction effects, differences at individual time points were analyzed by pairwise comparisons with Tukey adjustments. Longitudinal data is presented as least-squared means with 95% confidence intervals.

Example 7—Solubility Enhancement of MLT in Presence of PVP

Figure 5:
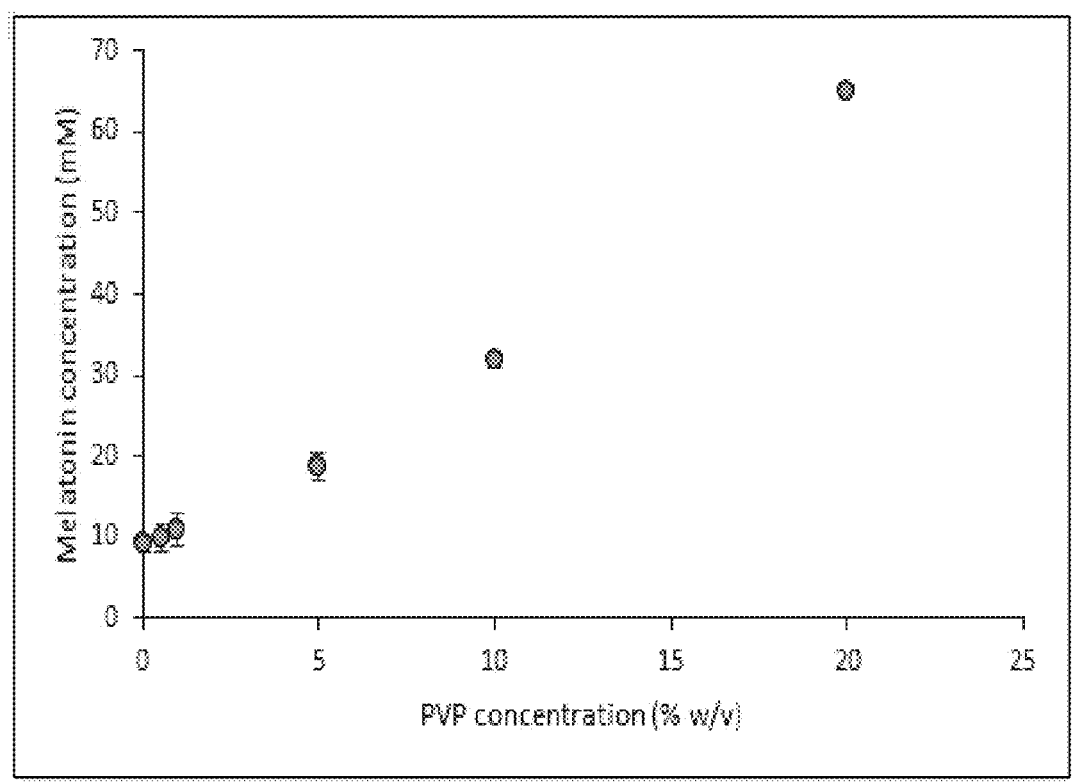
FIG. 5 is a graph showing the effect of PVP concentration on aqueous MLT solubility at 25° C. (n=3).
Figure 15:
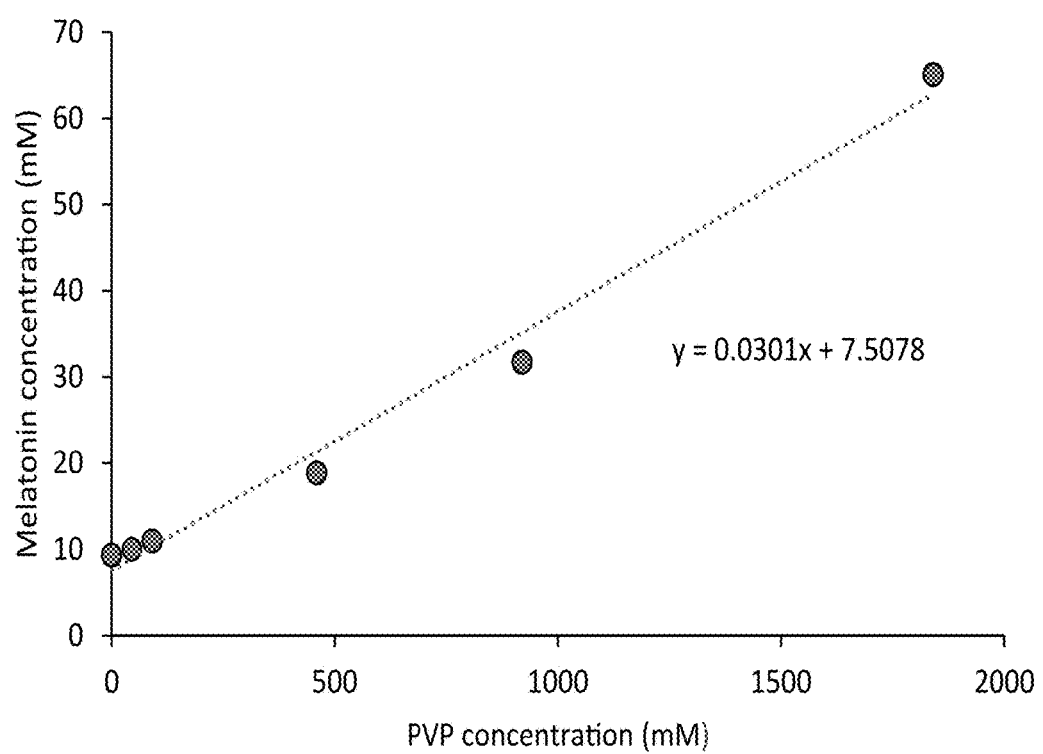
FIG. 15 is a graph showing the solubility of melatonin in PVP solutions. Assuming formation of 1:1 complex between drug and ligand, the complexation efficiency (CE) can be calculated from the slope of the phase-solubility diagram.

The phase solubility diagram for MLT-PVP system in water at 25° C. is presented in FIG. 5. The MLT solubility increased linearly as a function of PVP concentration, suggesting formation of a water-soluble complex with a solubility higher than that of MLT. Such a behavior is the characteristic feature of $A_L$ type phase solubility diagram. The complexation efficiency and MLT: PVP molar ratio (taking, PVP repeating units to be its molecular weight) were determined to be 0.03 and ~33 respectively (FIG. 15). The molar ratio of total drug to free drug at a given polymer concentration has also been widely used as a measure of drug (MLT in our case)—ligand (PVP) binding affinity. Literature values for approximately 40 compounds in 1.0% w/v PVP show that the ratio rarely exceeds 1.2. For MLT, the ratio was found to be 1.17, suggesting complexation of intermediate strength. PVP is known to form water soluble or insoluble complexes with various drugs with either enhancement or reduction in solubility.

Detailed studies of compounds with diverse chemical structures has revealed that the binding of neutral substances to PVP very closely parallels the transfer of the substances from a water phase to n-octanol. Thus, there is no specific orientation of the substance onto PVP and the interaction can best be described as hydrophobic binding. The binding process has been shown to be thermodynamically favored because of increased disorder or entropy of water molecules whose ice-like cages are disrupted on complexation.

Non-polar groups, both in the polymer and in the compounds, when in aqueous solution are surrounded by one or more layers of water molecules which are more ordered than in liquid water. This higher ordering, approximated by an ice-like structure, is termed "iceberg." The entropy changes in the course of the binding process can be assumed to be due to the disordering, partial or total, of the icebergs. The polymer-solute complex will thus be surrounded by a less ordered iceberg than in the two separate entities. The release of water molecules from the ordered structure should produce a proportional gain in entropy.

Example 8—Solid-State Characterization of MLT-PVP Dispersion

Figure 6A:
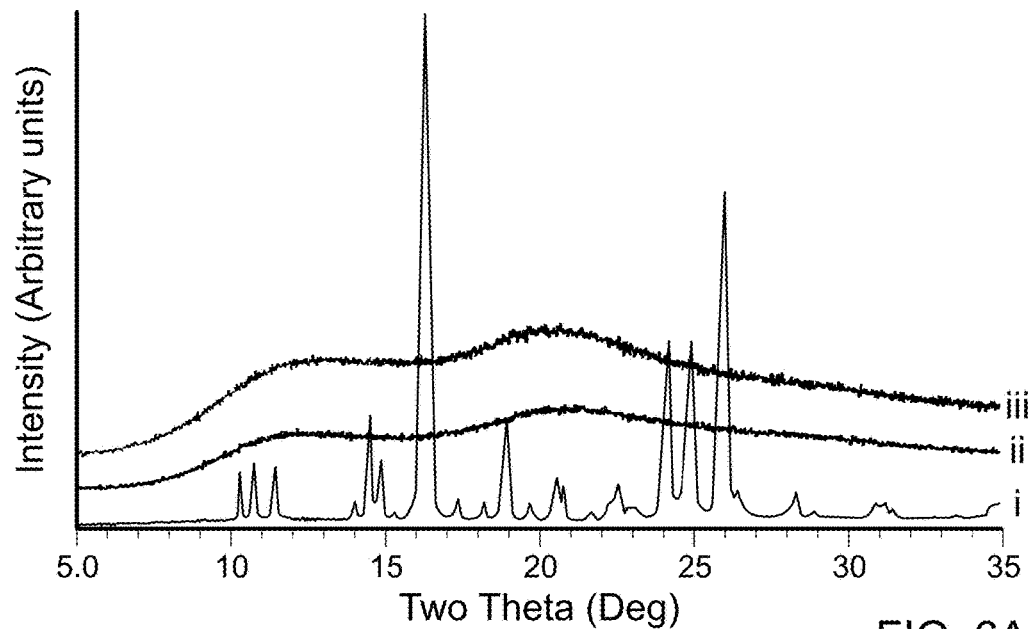
FIG. 6A is a graph showing XRD patterns of MLT 'as is' (line i), PVP K-12 'as is' (line ii) and the lyophilized MLT-PVP dispersion (line iii).
Figure 6B:
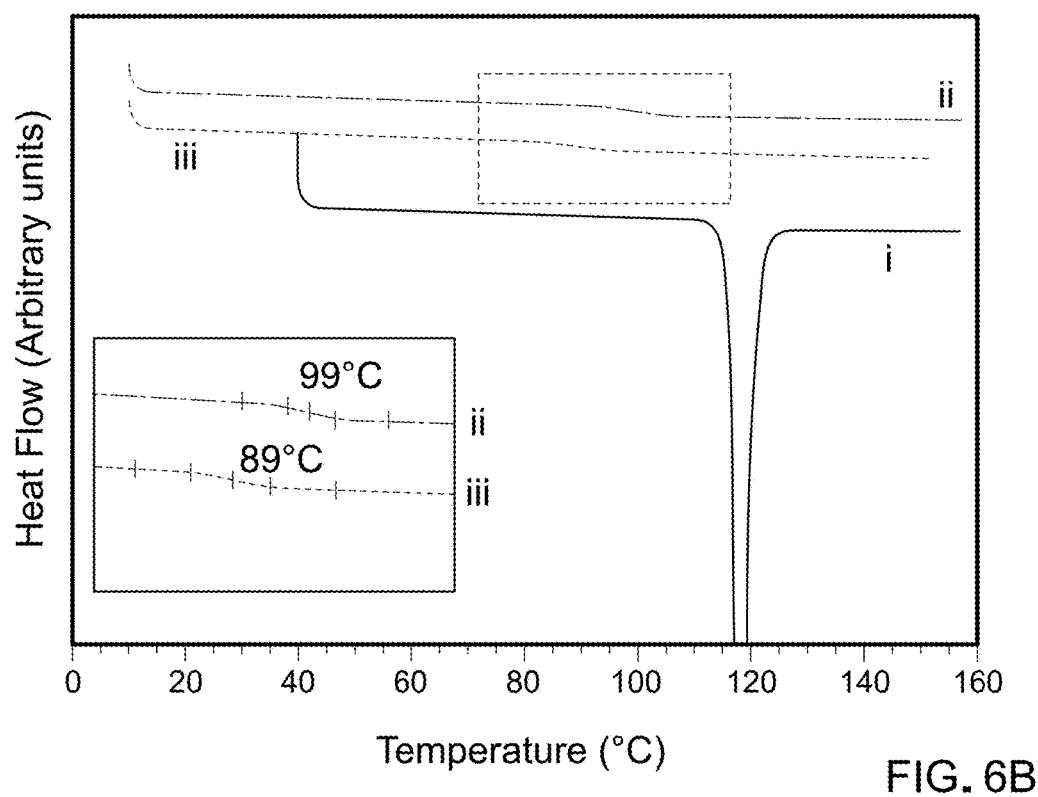
FIG. 6B is a graph showing DC heating curves of MLT 'as is' (line i), PVP K-12 'as is' (line ii) and the lyophilized MLT-PVP dispersion (line iii). The region of the glass transition has been expanded.
Figure 7:
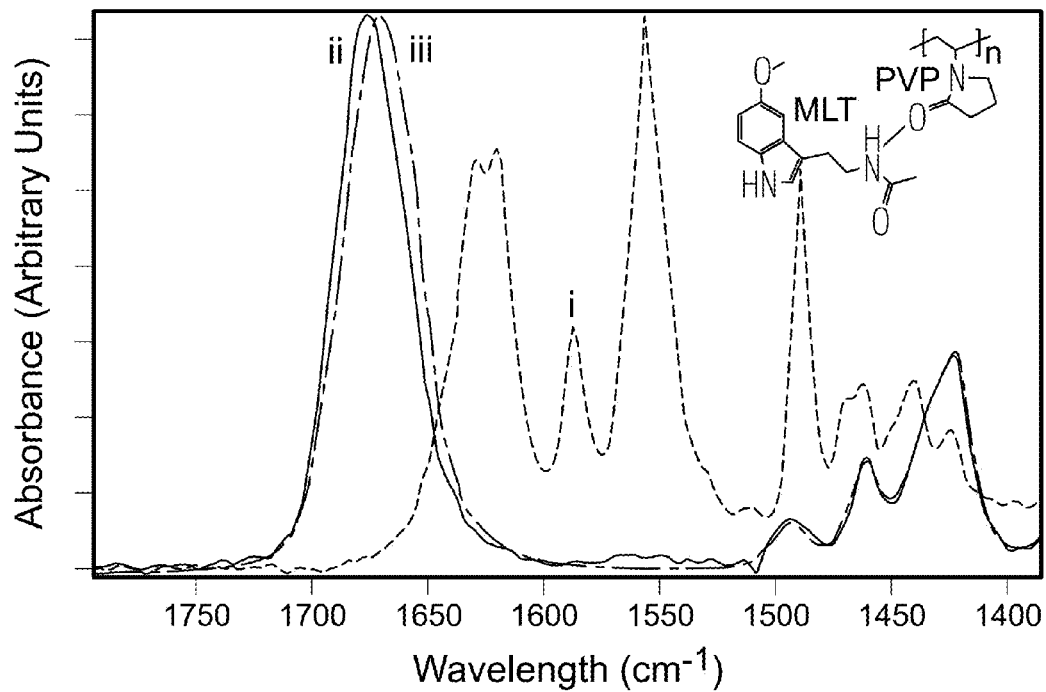
FIG. 7 is a graph showing the IR spectra of MLT (line i), PVP (line ii) and MLT-PVP dispersion (line iii). The H-bonding interaction between MLT and PVP is pointed out.

One of the aims was to attain an aqueous MLT concentration of 21.5 mM which is substantially higher than its equilibrium solubility of ~8 mM at 25° C. This could be achieved by the addition of at least 10% w/v PVP (40 mM). In order to characterize the MLT-PVP solid phase, a 21.5 mM MLT solution in 40 mM PVP was lyophilized. The broad halo in the XRD pattern coupled with the absence of the characteristic peaks of MLT indicated that the lyophile was amorphous (FIG. 6A). Thermal analysis revealed a single step change with mid-point at ~89° C., indicative of glass transition (FIG. 6B). This is somewhat lower than the glass transition temperature of PVP (~99° C.), which may be attributed to the presence of 4.7% w/w MLT in the dispersion. As expected, an endotherm attributable to MLT melting (118° C.), was absent (FIG. 6B). To study the intermolecular interaction between MLT and PVP in the lyophile, the IR spectrum of the lyophile was compared with those of MLT and PVP. The IR spectrum of the dispersion was essentially superimposable on that of PVP. The carbonyl stretch of PVP (1674 cm$^{-1}$) was found to shift to slightly lower frequency (1669 cm$^{-1}$), which is suggestive of hydrogen-bonding interaction of PVP with MLT in the solid-state (FIG. 7). No unique signal attributable to MLT was discerned (for example at 1629, 1587, 1556, 1212 or 1024 cm$^{-1}$). Since the MLT content was <5% w/w, sensitivity may be an issue.

Example 9—Solid-State Characterization of BHB

The physical form (polymorphic form, degree of crystallinity and state of solvation) of the API can significantly influence the processing, stability and performance of the dosage form. Therefore BHB was subjected to detailed physical characterization.

The crystal structure of BHB is not reported in the Cambridge Structural Database. Its XRD pattern showed a very prominent peak at 7.1° 2θ (d-spacing 12.3 Å), strongly suggesting preferred orientation of crystallites (bottom XRD pattern in FIG. 8). Several other peaks were observed, for example at 12.1, 14.2, 17.4, 30.1 and 30.5° 2θ.

Figure 9:
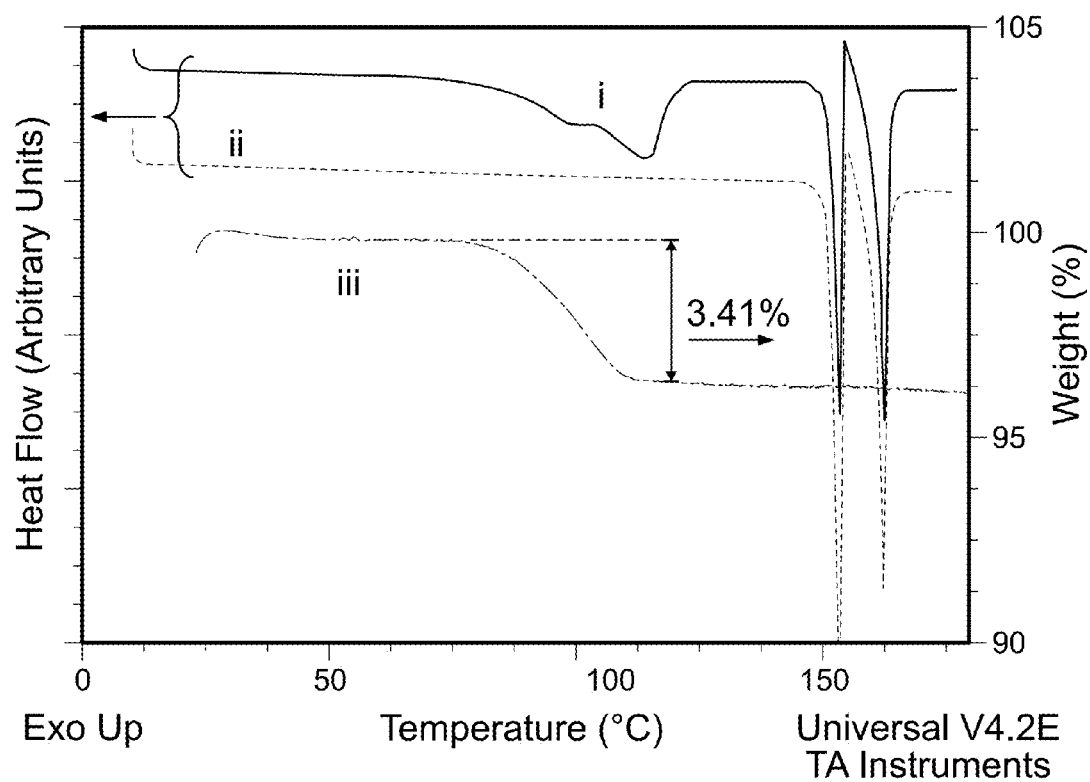
FIG. 9 shows a graph of DSC (left y-axis) heating curves of BHB 'as is' (line i) and BHB heated to 130° C., cooled and reheated (line ii). Only the second heating curve is shown. TGA (right y-axis) of BHB 'as is' (line iii).

BHB was initially handled under ambient RH conditions (25% RH; 25° C.). Its water content, determined by Karl-Fischer titrimetry, was ~3% w/w. DSC (FIG. 9, line i; nonhermetically crimped pan), revealed a broad endotherm over 80-130° C., the same temperature range in which a weight loss (~3%) was observed in the TGA (FIG. 9, line iii). Therefore, the endotherm is likely due to dehydration followed by vaporization of water. When a fresh sample was heated up to 130° C. in an open pan, cooled and reheated, the endotherm was not observed (FIG. 9, line ii). This confirmed that the endotherm was associated with water loss.

DSC heating curve exhibited additional thermal events at higher temperature (FIG. 9, line i)—an endotherm at ~153° C., followed immediately by a weak exotherm, and a second endotherm at 163° C. The observed series of thermal events can be interpreted as: dehydration and vaporization of water leading to the formation of a metastable anhydrate (80-130° C.)→melting of the metastable phase (form I) immediately followed by crystallization of a second anhydrous phase (form II; this may be a stable phase) (153)→melting of form II (163).

Figure 8:
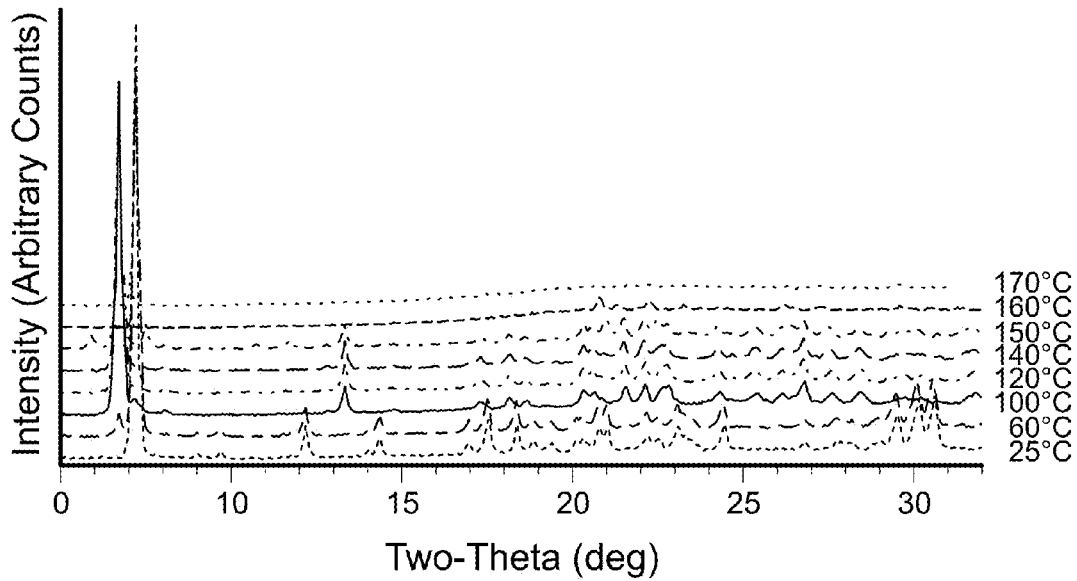
FIG. 8 shows the x-ray diffraction patterns of the BHB heated from RT, first to 60° C. and then progressively to 100, 120, 140, 150, 160 and 170° C. The heating rate was 10° C./min, and the sample was held for 6 min under isothermal conditions during the XRD run.

Variable temperature XRD enabled interpretation of the DSC results (FIG. 8). Upon heating the sample, starting at 60° C., there was a decrease in the peak intensity at 7.1° 2θ and appearance of a new peak at 6.9° 2θ. On further heating, new peaks were observed at 13.3, 22.8 and 26.8° 2θ (form I). Thus, the dehydration and formation of crystalline anhydrate occurred over a wide temperature range. The pronounced differences in the XRD pattern (compare patterns at 25 and 120° C.) reveal that the lattice structure of the anhydrous phase is different from that of the hydrate. The XRD patterns were unchanged between 120 and 140° C. However, the pattern at 150° C. exhibited several new peaks, indicating the appearance of a new phase (form II). The XRD pattern at 150° C., suggests the existence of a mixture of forms I and II. All the peaks disappeared at 170° C., suggesting complete melting of form II. Thus, the VTXRD results are in good agreement with the series of thermal events between 150 and 170° C.

Figure 10:
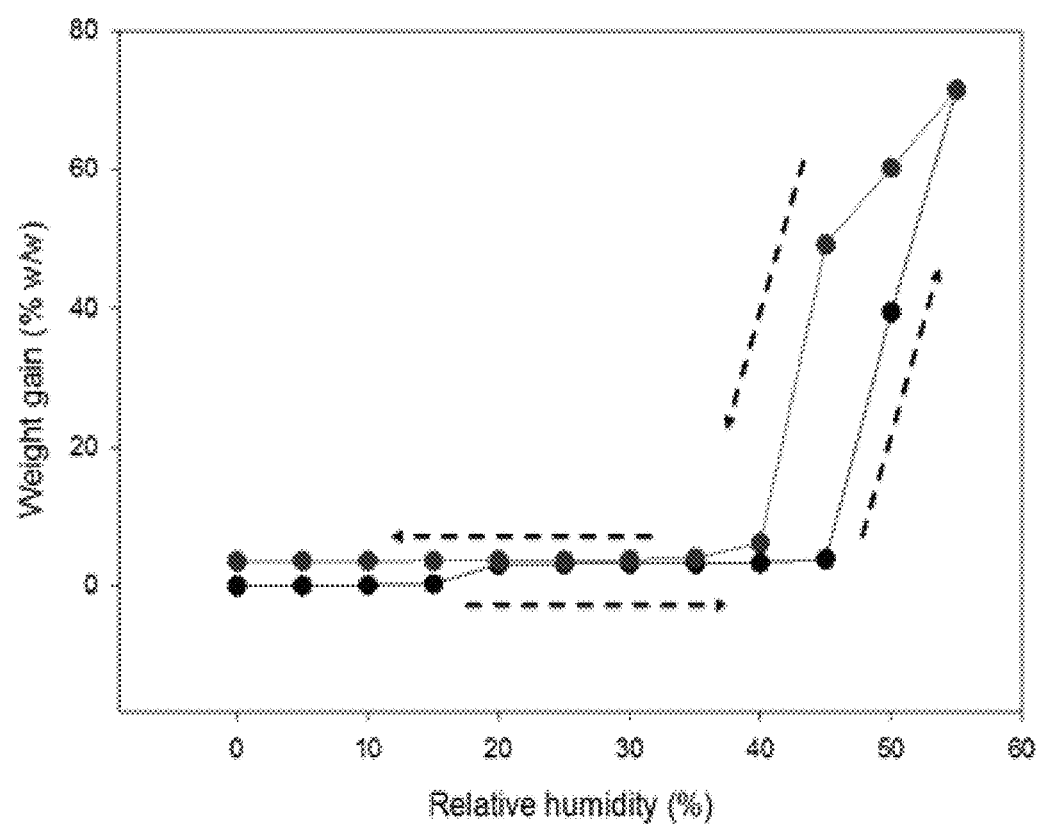
FIG. 10 is a graph showing the water sorption (black circles) and desorption (red circles) profiles of BHB at 25° C.

In order to gain a deeper understanding into the water-BHB interaction, the 'as is' BHB was heated in the TGA up to 120° C., cooled to RT and transferred to the sample chamber of the water sorption analyzer. The other relevant details are provided in the Experimental section. There was no water sorption up to 15% RH and then the sample gained ~3% water at 20% RH (FIG. 10). This is in excellent agreement with the water content in 'as is' BHB. When exposed to progressively higher RH values, there was another sharp increase in weight of ~40% at 50% RH, suggesting sample deliquescence. However, under the experimental conditions in the water sorption analyzer (maximum dwell time of 360 minutes at any RH), equilibrium was not attained. Therefore, when the RH was further increased to 55%, a pronounced weight increase again was observed. When the RH was progressively reduced, the sample exhibited efflorescence. Interestingly, it retained 3% w/w water even when the RH in the sample chamber was reduced to 0%, again suggesting that equilibrium was not achieved (FIG. 10). There were two RH ranges, (0-20% and 35-55%) where hysteresis was observed.

If BHB formed a monohydrate, the stoichiometric water content would be 12.5% w/w. The observed water content in 'as is' BHB of ~3.0% suggests that, under ambient conditions, the drug exists as BHB·0.25 $H_2O$. There are examples of pharmaceutical hydrates where multiple drug molecules may be associated with one water molecule of hydration, giving the system an overall stoichiometry of, for example, 0.2 hydrate (e.g., lamuvudive) and hemihydrate (e.g., mannitol and aspartame).

Example 10—Characterization of Pre-Lyophilization Solution

Figure 11:
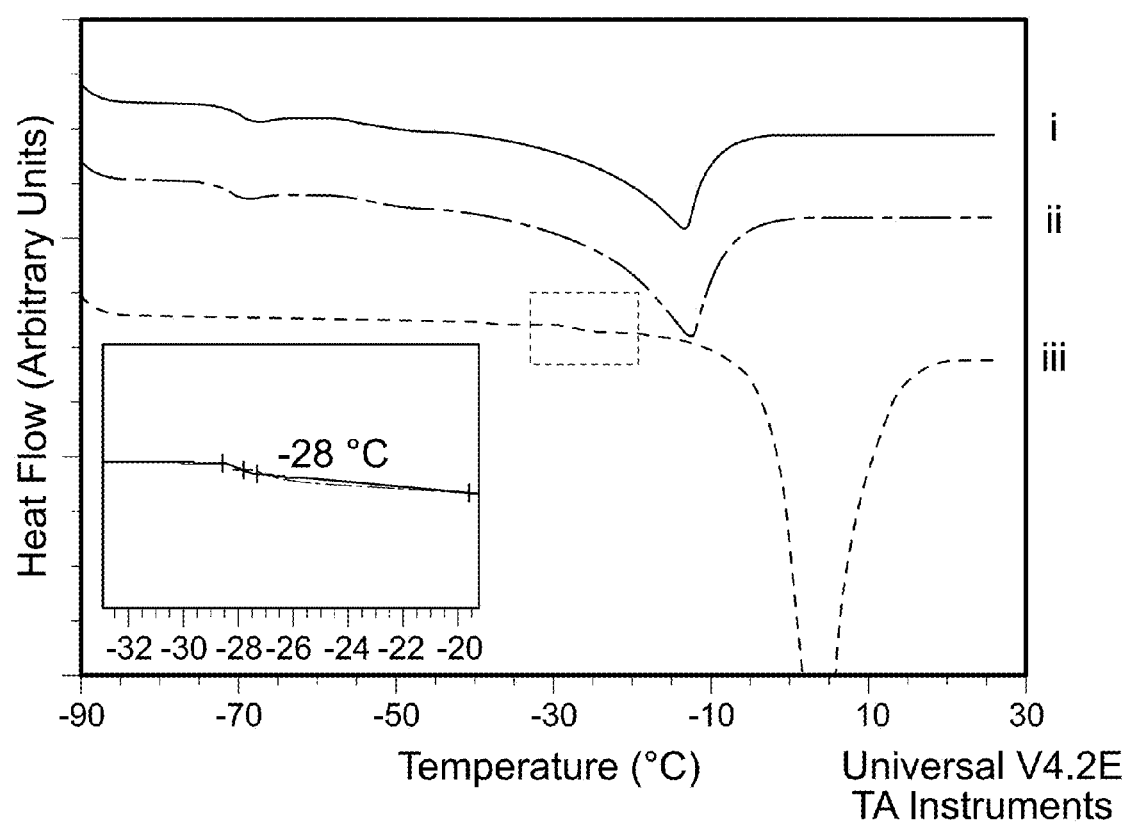
FIG. 11 is a graph showing the DSC heating curve of frozen aqueous solutions of: BHB (2 M) (line i), BHB (2 M)-MLT (21.5 mM)-PVP (40 mM) (line ii), and MLT (21.5 mM)-PVP (40 mM) (line iii) solution. The solutions were initially cooled from RT to −90° C. at 1° C./min, held for 30 min, and heated to 25° C. at 10° C./min. Only the heating curves are shown. A select region has been expanded to enable visualization of glass transition of MLT-PVP freeze-concentrate (Tg'). The midpoint of Tg' is reported.

Solutions of (i) MLT-PVP, (ii) BHB and (iii) BHB-MLT-PVP were cooled from RT to −90° C. and held for 30 minutes. FIG. 11 contains the DSC curves of these solutions heated from −90° C. to RT. The frozen MLT-PVP solution exhibited a baseline shift at ~−28° C., attributed to the glass transition of the freeze concentrate, Tg'. This was followed by an endotherm at ~1° C. due to ice melting (FIG. 11). The DSC heating curve of frozen solution containing BHB exhibited baseline shifts, first at ~−69° C. (Tg') and the second starting at ~−53° C. attributed to softening. This was followed by an ice melting endotherm at ~−13° C. The DSC heating curve of frozen prelyo solution containing BHB, MLT and PVP also exhibited two baseline shifts, first at ~−69° C. and second at ~−52° C. and an ice melting endotherm at ~−12° C. Interestingly, the thermal event at ~−27° C., observed in the MLT-PVP solution was not discernible. Thus the BHB in solution appeared to govern the thermal behavior of the final prelyo solution. Moreover, the BHB remains amorphous in the freeze-concentrate.

In frozen solutions, the solute may exist either in the crystalline or amorphous state. When the solute is amorphous, in order to avoid product collapse, the primary drying should ideally be conducted below the Tg'. However, if the solute crystallizes, product meltback can be avoided by conducting the primary drying below the eutectic temperature. Since the eutectic temperature >>Tg', solute crystallization in the frozen solution enables primary drying at an elevated temperature and, therefore, increases the efficiency of the freeze-drying cycle.

BHB solution, when lyophilized alone, yielded a crystalline lyophile. In this case, BHB crystallized in the frozen state and BHB—ice eutectic temperature was −32° C. (FIG. 16). BHB crystallization was enabled only when the frozen solution was heated at a slow rate of 0.1 C/min. It was of interest to establish if BHB crystallization could be enabled in the presence of PVP and MLT. Two approaches to cause BHB crystallization were investigated. (i) Heating the frozen solution at a very slow rate (down to 0.1° C./min). However, there was no evidence of BHB crystallization. (FIG. 16). (ii) Annealing the frozen solution above the glass transition temperature but below the eutectic temperature. Annealing induced solute crystallization would become evident from the disappearance of Tg'. Annealing at −35° C. for 12 hours did not induce BHB crystallization. This conclusion was based on both DSC and low temperature XRD (FIGS. 17 and 18).

These results suggest that, in the presence of PVP and MLT, BHB remained amorphous in the freeze concentrate and crystallized only during drying. PVP is known to be a crystallization inhibitor and was effective in retaining BHB in the amorphous state in the frozen solution.

Example 11—Freeze Drying Cycle—Development and Optimization

The low glass transition temperature of the prelyo solution necessitated drying to be initiated at a low temperature. The freeze-drying cycle (fast freezing using liquid nitrogen; primary drying initiated at −25° C.; final secondary drying at 25° C.) yielded a lyophile with an unacceptably long reconstitution time of ~30 minutes. Therefore, the freeze-drying cycle was modified. The prelyo solution was cooled slowly and the primary drying was started at −40° C. (100 mTorr), and the temperature was sequentially increased with the final drying at 40° C. This high temperature was necessitated by the hygroscopic nature of PVP. This optimized cycle yielded a lyophile with a reconstitution time of ~2 min.

Example 12—Lyophile Characterization

Figure 12A:
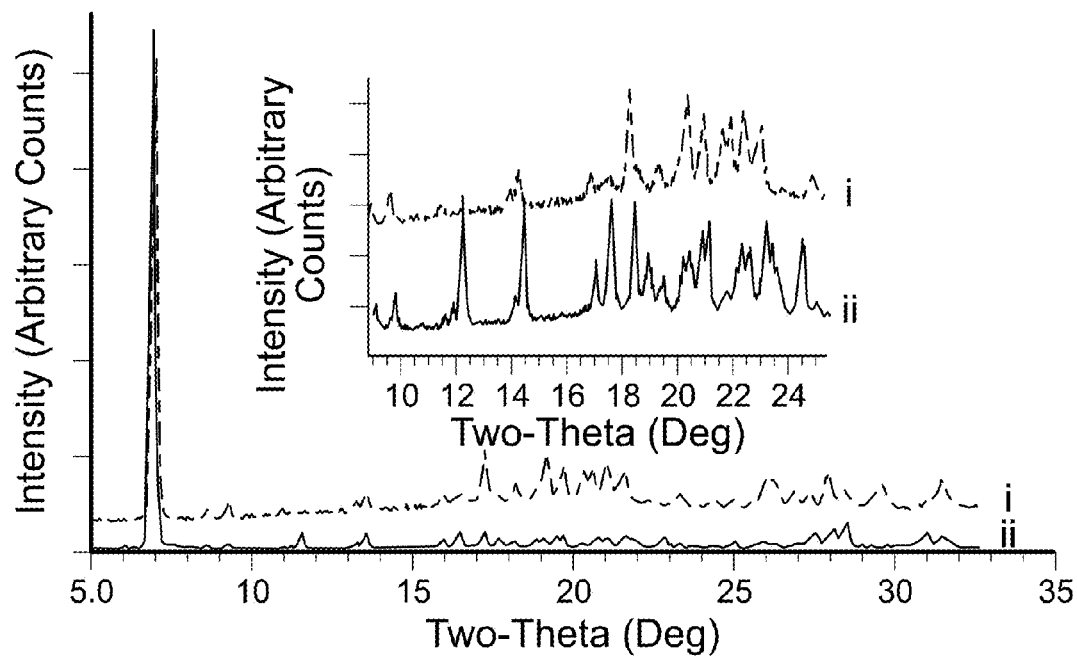
FIG. 12A is a graph showing XRD patterns of BHB-MLT-PVP lyophile (line i). The corresponding data for BHB (line ii) is provided to enable ready comparison. The inset shows XRD patterns expanded in the 10-24° 2θ range.
Figure 12B:
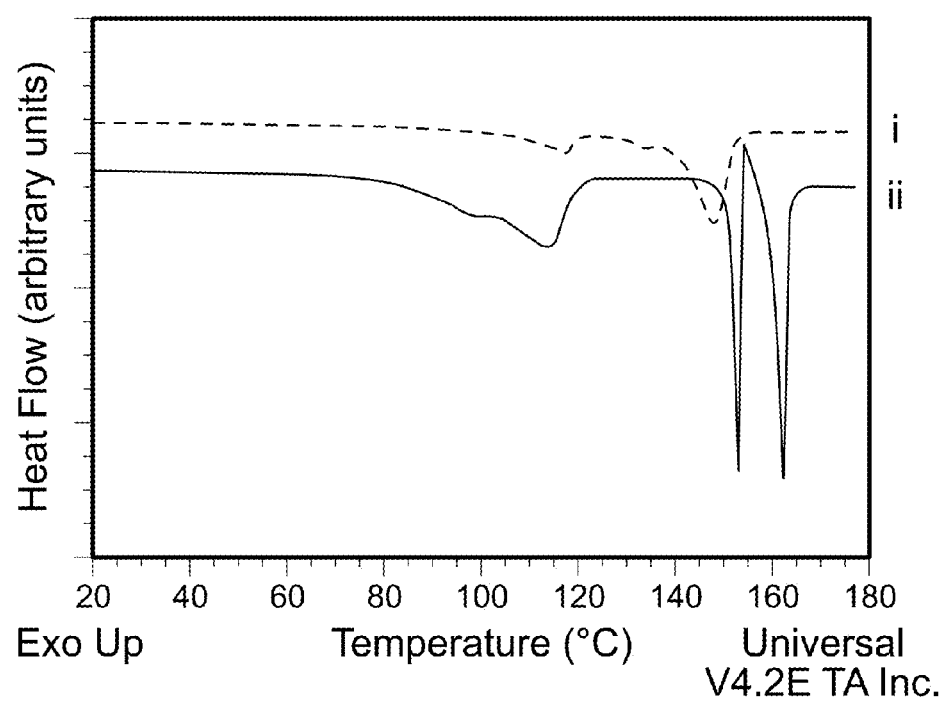
FIG. 12B is a graph showing DSC heating curves of BHB-MLT-PVP lyophile (line i). The corresponding data for BHB (line ii) is provided to enable ready comparison.

The water content in the final lyophile, determined by Karl Fischer titremetry and TGA, was ~3% w/w. The XRD patterns of BHB and the final lyophile, presented in FIG. 12A, are almost superimposable. This suggests that BHB crystallized as BHB·0.25$H_2O$ in the lyophile. A halo in the background of the lyophile can be attributed to the PVP (weight fraction ~0.28 in the lyophile). No characteristic peaks of MLT were discernible. It had earlier been observed that MLT hydrogen bonds with PVP and is retained amorphous (FIG. 7). Moreover, the weight fraction of MLT in the final lyophile is very low (~0.01). The DSC heating curve of the lyophile is presented in FIG. 12B. The endotherm from 100 to 125° C. can be attributed to water loss since, in this temperature range, weight loss was observed in the TGA. Clearly, the two high temperature endotherms of BHB are absent and, instead, a single broader endotherm at ~148° C. is observed. Thus, the presence of PVP appears to alter the thermal behavior of BHB.

Example 13—In Vivo Assessment of the BHB-MLT-PVP Solution

Figure 13:
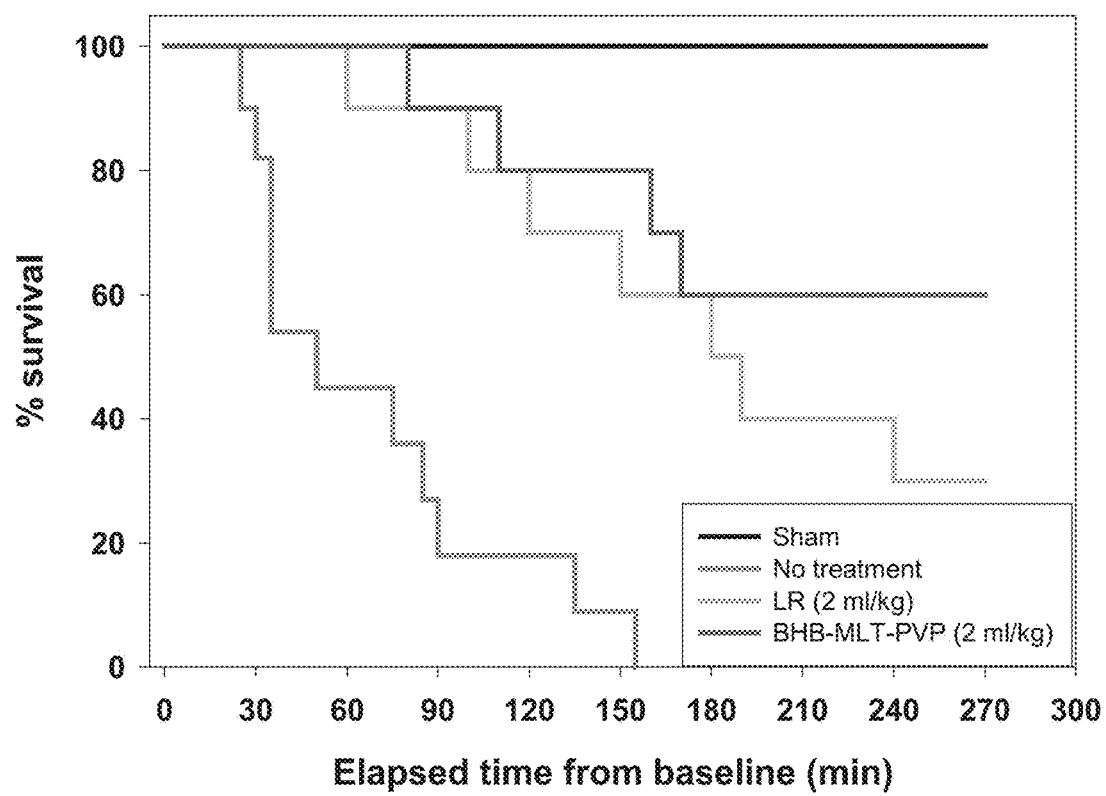
FIG. 13 is a Kaplan-Meier Survival curve of rats subjected to 40% blood loss and treated with BHB-MLT-PVP, or LR solution (untreated and sham animals served as controls). MLT-PVP lyophiles were prepared and BHB powder was added immediately before reconstitution. The solutions were prepared on the day of the experiment (final pH 7.4).

The ability of the formulation to improve survival was tested in a rat model of hemorrhagic shock (FIG. 13). Rats were subjected to 40% blood loss, and were treated with a 2 ml/kg bolus of BHB (2M)-MLT (21.5 mM)-PVP (40 mM) or lactated Ringer's (LR) solution. All the sham animals survived until the end of the experiment (FIG. 13). All rats subjected to blood loss but with no further treatment expired before the end of the experiment, with a mean survival time of 71.5 minutes. The highest survival was observed in the rats treated with BHB-MLT-PVP (6/10), followed by treatment with lactated Ringer's solution (3/10). Survival was significantly lower in untreated rats when compared to those receiving LR or BHB-MLT-PVP (p≤0.002).

Thus, the BHB-MLT-PVP formulation was effective in improving survival in a rat model of hemorrhagic shock. The difference between the BHB-MLT-PVP formulation and LR was not significant in improving survival (p=0.305). However, the higher rate of survival (60% vs 30%) and the longer mean survival time (213 min vs 181 min) indicates that this can serve as a promising first line of treatment (e.g., in the battlefield or at an accident site) that extends the survival time until the patient is transported to the hospital.

Figures 14A, 14B:
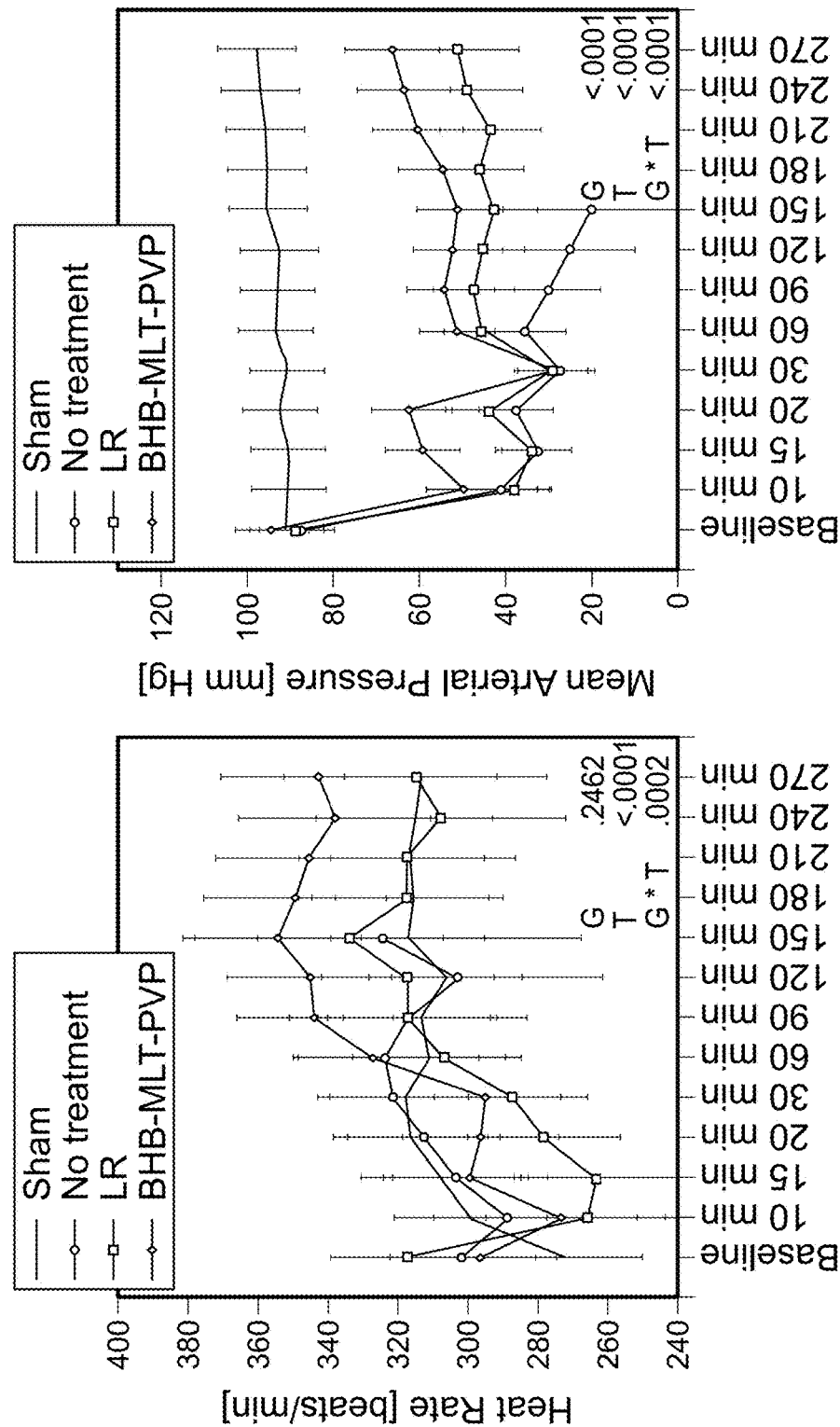
FIG. 14A is a graph showing Heart Rate in rats subjected to 40% blood loss and treated with BHB-MLT-PVP or LR solution (untreated and sham animals served as controls). Data presented as least-squares means with 95% confidence intervals. G—Group effect, G*T—Group*Time interaction effect, T—Time effect.
FIG. 14B is a graph showing Mean Arterial Pressure in rats subjected to 40% blood loss and treated with BHB-MLT-PVP or LR solution (untreated and sham animals served as controls). Data presented as least-squares means with 95% confidence intervals. G—Group effect, G*T—Group*Time interaction effect, T—Time effect.

The heart rate (HR) and the mean arterial pressure (MAP) provided a physiological measure of the state of the animals during the entire course of the experiment (FIG. 14). The heart rate decreased at the beginning of the blood removal phase but increased throughout the experiment (FIG. 14A). The increase was more prominent in the BHB-MLT-PVP group, and heart rate exceeded baseline levels during the second half of the experiment. At the individual time points, there were no significant differences between the groups. MAP remained stable in sham animals throughout and was significantly higher than in the other groups during the first 4 hours of the experiment. As expected, MAP sharply decreased during the blood removal phase, with the lowest pressure observed after the last blood draw (30 min). Infusion of BHB-MLT-PVP (bolus infusion at 14 min) transiently increased MAP, resulting in significantly higher blood pressure than in the LR and the untreated group. Upon completion of blood withdrawal (30 min), MAP started increasing in the groups receiving LR or BHB-MLT-PVP. This effect was more prominent in the BHB-MLT-PVP group, although the differences were not significant. The increase in blood pressure is likely a result of the high osmolarity of the BHB-MLT-PVP formulation. Infusion of hyperosmolar solutions creates an osmotic gradient which mobilizes intracellular fluids, thereby increasing intravascular volume and improving tissue perfusion. This short term anti-ischemic effect of BHB-MLT-PVP likely acts synergistically with the metabolic and antioxidant effects of the treatment. The high osmolality of this formulation did not have any adverse in vivo effects.

Part II—Resuscitation Composition

Part A—Preliminary Results

Example 14—Methods of Making a Resuscitation Composition 43 mM melatonin was dissolved in a solution of 20% PVP or 10% HPbCD/5% PEG400/5% PVP K12 and lyophilized. BHB powder was added to the lyophilized melatonin powder, and the solution was dissolved by adding water/HCl to a final concentration of 2 M BHB/21.5 mM melatonin/10% PVP or 2 M BHB/21.5 mM melatonin/5% HPbCD/2.5 PVP K12/2.5% PEG400, respectively. The pH was adjusted to 7.4.

Example 15—In Vitro Hemolysis by a Resuscitation Composition

To test induction of in vitro hemolysis, 1 ml/kg of each solution (BHB/M/DMSO; BHB/M/PVP; or BHB/M/HPbCD/PVP/PEG; FIG. 19A) or 2 ml/kg of each solution (BHB/M/DMSO; BHB/M/PVP; or BHB/M/HPbCD/PVP/PEG; FIG. 19B) were incubated with human full blood (ratio 1:10) for one minute before quenching with PBS and centrifugation. Percent in vitro hemolysis was calculated as hemoglobin absorbance in the supernatant of the sample versus positive control (10% triton X-100).

These results demonstrated that in vitro hemolysis was significantly higher in the solution containing 4 M BHB/43 mM M/20% DMSO than in those containing 4 M BHB/43 mM M/10% HPbCD/5% PVP/5% PEG or 4 M BHB/43 mM M/20% PVP (1×; FIG. 19A). The same pattern was observed for solutions containing 2 M BHB/21.5 mM M (0.5×; FIG. 19B). BHB/M/HPbCD/PVP/PEG consistently showed the lowest in vitro hemolysis induction.

Example 16—Materials and Methods for Inducing Hemorrhagic Shock

Rats were exposed to gradual withdrawal of 40% total blood volume over 30 mins, followed by a four-hour shock interval. Treatment solutions were administered intravenously halfway throughout blood withdrawal. Treatment groups are shown in Table 1 (n=10 for all groups except for the no treatment, which was n=11).

As shown in Table 1, all animals received the same dose of BHB and M. Survival was analyzed, as well as blood pressure, heart rate, free plasma hemoglobin, blood gases and markers of organ injury.

TABLE 1

| Treatment Group | Designation | Dose |
|---|---|---|
| No treatment | — | — |
| Lactated Ringer's solution | LR | 1 ml/kg |
| 4M BHB/43 mM melatonin/20% DMSO | 1X BMB/M/DMSO | 1 ml/kg |
| 2M BHB/21.5 mM melatonin/10% DMSO | 0.5X BHB/M/DMSO | 2 ml/kg |
| 2M BHB/21.5 mM melatonin/10% PVP | 0.5X BHB/M/PVP | 2 ml/kg |
| 2M BHB/21.5 mM melatonin/5% HPbCD/ 2.5% PVP/2.5% PEG 400 | 0.5X BHB/M/HPbCD | 2 ml/kg |
| Instrumentation only | — | — |

Example 17—Results from Induction of Hemorrhagic Shock

FIG. 20 shows that there was a significant difference in survival between the treatment groups. Survival rate was highest for the BHB/M/HPbCD/PVP/PEG-treated rats, followed by BHB/M/PVP-treated rats, 0.5× and 1× BHB/M/DMSO, LR and no treatment. The overall p-value for these experiments was <0.0001; the p-value vs. no treatment was <0.0002; the p-value for LR vs BHB/M/HPbCD/PVP/PEG was 0.018; and the p-value for all other comparisons was >0.05.

Blood pressure, heart rate, blood gases and markers of organ injury did not differ significantly between BHB/M-treated groups throughout the experiment.

These results show that rats receiving BHB/M solutions experienced significantly higher survival than those not receiving treatment. Surprisingly, there was a trend towards higher efficacy in the BHB/M/HPbCD/PVP/PEG formulation, and also in the BHB/M/PVP formulation, when compared to the original formulation containing DMSO (i.e., BHB/M/DMSO). Also surprisingly, treatment with BHB/M/HPbCD/PVP/PEG resulted in significantly higher survival than treatment with the standard of care (LR), an effect even more prominent than was observed for the original BHB/M/DMSO solution, which itself was surprising. These findings indicate that replacing DMSO with HPbCD/PVP/PEG in the formulation may result in significantly higher efficacy, particularly in the clinical setting.

Example 18—In Vivo Hemolysis Induction by a Resuscitation Composition

Upon completion of blood withdrawal, free plasma hemoglobin, a measure of in vivo hemolysis was significantly lower in either the BHB/M/HPbCD/PVP/PEG formulation or the BHB/M/PVP formulation than in 1× BHB/M/DMSO rats, and lower in the BHB/M/PVP animals than in 0.5× BHB/M/DMSO animals. See FIG. 21.

These results demonstrate that BHB/M/DMSO causes hemolysis in vivo at levels higher than those observed for either the BHB/M/HPbCD/PVP/PEG formulation or the BHB/M/PVP formulation. Since hemolysis can cause anemia and other adverse effects, the BHB/M/HPbCD/PVP/PEG formulation or the BHB/M/PVP formulation (i.e., without DMSO) may exert an improved safety profile in the clinical setting.

Part B—Evaluation of Novel Formulations of BHB and Melatonin in a Rat Model of Hemorrhagic Shock Example 19—General Materials and Methods D-β-hydroxybutyrate was purchased from Sigma Aldrich (St. Louis, Mo.) and Lonza (Basel, Switzerland). Melatonin was generously provided by Flamma S.p.A. (Chignolo, Italy). Dimethyl sulfoxide (DMSO) was purchased from Alfa Aesar (Ward Hill, Mass.), polyvinylpyrrolidone K12 (PVP) from Acros Organics (Geel, Belgium), polyethylene glycol 400 (PEG) from Spectrum Chemical (New Brunswick, N.J.). All other chemicals were purchased from Sigma Aldrich (St. Louis, Mo.).

Example 20—Solution Preparation for Injection

BHB/M/DMSO solutions: On the day of the experiment, appropriate amounts of melatonin solution (DMSO as vehicle) and aqueous solution of BHB (pH 7.4) were mixed to achieve final solution containing either 4M BHB/43 mM Melatonin/20% DMSO or 2M BHB/21.5 mM Melatonin/10% DMSO.

BHB/M/Exp solution: As the lyophilization cycle had not been optimized at the time of the in vivo experiments, 21.5 mM melatonin was dissolved in aqueous solution of 5% HPβCD/2.5% PVP/2.5% PEG and lyophilized. On the day of the experiment, dry BHB powder was added to the lyophile immediately before reconstitution. This mix was reconstituted with water to obtain a solution containing 2M BHB/21.5 mM Melatonin/5% HPβCD/2.5% PVP/2.5% PEG. The method of preparation of BHB/M/PVP is as described herein.

All solutions were filtered through a 0.2 μm syringe filter for sterilization before injection.

Example 21—Anesthesia and Instrumentation for Hemorrhagic Shock Model

An overview of the experimental protocol is given in FIG. 22. All animal experiments were approved by the Institutional Animal Care and Use Committee of the University of Minnesota and carried out in accordance with AAALAC regulations. Seventy-one male Sprague-Dawley rats (350-375 g, Envigo) were housed on a 12-hour light dark cycle with water and food ad libitum. The rats were allowed to adapt to their environment for at least seven days before the procedure. On the day of the experiment, rats were anesthetized in an induction chamber with isoflurane (5% in 1 l/min oxygen), treated with meloxicam for analgesia (0.5 mg, s.c.), and placed on a heating pad to maintain a target body temperature of 37±0.5° C. throughout the experiment (measured via rectal thermometer). Anesthesia was maintained with isoflurane via nose cone (1-2% in 1 l/min oxygen, Surgivet Isotec 4, Smiths Medical PM, Inc, Norwell, Mass.). The right external jugular vein was aseptically exposed and cannulated with sterile PE 160 tubing for blood drawing and treatment administration. The left femoral artery was aseptically exposed and cannulated with a 24G catheter for continuous heart rate and blood pressure measurements.

Example 22—Hemorrhagic Shock and Infusion Protocol

After instrumentation, rats were allowed to stabilize for ten minutes, after which baseline measurements were taken. Immediately after baseline sampling, blood was gradually withdrawn in three steps to achieve a total loss of 40% of the total blood volume over 30 minutes (FIG. 22). Total blood volume was calculated as 7% of body weight. Fourteen minutes after baseline measurements, half-way throughout blood withdrawal, treatment was administered as a 1 ml/kg or 2 ml/kg intravenous bolus over 1 minute (Table 2). Lines were flushed with lactated Ringer's solution (LR) after blood draws and solution administration. Animals that survived until the end of the experiment were maintained anesthetized until they were euthanized via exsanguination after the last sampling point (270 min). Sham rats were instrumented only, no treatment bolus was administered and no blood was withdrawn other than for blood gas analysis at baseline and for blood gas and organ marker analysis at the end of the experiment.

TABLE 2

| Treatment Groups | | | | | | | | | |
|---|---|---|---|---|---|---|---|---|---|
| Treatment Group | BHB | Melatonin | DMSO Concentration | PVP | HPβCD | PEG | Volume | BHB/M Dose | n |
| Sham | — | — | — | — | — | — | — | — | 10 |
| No Treatment | — | — | — | — | — | — | — | — | 11 |
| LR | — | — | — | — | — | — | 2 ml/kg | — | 10 |
| 4M BHB/M/DMSO | 4M | 43 mM | 20% | — | — | — | 1 ml/kg | 4 mmol BHB/kg | 10 |
| 2M BHB/M/DMSO | 2M | 21.5 mM | 10% | — | — | — | 2 ml/kg | | 10 |

TABLE 2-continued

| Treatment Group | Treatment Groups | | | | | | | | |
|---|---|---|---|---|---|---|---|---|---|
| | BHB | Melatonin | DMSO Concentration | PVP | HPβCD | PEG | Volume | BHB/M Dose | n |
| BHB/M/PVP | 2M | 21.5 mM | — | 10% | — | — | 2 ml/kg | | 10 |
| BHB/M/Exp | 2M | 21.5 mM | — | 2.5% | 5% | 2.5% | 2 ml/kg | | 10 |

Sham rats were exposed to instrumentation only, no bolus was administered and no blood was withdrawn other than for blood gas analysis at baseline and for blood gas and organ marker analysis at the end of the experiment.
All treatments were delivered as an intravenous bolus over 1 minute.

Example 23—Hemodynamic and Physiologic Measurements

Blood pressure and heart rate were measured continuously throughout the experiment with a Spacelab monitor (Spacelabs Healthcare, Snoqualmie, Wash.). At baseline, at the end of blood removal (30 min) and at the end of the experiment (270 min), venous blood samples were drawn for analysis via blood gas analyzer (Gem Premier 3000, Instrumentation Laboratory Co, Bedford, Mass.) and to measure markers of organ function (including alkaline phosphatase, alanine aminotransferase (ALT), aspartate aminotransferase (AST), creatinine and urea nitrogen). Free plasma hemoglobin, a marker of in vivo hemolysis, was measured photometrically at the end of the shock period (30 min). Organ function markers and free plasma hemoglobin were analyzed in the Clinical Laboratory Improvement Amendments-certified Fairview Diagnostics Laboratory.

Example 24—Melatonin and BHB Serum Concentrations

BHB and melatonin serum concentrations were analyzed at baseline, at the end of the bolus infusion and immediately before sacrifice. Blood samples were allowed to clot at room temperature for 30 minutes before centrifugation (1150 g, 10 min, 4° C.) and collection of serum. Melatonin and BHB serum concentrations were measured as previously described. Briefly, the samples were extracted with acetonitrile and dried under nitrogen. For melatonin quantification, the sample was dissolved in a 1:1 mix of water and methanol with 0.1% formic acid. Melatonin was quantified via ultra-high-performance liquid chromatography-coupled mass spectrometry (UPLC-MS, limit of quantitation $5 \times 10^3$ pg/ml). For BHB analysis, samples were derivatized with N,O-Bis(trimethylsilyl)trifluoroacetamide: pyridine (5:1) and then analyzed via gas chromatography-coupled mass spectrometry (GC-MS, limit of detection 0.048 mM).

Example 25—In Vitro Hemolysis

In vitro hemolysis quantification was modified from (Fort et al., 1984, J. Parenter. Sci. Technol., 38:82-7). 50 µl of test solution and 450 µl of fresh heparinized human whole blood were gently mixed and incubated for 60 seconds, after which the solution was quenched with 10 ml isotonic PBS. Isotonic PBS was used as nonhemolytic control; 10% Triton X 100 was used as positive control (ASTM E2524-08). Solutions were centrifuged (1500 g, 25° C., 15 min) and supernatant was transferred to a clear 96-well plate (200 µl/well, triplicates). Absorbance (Abs) was measured at 540 nm and hemolysis was calculated as follows:

$$\% \text{ Hemolysis} = \left( \frac{\text{Abs}_{sample} - \text{Abs}_{PBS}}{\text{Abs}_{Triton \times 100} - \text{Abs}_{PBS}} \right) \times 100$$

Initial experiments showed that at the dilutions used in these experiment, none of the tested compounds changed the absorbance spectrum of hemoglobin.

Example 26—Lyophilization of BHB/M/Exp Solution

Melatonin was dissolved overnight in a solution containing 10% HPβCD/5% PVP/5% PEG. Equal volumes of 43 mM melatonin solution and 4M BHB (adjusted to pH 7.4) solution were mixed to prepare the BHB/M/Exp solution.

The solution was filled into 10 mL glass vials (2 mL fill volume), covered with rubber stopper (20 mm, 2 Leg Lyo, Gry Butyl Sil, Wheaton) and loaded into the lyophilizer. Lyophilization was carried out in a bench top freeze-dryer (VirTis AdVantage, Gardiner, N.Y.). The shelf was cooled to −60° C. at 0.25° C./min and held for 8 h. Primary drying was sequentially conducted at −40° C. (24 h), −30° C. (24 h), and −20° C. (12 h) at 100±25 mTorr. During secondary drying, the shelf was progressively heated to −10° C., 0° C., +10° C. and +25° C. and held at each temperature for 12 h while at +40° C. held for 24 h. The samples were dried under vacuum for 48 hrs. At the end of the cycle, the vials were stoppered and stored in a desiccator containing anhydrous calcium sulfate at −20° C.

Example 27—Differential Scanning Calorimetry

A differential scanning calorimeter (Q2000, TA Instruments, New Castle, Del.) equipped with a refrigerated cooling accessory was used. Dry nitrogen gas was purged at 50 mL/min. For thermal analysis of the prelyophilization solution, ~20 µL of solution was weighed in an aluminum pan, sealed hermetically, cooled from RT to −90° C. at 1° C./min, held for 30 min and heated to RT at 10° C./min. In case of lyophiles, the powder was filled into the aluminum pan at RT (in a glove box under nitrogen purge; RH≤5%), sealed non-hermetically, and heated from RT to 180° C., at 10° C./min.

Example 28—X-Ray Diffractometry

Powder samples were exposed, at room temperature, to Co Kα radiation (1.78899 Å; 40 kV×35 mA) in a two-dimensional X-ray diffractometer (D8-Discover fitted with a Vantec 500 detector, Bruker). XRD patterns were collected using a 0.8 mm collimator, the sample to detector distance was kept at 20 cm. Two measurement frames were scanned at 20/10 and 40/10° θ/ω, respectively. Area detector images were finally converted to one-dimensional intensity vs. 2θ data sets by using an averaging integration algorithm. JADE 2010 was used to convert pattern to Cu as radiation source.

Example 29—Statistical Analysis

Kaplan-Meier analysis with Generalized Wilcoxon test was used to analyze survival differences between groups.

Non-longitudinal data were analyzed via Kruskal-Wallis test with Dunn-Bonferroni corrections and are reported as medians with interquartile ranges (IQR). Longitudinal parameters were analyzed using the Proc Mixed procedure in SAS Version 9.4 software (SAS Institute, Inc., Cary, N.C.). Group, Time and Group*Time Interaction were modeled as fixed effects. The models used compound symmetry (CS) or autoregressive (AR(1)) covariance structure (selection based on the model with the lowest Bayesian Information Criterion value) and the between-within method for degrees of freedom. Normality of distributions of residuals of the final models was assessed using scatter and quantile-quantile plots. For parameters with significant interaction effects, differences at individual time points were analyzed by pairwise comparisons with Tukey adjustments. Longitudinal data is presented as least-squared means with 95% confidence intervals.

Example 30—Physiology Results

Mean arterial pressure and heart rate were measured throughout the experiment (FIG. 23). Rats exposed to hemorrhage experienced a sharp drop in mean arterial pressure upon the beginning of blood removal (FIG. 23A). Infusion of BHB/M, but not LR transiently increased mean arterial pressure, however, mean arterial pressure was similar in all hemorrhaged groups at the end of the blood removal phase. Mean arterial pressure increased once blood withdrawal was completed but remained below baseline levels until the end of the experiment. Mean arterial pressure remained stable in the sham group and was significantly higher than in all hemorrhaged groups during the first three hours after the completion of blood withdrawal.

Although there was a significant interaction effect for heart rate, there were no significant differences between groups at individual time points (FIG. 23B). Heart rate decreased after the first blood draw and then increased throughout the experiment, an effect that was most prominent in the BHB/M-treated groups. No significant group or interaction effect was observed for body temperature (G p=0.8587, T p<0.0001, G*T p=0.2916).

Example 31—Survival Results

All sham animals survived until the end of the experiment, while all rats exposed to blood loss without treatment died within three hours of baseline measurements (FIG. 24). The highest survival was observed in rats treated with BHB/M/Exp (8/10), followed by rats receiving BHB/M/PVP (6/10), 4M BHB/M/DMSO (5/10) and 2M BHB/M/DMSO (5/10) and those treated with LR (3/10). Survival was significantly lower in untreated rats than in the LR and each of the BHB/M groups (p≤0.002). There was no significant difference in survival between the BHB/M-treated groups. Survival in BHB/M/Exp-treated rats was not significantly different from the sham group (p=0.147), but was significantly higher when compared to the LR group (p=0.018).

Example 32—Drug Serum Concentrations

To test the effects of solution formulation on systemic drug levels, serum levels of melatonin and BHB were quantified at baseline, after bolus infusion and at the end of the experiment. BHB and melatonin serum concentrations peaked after bolus infusion and returned close to baseline levels by the end of the experiment in BHB/M-infused animals. Drug serum concentrations remained at baseline levels in untreated rats and in those receiving LR (FIG. 25). After bolus infusion, BHB and melatonin levels were significantly higher in the groups receiving solutions containing BHB/M than in untreated rats or those infused with LR. BHB serum levels were significantly higher in the BHB/M/PVP than in the 2M BHB/M/DMSO group after the bolus infusion (FIG. 25A, p=0.0283). Melatonin serum levels did not differ significantly between the BHB/M-treated groups (FIG. 25B).

Example 33—Blood Gases and Markers of Organ Function

Blood gases and various markers of organ function were analyzed at baseline, at the end of blood withdrawal and at the end of the experiment (Table 3). Changes in blood gases in BHB/M treated rats were similar to those previously observed after the infusion of BHB and melatonin in porcine hemorrhagic shock. BHB/M-infusion resulted in significantly increased blood sodium levels at the end of blood withdrawal, along with decreased potassium concentrations. This was likely a direct effect of the BHB/M infusion, which is administered as a sodium salt. BHB/M and LR infusion attenuated a shock-induced increase in blood lactate levels and decreases in blood pH and base excess, however, these effects were more prominent after BHB/M treatment.

Total hemoglobin levels were significantly decreased in hemorrhaged animals at the end of the experiment, with no differences between rats receiving LR and those treated with BHB/M solutions. Infusion of BHB/M, but not LR attenuated a hemorrhage-induced decrease in venous oxygen saturation.

Hemorrhage-induced increases was observed in serum levels of various markers of liver (ALT, AST) and kidney function (BUN and creatinine) at the end of the experiment independent of treatment group. Alkaline Phosphatase did not change significantly throughout the experiment. Blood glucose and calcium concentrations did not differ significantly at individual time points.

There were no significant differences among the four BHB/M formulations for any of the blood markers tested throughout the experiment.

TABLE 3

| Blood Gases and markers of organ function in Rats Exposed to 40% blood loss and treated with LR or different formulations of BHB/M | | | | |
|---|---|---|---|---|
| Parameter | Baseline | S 30 min | S 270 min | Effects |
| Na$^+$ [mEq/l] | | | | |
| Sham | 138.2 (135.4-141.0) | | 138.4 (135.7-141.2) | G .0588 |
| No Treatment | 137.2 (134.6-139.8) | 134.5 (131.9-137.2) | | T <.0001 |
| LR | 134.0 (131.4-136.7) | 132.2 (129.4-134.9) | 137.8 (132.9-142.7) | G*T .0138 |
| 4M BHB/M/DMSO | 137.6 (135.0-140.3) | 139.2 (136.6-141.9)# | 139.6 (136.3-143.0) | |

TABLE 3-continued

Blood Gases and markers of organ function in Rats Exposed to
40% blood loss and treated with LR or different formulations of BHB/M

| Parameter | Baseline | S 30 min | S 270 min | Effects |
|---|---|---|---|---|
| 2M BHB/M/DMSO | 138.0 (135.4-140.7) | 139.7 (136.9-142.4)# | 143.4 (140.0-146.8) | |
| BHB/M/PVP | 135.5 (132.9-138.2) | 138.3 (135.7-141.0) | 140.3 (137.1-143.4) | |
| BHB/M/Exp | 137.0 (134.0-140.0) | 139.9 (136.9-142.8)# | 141.5 (138.4-144.6) | |
| $K^+$ [mEq/l] | | | | |
| Sham | 4.34 (3.64-5.05) | | 5.17 (4.47-5.87) | G .0055 |
| No Treatment | 4.72 (4.06-5.39) | 6.02 (5.36-6.69) | | T<.0001 |
| LR | 4.17 (3.51-4.84) | 5.25 (4.55-5.95) | 6.60 (5.12-8.09) | G*T .0689 |
| 4M BHB/M/DMSO | 4.34 (3.68-5.01) | 4.45 (3.79-5.12) | 5.02 (4.08-5.96) | |
| 2M BHB/M/DMSO | 4.38 (3.72-5.05) | 4.23 (3.53-4.93) | 6.43 (5.49-7.37) | |
| BHB/M/PVP | 4.28 (3.62-4.95) | 4.28 (3.62-4.95) | 6.18 (5.32-7.04) | |
| BHB/M/Exp | 4.30 (3.56-5.04) | 4.10 (3.36-4.84) | 5.14 (4.35-5.94) | |
| pH | | | | |
| Sham | 7.32 (7.26-7.38) | | 7.24 (7.17-7.30) | G <.0001 |
| No Treatment | 7.31 (7.25-7.37) | 7.06 (7.00-7.12) | | T <.0001 |
| LR | 7.36 (7.29-7.42) | 7.18 (7.12-7.25) | 7.12 (6.99-7.25) | G*T <.0001 |
| 4M BHB/M/DMSO | 7.37 (7.31-7.43) | 7.35 (7.28-7.41)^ | 7.37 (7.28-7.45) | |
| 2M BHB/M/DMSO | 7.35 (7.29-7.41) | 7.35 (7.28-7.41)^ | 7.20-7.12-7.29) | |
| BHB/M/PVP | 7.35-(7.29-7.41) | 7.35 (7.29-7.41)^# | 7.33 (7.25-7.41) | |
| BHB/M/Exp | 7.36 (7.29-7.43) | 7.36 (7.29-7.43)^# | 7.35 (7.28-7.43) | |
| Base Excess | | | | |
| Sham | 1.3 (−1.0-3.7) | | 0.5 (−1.9-2.8) | G <.0001 |
| No Treatment | 2.4 (0.2-4.6) | −8.1 (−10.5--5.8) | | T <.0001 |
| LR | 3.6 (1.4-5.9) | −4.7 (−7.1--2.4) | −4.6 (−9.5-0.3) | G*T <.0001 |
| 4M BHB/M/DMSO | 3.2 (1.0-5.4) | 2.4 (0.2-4.6)^# | 4.2 (1.0-7.3) | |
| 2M BHB/M/DMSO | 2.7 (0.5-5.0) | 2.8 (0.5-5.2)^# | 4.7 (1.2-8.1) | |
| BHB/M/PVP | 3.4 (1.1-5.6) | 2.9 (0.7-5.1)^# | 2.3 (−0.5-5.2) | |
| BHB/M/Exp | 4.7 (2.2-7.2) | 3.4 (0.9-5.9)^# | 3.9 (1.2-6.5) | |
| Lactate [mg/dl] | | | | |
| Sham | 3.3 (1.9-4.7) | | 2.0 (0.6-3.4) | G .0006 |
| No Treatment | 2.0 (0.7-3.4) | 9.4 (8.0-10.7) | | T <.0001 |
| LR | 1.8 (0.5-3.1) | 6.6 (5.2-8.0)^ | 2.1 (−0.9-5.1) | G*T <.0001 |
| 4M BHB/M/DMSO | 1.9 (0.5-3.2) | 3.7 (2.4-5.1)^ | 3.6 (1.8-5.5) | |
| 2M BHB/M/DMSO | 1.8 (0.5-3.1) | 3.3 (1.8-4.7)^ | 6.3 (4.4-8.2)* | |
| BHB/M/PVP | 2.0 (0.7-3.3) | 3.6 (2.3-4.9)^ | 4.6 (2.8-6.3) | |
| BHB/M/Exp | 1.2 (−0.3-2.7) | 2.8 (1.3-4.3)^# | 3.7 (2.1-5.3) | |
| Glucose [mg/dl] | | | | |
| Sham | 316 (268-364) | | 202 (154-250) | G .2353 |
| No Treatment | 353 (308-399) | 483 (437-528) | | T <.0001 |
| LR | 316 (270-361) | 475 (427-523) | 116 (15-217) | G*T .7572 |
| 4M BHB/M/DMSO | 306 (261-352) | 457 (411-502) | 254 (190-318) | |
| 2M BHB/M/DMSO | 324 (278-369) | 466 (418-514) | 229 (165-293) | |
| BHB/M/PVP | 318 (273-364) | 449 (403-494) | 209 (151-268) | |
| BHB/M/Exp | 290 (239-341) | 424 (373-475) | 190 (136-244) | |
| $Ca^{2+}$ [mEq/l] | | | | |
| Sham | 1.16 (1.07-1.25) | | 1.23 (1.14-1.33) | G .2888 |
| No Treatment | 1.15 (1.07-1.24) | 1.17 (1.08-1.26) | | T .0010 |
| LR | 1.17 (1.08-1.25) | 1.11 (1.02-1.21) | 1.00 (0.83-1.18) | G*T .0421 |
| 4M BHB/M/DMSO | 1.14 (1.06-1.23) | 1.09 (1.00-1.17) | 1.03 (0.91-1.15) | |
| 2M BHB/M/DMSO | 1.18 (1.09-1.26) | 1.09 (1.00-1.18) | 1.15 (1.04-1.27) | |
| BHB/M/PVP | 1.26 (1.17-1.35) | 1.13 (1.04-1.22) | 1.07 (0.96-1.18) | |
| BHB/M/Exp | 1.17 (1.07-1.26) | 1.04 (0.94-1.14) | 1.01 (0.91-1.12) | |
| Hemoglobin [g/dl] | | | | |
| Sham | 11.8 (11.1-12.6) | | 11.0 (10.2-11.7) | G <.0005 |
| No Treatment | 11.7 (11.0-12.4) | 8.1 (7.4-8.8) | | T <.0001 |
| LR | 12.0 (11.3-12.7) | 7.6 (6.9-8.4) | 6.3 (4.9-7.6)* | G*T .0001 |
| 4M BHB/M/DMSO | 12.6 (11.9-13.3) | 8.5 (7.8-9.2) | 6.8 (5.9-7.7)* | |
| 2M BHB/M/DMSO | 12.6 (11.8-13.3) | 8.0 (7.3-8.8) | 6.8 (5.9-7.8)* | |
| BHB/M/PVP | 12.2 (11.5-12.9) | 8.1 (7.4-8.8) | 7.0 (6.1-7.8)* | |
| BHB/M/Exp | 12.5 (11.7-13.2) | 8.0 (7.2-8.8) | 6.6 (5.8-7.4)* | |
| % $SvO_2$ | | | | |
| Sham | 88.6 (79.1-98.0) | | 85.9 (76.5-95.3) | G .0001 |
| No Treatment | 77.3 (68.4-86.2) | 19.1 (9.8-28.5) | | T <.0001 |
| LR | 86.7 (77.8-95.6) | 29.5 (20.1-38.9) | 56.2 (37.4-75.0) | G*T .0012 |
| 4M BHB/M/DMSO | 88.8 (79.9-97.7) | 49.2 (40.3-58.1) | 64.0 (51.8-76.1) | |
| 2M BHB/M/DMSO | 87.8 (78.9-96.7) | 48.8 (39.4-58.2)^ | 66.5 (53.0-80.1) | |
| BHB/M/PVP | 86.7 (77.8-95.6) | 53.9 (45.0-62.8)^# | 63.5 (52.3-74.7) | |
| BHB/M/Exp | 87.4 (77.4-97.4) | 51.0 (41.0-61.0)^ | 68.9 (58.3-79.5) | |

TABLE 3-continued

Blood Gases and markers of organ function in Rats Exposed to
40% blood loss and treated with LR or different formulations of BHB/M

| Parameter | Baseline | S 30 min | S 270 min | Effects |
|---|---|---|---|---|
| ALT [U/dl] | | | | |
| Sham | | | 46 (−166-258) | G .0387 |
| No Treatment | 46 (−156-248) | 41 (−161-243) | | T .0001 |
| LR | 50 (−162-262) | 33 (−179-245) | 158 (−229-545) | G*T .3062 |
| 4M BHB/M/DMSO | 48 (−176-271) | 39 (−173-251) | 128 (−172-428) | |
| 2M BHB/M/DMSO | 44 (−168-256) | 32 (−180-244) | 768 (468-1068) | |
| BHB/M/PVP | 49 (−163-261) | 33 (−179-245) | 584 (310-857) | |
| BHB/M/Exp | 47 (−190-284) | 33 (−190-256) | 286 (49-523) | |
| AST [U/dl] | | | | |
| Sham | | | 85 (−150-319) | G .0230 |
| No Treatment | 70 (−154-293) | 82 (−142-305) | | T <.0001 |
| LR | 76 (−159-310) | 63 (−171-298) | 322 (−106-750) | G*T .2620 |
| 4M BHB/M/DMSO | 76 (−171-323) | 79 (−168-327) | 349 (17-680) | |
| 2M BHB/M/DMSO | 68 (−179-316) | 59 (−176-293) | 143 (−189-475) | |
| BHB/M/PVP | 77 (−185-339) | 68 (−167-302) | 943 (640-1245) | |
| BHB/M/Exp | 75 (−187-337) | 59 (−188-306) | 609 (346-871) | |
| Alk Phos [U/dl] | | | | |
| Sham | | | 123 (107-139) | G .3601 |
| No Treatment | 128 (112-143) | 107 (92-122) | | T <.0001 |
| LR | 123 (107-139) | 90 (74-106) | 116 (89-144) | G*T .8087 |
| 4M BHB/M/DMSO | 130 (114-147) | 98 (81-114) | 113 (92-135) | |
| 2M BHB/M/DMSO | 107 (91-123) | 95 (78-111) | 97 (76-119) | |
| BHB/M/PVP | 122 (106-138) | 88 (72-104) | 110 (90-130) | |
| BHB/M/Exp | 121 (103-138) | 91 (74-108) | 112 (94-129) | |
| BUN [U/dl] | | | | |
| Sham | | | 31.7 (29.2-34.2) | G <.0001 |
| No Treatment | 20.4 (18.0-22.7) | 21.1 (18.7-23.5) | | T .0001 |
| LR | 17.0 (14.5-19.5) | 19.3 (16.8-21.8) | 41.8 (37.4-46.3) | G*T .1334 |
| 4M BHB/M/DMSO | 18.0 (15.4-20.6) | 22.9 (20.4-25.4) | 40.2 (36.7-43.7) | |
| 2M BHB/M/DMSO | 14.2 (11.7-16.7) | 20.1 (17.6-22.6) | 45.1 (41.6-48.6) | |
| BHB/M/PVP | 17.1 (14.6-19.6) | 19.7 (17.2-22.2) | 40.7 (37.6-43.9) | |
| BHB/M/Exp | 17.3 (14.5-20.1) | 20.0 (17.4-22.6) | 43.7 (41.0-46.5) | |
| Creatinine [U/dl] | | | | |
| Sham | | | 0.37 (0.26-0.48) | G <.0001 |
| No Treatment | 0.39 (0.29-0.49) | 0.49 (0.39-0.59) | | T <.0001 |
| LR | 0.27 (0.16-0.38) | 0.47 (0.37-0.58) | 1.30 (1.10-1.50) | G*T .1766 |
| 4M BHB/M/DMSO | 0.26 (0.15-0.38) | 0.48 (0.37-0.59) | 0.98 (0.83-1.13) | |
| 2M BHB/M/DMSO | 0.30 (0.19-0.40) | 0.39 (0.28-0.50) | 0.91 (0.75-1.06) | |
| BHB/M/PVP | 0.25 (0.15-0.36) | 0.40 (0.29-0.50) | 0.84 (0.70-0.98) | |
| BHB/M/Exp | 0.27 (0.15-0.39) | 0.41 (0.30-0.52) | 1.00 (0.88-1.12) | |

Data are presented as least-squared means (95% confidence interval).
*$p < 0.05$ versus Sham at the same timepoint,
^versus No Treatment at the same timepoint,
versus LR at the same timepoint.
Alk Phos—alkaline phosphatase,
ALT—alanine aminotransferase,
AST—aspartate aminotransferase,
BUN—blood urea nitrogen,
% $SvO_2$—venous oxygen saturation Example 34—Hemolysis Hemolysis inducing-potential of the BHB/M formulations was evaluated both in vitro and in vivo (FIG. 26). To account for the effects of solution tonicity, BHB/M solutions containing DMSO, PVP or HPβCD/PVP/PEG were analyzed at two concentrations in vitro. At a concentration of 4M BHB/43 mM M, all three BHB/M solutions induced significantly more hemolysis than LR (FIG. 26A). When solution concentration was lowered to 2M BHB/21.5 mM M, hemolysis-induction decreased and only the solution containing DMSO induced significantly more hemolysis than LR (FIG. 26B). DMSO-containing solutions consistently induced the highest level of hemolysis, although differences between the three BHB/M formulations at equal concentrations were not statistically significant. To evaluate formulation effects on hemolysis-induction in vivo, free plasma hemoglobin was measured at the end of the completion of blood withdrawal in our rat model of hemorrhagic shock (FIG. 26C). A trend was observed similar to that observed in vitro: free plasma hemoglobin was highest after treatment with the 4M BHB/M/DMSO solution, followed by 2M BHB/M/DMSO. Free plasma hemoglobin in rats treated with BHB/M/PVP or BHB/M/Exp were comparable to those in rats receiving LR, and significantly lower than in the BHB/M/DMSO groups.

Both BHB/M/PVP and BHB/M/Exp are safe and effective in the lethal rat hemorrhagic shock model described herein. In fact, the data suggests that the efficacy of the BHB/M/Exp solution exceeded that of the original formulation in our model. Omitting DMSO resulted in significantly reduced in vitro and in vivo hemolysis in both BHB/M/PVP and BHB/M/Exp-treated rats, while other indicators of toxicity did not differ between formulations.

To generate lyophils to develop a formulation with short reconstitution time, lyophilization cycle process parameters were optimized after thermal analysis of prelyophilization solutions. The characterization of the BHB/M/Exp formulation and optimization of the lyophilization cycle are described below.

Example 35—Characterization of Pre-Lyophilization Solution

DSC heating curves of frozen solutions of (A) M/Exp, (B) BHB/M/Exp and (C) BHB are presented in FIG. 27. When a dilute solution is cooled, ice crystallization results in freeze-concentration. Further cooling leads to continued ice crystallization and, if solute crystallization is inhibited, formation of maximally freeze-concentrated solution. The glass transition of this freeze-concentrate, designated as Tg', is a critical parameter in designing the lyophilization process. The frozen M/Exp solution exhibited a baseline shift at ~−31° C., attributed to Tg' of the freeze concentrate, followed by an endotherm at ~3° C. due to ice melting (FIG. 27, line i). The DSC heating curve of frozen solution containing BHB/M/Exp (FIG. 27, line ii) or 2M BHB alone (FIG. 27, line iii) exhibited two baseline shifts, first at ~−69° C. (Tg') and the second starting at ~−53° C. attributed to softening. This was followed by an ice melting endotherm at ~−13° C. A baseline shift at ~−27° C., as observed in the M/Exp solution, was not discernible. Thus the thermal behavior of the formulation appeared to be governed by BHB in solution. There was no evidence of BHB crystallization during freezing. It is expected that BHB would remain amorphous in the freeze concentrate due to the presence of PVP, PEG and HPβCD, and crystallized only during drying.

Example 36—Freeze Drying Cycle—Development and Optimization

Our initial freeze-drying cycle (fast cooling rate, primary drying initiated at −25° C.; final secondary drying at 25° C.) yielded a lyophile with an unacceptably long reconstitution time of ~30 minutes. Therefore, the lyophilization cycle was optimized by slow and controlled cooling of the prelyophilization solution and extended freezing time to 6 hrs. The low glass transition temperature of the prelyophilization solution necessitated drying to be initiated at a low temperature, hence primary drying was initiated at −40° C. (100 mTorr). The shelf temperature was sequentially increased, with the final drying at 40° C. (details in the materials and methods section). The hygroscopic nature of PVP and PEG necessitated terminal drying to be conducted at high temperature, to be followed by vacuum drying. This optimized lyophilization cycle yielded a BHB/M/Exp lyophile with a reconstitution time of ~3 min.

Example 37—Lyophile Characterization

BHB 'as is' was previously extensively characterized through combination of water-sorption, variable temperature X-ray diffractometry and thermal analysis techniques, and it was established that BHB existed as BHB·0.25 $H_2O$ under ambient conditions. The XRD patterns of the final BHB/M/Exp lyophile and BHB alone presented in FIG. 28 are almost superimposable, suggesting that BHB crystallized as BHB·0.25$H_2O$ in the lyophile. No characteristic peaks of melatonin were discernible (PVP and HPβCD being amorphous; PEG 400 liquid at room temperature). The amorphous nature of M/Exp lyophile was revealed by the broad halo in its XRD pattern. The DSC heating curve of the lyophile is presented in FIG. 29. The lyophile containing M/Exp (FIG. 29, line i) exhibited no distinguishable thermal events, which may be due to an interplay of various formulation components (melatonin melting point 118° C.; PVP Tg ~99° C.; PEG 400 melting point ~4° C.; HPβCD no thermal event at <275° C.). The heating curve of BHB (FIG. 29, line iii) revealed a broad endotherm over 80-130° C., attributed to water loss, followed by two additional thermal events at higher temperatures. The BHB/M/Exp lyophile (FIG. 29, line ii) exhibited one broad endotherm from 80 to 120° C., which can be attributed to water loss. The two high temperature endotherms with peaks at 132° C. and 148° C. may correspond to altered thermal behavior of BHB due to presence of excipients in the formulation.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A resuscitation composition comprising about 40 mM to 45 mM melatonin, about 3.8 M to about 4.2 M beta-hydroxybutyrate (BHB) or a pharmaceutically acceptable salt thereof in a solution of about 8% to about 12% hydroxypropyl-beta-cyclodextrin (HPbCD), about 4% to about 6% polyvinylpyrrolidone (PVP) and about 4% to about 6% polyethylene glycol (PEG).

2. The composition of claim 1, comprising about 43 mM melatonin.

3. The composition of claim 1, comprising about 4.0 M BHB.

4. The composition of claim 1, comprising about 10% HPbCD, 5% PVP, and 5% PEG.

5. The composition of claim 1, wherein the pharmaceutically acceptable salt is Na-BHB.

6. The composition of claim 1, wherein the composition is lyophilized.

7. The composition of claim 1, wherein the composition further comprises a stabilizer.

8. An article of manufacture comprising the composition of claim 1.

9. A method for treating an individual who is experiencing or has experienced a major hemorrhagic event, comprising administering the composition of claim 1 to the individual.

10. The method of claim 9, wherein the composition is administered to the individual before the individual has lost about 10% blood volume.

11. The method of claim 9, wherein the composition is administered to the individual before the individual has lost about 20% blood volume.

12. The method of claim 9, wherein the composition is administered to the individual before the individual has lost about 30%.blood volume.

13. The method of claim 9, wherein the blood loss in the individual results in a systolic blood pressure of about 70 mm Hg or less.

14. The method of claim 9, wherein the composition is administered at a volume of about 0.1 to about 5 milliliters (mls) per kilogram (kg) of weight of the individual.

15. The method of claim 9, wherein the composition is administered at a volume of about 0.1 to about 5 mLs per kg of weight of the individual per hour.

16. The method of claim 9, wherein the composition is administered intravenously or intraosseously.

17. The method of claim 9, further comprising transfusing the individual with blood or plasma.

* * * * *